(12) United States Patent
Cherrier et al.

(10) Patent No.: US 7,491,710 B2
(45) Date of Patent: Feb. 17, 2009

(54) ORGANOPHOSPHORUS DERIVATIVES OF INDAZOLES AND USE THEREOF AS MEDICINAL PRODUCTS

(75) Inventors: Marie-Pierre Cherrier, Ivry sur Seine (FR); Francois Clerc, Antony (FR); Alain Commercon, Vitry sur Seine (FR); Patrick Mailliet, Fontenay Sous Bois (FR); Hervé Minoux, Thiais (FR); Bruno Filoche-Rommé, Creteil (FR)

(73) Assignee: Aventis Pharma S.A., Antony (FR)

( * ) Notice: Subject to any disclaimer, the term of this patent is extended or adjusted under 35 U.S.C. 154(b) by 566 days.

(21) Appl. No.: 11/016,595

(22) Filed: Dec. 17, 2004

(65) Prior Publication Data

US 2005/0137171 A1 Jun. 23, 2005

(30) Foreign Application Priority Data

Dec. 17, 2003 (FR) .................................. 03 14778

(51) Int. Cl.
*A61K 31/675* (2006.01)
(52) U.S. Cl. ........................................ 514/80; 548/114
(58) Field of Classification Search ................... 514/80; 548/114
See application file for complete search history.

(56) References Cited

FOREIGN PATENT DOCUMENTS

| EP | 1256574 | 11/2002 |
|---|---|---|
| WO | WO 03/064397 | 8/2003 |
| WO | WO 03/078402 | 9/2003 |

*Primary Examiner*—Kamal A Saeed
(74) *Attorney, Agent, or Firm*—Kelly L. Bender; Balaram Gupta

(57) ABSTRACT

The present invention relates in particular to novel chemical compounds, particularly to novel organophosphorus derivatives of indazoles, to the compositions containing them, and to the use thereof as medicinal products for treating cancers.

19 Claims, No Drawings

ORGANOPHOSPHORUS DERIVATIVES OF INDAZOLES AND USE THEREOF AS MEDICINAL PRODUCTS

This application claims the benefit of priority of French Patent Application No. 03/14,778, filed Dec. 17, 2003, which is incorporated herein by reference in its entirety.

BACKGROUND OF THE INVENTION

1. Field of the Invention

The present invention relates in particular to novel chemical compounds, particularly to novel organophosphorus derivatives of indazoles, to compositions containing them, and to the use thereof as medicinal products. More particularly, the invention relates to a series of specific indazoles having anticancer activity, through modulating the activity of proteins, in particular of kinases.

2. Description of the Art

To date, most of the commercial compounds used in chemotherapy are cytotoxic which pose considerable problems of side effects and of tolerance with respect to the patients. These effects could be limited insofar as the medicinal products used act selectively on cancer cells, with the exclusion of normal cells. One of the solutions for limiting the adverse effects of a chemotherapy may therefore consist of the use of medicinal products which act on metabolic pathways or elements constituting these pathways, expressed mainly in cancer cells, and which are not expressed, or expressed very little, in normal cells.

Protein kinases are a family of enzymes which catalyze the phosphorylation of hydroxyl groups of specific residues of proteins such as tyrosine, serine or threonine residues. Such phosphorylations can greatly modify the function of the proteins; thus, protein kinases play an important role in regulating a large variety of cell processes, including in particular metabolism, cell proliferation, cell differentiation, cell migration or cell survival. Among the various cell functions in which the activity of a protein kinase is involved, some processes represent attractive targets for treating cancer-related diseases and also other diseases.

Thus, one of the objects of the present invention is to propose compositions which have anticancer activity, by acting in particular with respect to kinases. Among the kinases for which modulation of the activity is desired, Aurora 2 and Tie2 are preferred.

Many proteins involved in chromosome segregation and spindle assembly have been identified in yeast and *drosophila*. Disorganization of these proteins results in non-segregation of chromosomes and in monopolar or disorganized spindles. Among these proteins, certain kinases, including Aurora and lpl1, originating respectively from *drosophila* and from *S. cerevisiae*, are necessary for chromosome segregation and centrosome separation. A human analog of yeast lpl1 has recently been cloned and characterized by various laboratories. This kinase, called aurora2, STK15 or BTAK, belongs to the serine/threonine kinase family. Bischoff et al. have shown that Aurora2 is oncogenic and is amplified in human colorectal cancers (EMBO J, 1998, 17, 3052-3065). This has also been exemplified in cancers involving epithelial tumors, such as breast cancer.

Among the other kinases on which the products of the invention may act, mention may be made of FAK, KDR, Src, Tie2 and cyclin-dependent kinases (CDKs).

FAK is a cytoplasmic tyrosine kinase which plays an important role in transduction of the signal transmitted by integrins, a family of heterodimeric cell adhesion receptors. FAK and the integrins are located in perimembrane structures called adhesion plaques. It has been shown, in many cell types, that the activation of FAK and also the phosphorylation thereof on tyrosine residues, and in particular the autophosphorylation thereof on tyrosine 397, depend on binding of the integrins to their extracellular ligands, and therefore induced during cell adhesion [Kornberg L, et al. J. Biol. Chem. 267 (33): 23439-442. (1992)]. The autophosphorylation of FAK on tyrosine 397 represents a binding site for another tyrosine kinase, Src, via its SH2 domain [Schaller et al. Mol. Cell. Biol. 14:1680-1688. 1994; Xing et al. Mol. Cell. Biol. 5:413-421. 1994]. Src can then phosphorylate FAK on tyrosine 925, thus recruiting the Grb2 adaptor protein and inducing, in certain cells, activation of the ras and MAP kinase pathway involved in the control of cell proliferation [Schlaepfer et al. Nature; 372:786-791. 1994; Schlaepfer et al. Prog. Biophy. Mol. Biol. 71:435-478. 1999; Schlaepfer and Hunter, J. Biol. Chem. 272:13189-13195. 1997]. The activation of FAK can also induce the jun NH2-terminal kinase (JNK) signaling pathway and result in the progression of cells to the G1 phase of the cell cycle [Oktay et al., J. Cell. Biol. 145:1461-1469. 1999]. Phosphatidylinositol-3-OH kinase (PI3-kinase) also binds to FAK on tyrosine 397 and this interaction could be necessary for the activation of PI3-kinase [Chen and Guan, Proc. Nat. Acad. Sci. USA. 91:10148-10152. 1994; Ling et al. J. Cell. Biochem. 73:533-544. 1999]. The FAK/Src complex phosphorylates various substrates such as paxillin and p130CAS in fibroblasts [Vuori et al. Mol. Cell. Biol. 16:2606-2613. 1996].

The results of many studies support the hypothesis that FAK inhibitors could be used in the treatment of cancer. Studies have suggested that FAK may play an important role in cell proliferation and/or survival in vitro. For example, in CHO cells, some authors have demonstrated that overexpression of p125FAK results in an acceleration of G1 to S transition, suggesting that p125FAK promotes cell proliferation [Zhao J.-H et al. J. Cell Biol. 143:1997-2008. 1998]. Other authors have shown that tumor cells treated with FAK antisense oligonucleotides lose their adhesion and enter into apoptosis (Xu et al, Cell Growth Differ. 4:413-418. 1996). It has also been demonstrated that FAK promotes cell migration in vitro. Thus, fibroblasts deficient for the expression of FAK (FAK "knockout" mice) exhibit a rounded morphology and deficiencies in cell migration in response to chemotactic signals, and these deficiencies are eliminated by re-expression of FAK [D J. Sieg et al., J. Cell Science. 112:2677-91. 1999]. Overexpression of the C-terminal domain of FAK (FRNK) blocks elongation of adherent cells and reduces cell migration in vitro [Richardson A. and Parsons J. T. Nature. 380:538-540. 1996]. Overexpression of FAK in CHO or COS cells or in human astrocytoma cells promotes cell migration. The involvement of FAK in promoting proliferation and migration of cells in many cell types, in vitro, suggests a potential role for FAK in neoplastic processes. A recent study has effectively demonstrated an increase in tumor cell proliferation in vivo after induction of FAK expression in human astrocytoma cells [Cary L. A. et al. J. Cell Sci. 109:1787-94. 1996; Wang D et al. J. Cell Sci. 113:4221-4230. 2000]. In addition, immunohistochemical studies of human biopsies have demonstrated that FAK is overexpressed in prostate cancers, breast cancers, thyroid cancers, colon cancers, melanomas, brain cancers and lung cancers, the level of expression of FAK being directly correlated with the tumors exhibiting the most aggressive phenotype [Weiner T M, et al. Lancet. 342(8878):1024-1025. 1993; Owens et al. Cancer Research. 55:2752-2755. 1995; Maung K. et al. Oncogene. 18:6824-6828. 1999; Wang D et al. J. Cell Sci. 113:4221-4230. 2000].

KDR (Kinase insert Domain Receptor), also called VEGF-R2 (Vascular Endothelial Growth Factor Receptor 2), is expressed only in endothelial cells. This receptor binds to the angiogenic growth factor VEGF, and thus serves as a mediator for a transduction signal via activation of its intracellular kinase domain. Direct inhibition of the kinase activity of VEGF-R2 makes it possible to reduce the phenomenon of angiogenesis in the presence of exogenous VEGF (Vascular Endothelial Growth Factor: Facteur de croissance vasculaire endothélial) (Strawn et al., Cancer Research, 1996, vol. 56, p. 3540-3545). This process has been demonstrated in particular by means of VEGF-R2 mutants (Millauer et al., Cancer Research, 1996, vol. 56, p.1615-1620). The VEGF-R2 receptor seems to have no function in adults other than that related to the angiogenic activity of VEGF. Consequently, a selective inhibitor of the kinase activity of VEGF-R2 should only show slight toxicity.

In addition to this central role in the dynamic angiogenic process, recent results suggest that VEGF expression contributes to tumor cell survival after chemotherapy and radiotherapy, underlining the potential synergy of KDR inhibitors with other agents (Lee et al. Cancer Research, 2000, vol. 60, p. 5565-5570).

Tie-2 (TEK) is a member of a family of tyrosine kinase receptors, specific for endothelial cells. Tie2 is the first receptor with tyrosine kinase activity for which both the agonist (angiopoietin 1 or Ang1), which stimulates autophosphorylation of the receptor and cell signaling [S. Davis et al (1996) Cell 87, 1161-1169] and the antagonist (angiopoietin 2 or Ang2) [P. C. Maisonpierre et al. (1997) Science 277, 55-60] are known. Angiopoietin 1 can synergize with VEGF in the final stages of neoangiogenesis [Asahara T. Circ. Res.(1998) 233-240]. Knockout experiments and transgenic manipulations of Tie2 expression or of Ang1 expression result in animals which exhibit vascularization deficiencies [D. J. Dumont et al (1994) Genes Dev. 8, 1897-1909 and C. Suri (1996) Cell 87, 1171-1180]. The binding of Ang1 to its receptor results in autophosphorylation of the kinase domain of Tie2, which is essential for neovascularization and for the recruitment and the interaction of the vessels with the pericytes and the smooth muscle cells; these phenomena contribute to the maturation and stability of the newly formed vessels [P. C. Maisonpierre et al (1997) Science 277, 55-60]. Lin et al (1997) J. Clin. Invest. 100, 8: 2072-2078 and Lin P. (1998) PNAS 95, 8829-8834, have shown an inhibition of tumor growth and vascularization, and also a decrease in lung metastases, during adenoviral infections or injections of the extracellular domain of Tie-2 (Tek) in melanoma and breast tumor xenographed models.

Tie2 inhibitors can be used in situations where neovascularization occurs inappropriately (i.e. in diabetic retinopathy, chronic inflammation, psoriasis, Kaposi's sarcoma, chronic neovascularization due to macular degeneration, rheumatoid arthritis, infantile hemangioma and cancers).

The progression of the cell cycle is often controlled by cyclin-dependent kinases (CDK) which are activated by a balance in the cyclin family, which activation ends with the phosphorylation of substrates and, finally, with cell division. In addition, the endogenous CDK inhibitors which are activated (INK4 and KIP/CIP family) negatively regulate CDK activity. Normal cell growth is due to a balance between CDK activators (cyclins) and endogenous CDK inhibitors. In several types of cancers, aberrant expression or activity of several components of the cell cycle has been described.

Cyclin E activates the Cdk2 kinase, which then acts to phosphorylate pRb, resulting in irreversible entry into cell division and transition to the S phase (P L Toogood, Medicinal Research Reviews (2001), 21(6); 487-498), it is also possible, according to these authors, that the CDK2 and CDK3 kinases are necessary for progression in the G1 phase and entry into S phase. During the formation of a complex with cyclin E, they maintain the hyperphosphorylation of pRb so as to aid the progression of the G1 phase to S phase. In the complexes with cyclin A, CDK2 plays a role in the inactivation of E2F and is necessary for realizing the S phase (T D. Davies et al. (2001) Structure 9, 389-3).

The CDK1/cyclin B complex regulates the progression of the cell cycle between the G2 phase and the M phase. Negative regulation of the CDK/cyclin B complex prevents normal cells from entering into S phase before the G2 phase has been correctly and completely effected (K. K. Roy and E. A. Sausville Current Pharmaceutical Design, 2001, 7, 1669-1687.

A level of regulation of CDK activity exists. Cyclin-dependent kinase activators (CAKs) have a positive regulatory action on CDKs. CAK phosphorylates CDKs on the threonine residue so as to render the target enzyme completely active.

The presence of deficiencies in the molecules involved in the cell cycle results in the activation of CDKs and progression of the cycle, thus it seems evident that there is a need to inhibit the activity of the CDK enzymes in order to block cell growth in cancer cells.

All of the references described hereinabove are incorporated herein by reference in their entirety.

The present invention relates to novel organophosphorus derivatives of indazoles. It also relates to the use of organophosphorus derivatives of indazoles modified in the 5-position, as kinase inhibiting agents, and more particularly as anticancer agents. Among these, the invention preferably relates to 5-phosphono- and 5-phosphinoindazoles. It also relates to the use of said derivatives for preparing a medicinal product intended for treating humans.

Among the prior art known to date that describes 5-phosphoindazoles, mention may be made of the patent application published under the number WO93/18008, which is incorporated herein by reference in its entirety. This reference describes derivatives of the formula below:

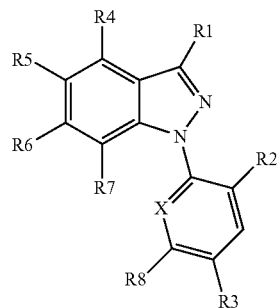

in which: X=N, CR14 (R14=H, alkyl . . . ); R1=H or halogen; R2=H, NO$_2$, halogen, alkyl . . . ; R3=H, halogen, haloalkyl, haloalkoxy, CN, NH2 . . . ; R4-R6=H, NO$_2$, halo, alkyl, etc., alkylsulfonamido, etc., P(=L)(Q)(M); L=O, S; M, Q=alkoxy, alkyl, (alkyl)$_n$amino, OH, H, alkenyloxy, (alkenyl)$_n$amino, alkynyloxy, (alkynyl)$_n$amino; R7=H, halo, alkyl, NO$_2$; and R8=H, halogen.

Among the compounds disclosed therein, only compounds 147, 161 and 163 are indazoles substituted with a phosphorus-containing group in the 5-position, and are excluded from the present invention as such. On the other hand, these products as medicinal products are part of the present invention. Whereas the compounds disclosed in the aforementioned application have a use in agronomy, i.e., agricultural uses. As mentioned, the compounds of the present invention have a pharmaceutical use.

SUMMARY OF THE INVENTION

According to a first aspect, the invention relates to products of formula (I) below:

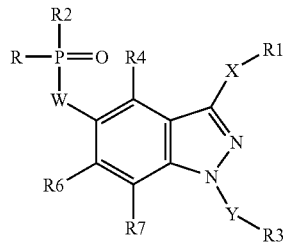

(I)

in which

W represents a group chosen from a covalent bond or O;

X represents a covalent bond, a group —C=O—$NR_a$—, $NR_a$—C=O, —$(CH_2)_n$—, —CH=CH—, —C≡C—, —$NR_a$—, S, O, —$SO_2$—, —SO, —CO or —COO in which $R_a$ represents H or a ($C_1$-$C_4$)alkyl group which can optionally form a ring with R1, and in which n=0, 1, 2, 3, 4, 5, 6, 7, 8, 9, 10, 11 or 12;

$R_1$ represents H (except when X=—$SO_2$— or —SO—), alkyl, cycloalkyl, aryl or heteroaryl; in which $R_1$ can be optionally substituted;

R and $R_2$, which may be identical or different, represent independently of each other H or a group chosen from alkyl, cycloalkyl, heterocycloalkyl, aryl, heteroaryl, hydroxyl, alkoxy and aryloxy radicals, in which R and $R_2$ are optionally substituted;

Y represents a covalent bond or a radical chosen from: —C=O—$NR_a$—, —C=O—O—, —C=O—, —$(CH_2)_n$— or —$SO_2$—, in which $R_a$ is selected from the group consisting of H, ($C_1$-$C_4$)alkyl and ($C_1$-$C_4$) alkyl linked to R3 so as to form a ring;

$R_3$ is selected from the group consisting of H (except when Y is —C=O—O—, or —$SO_2$—), alkyl, cycloalkyl, aryl, and heteroaryl; $R_3$ can optionally be substituted;

R4, R6 and R7, which may be identical or different, can be independently chosen from: H, halogen, ($C_1$-$C_4$)alkyl, ($C_1$-$C_4$)alkoxy, cyano, —N($R_b$)$R_c$, —C=O—N($R_b$)$R_c$ and —N($R_b$)—CO—$R_c$, in which $R_b$ and $R_c$ are independently chosen from H, ($C_1$-$C_4$)alkyl and ($C_3$-$C_6$)cycloalkyl;

with the exception of the products below

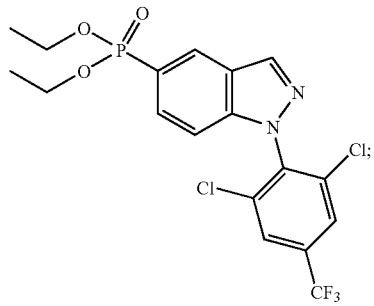

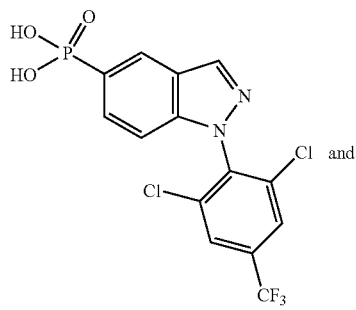

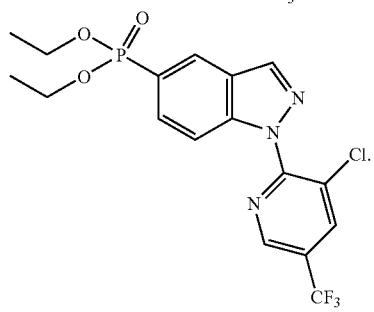

DETAILED DESCRIPTION OF THE INVENTION

The terms as used herein have the following meanings:

As used herein, the expression "$C_{1-6}$alkyl" includes methyl and ethyl groups, and straight-chained or branched propyl, butyl, pentyl and hexyl groups. Particular alkyl groups are methyl, ethyl, n-propyl, isopropyl and tert-butyl. Derived expressions such as "$C_{1-4}$alkoxy", "$C_{1-4}$thioalkyl" "$C_{1-4}$alkoxy$C_{1-4}$alkyl", "hydroxy$C_{1-4}$alkyl", "$C_{1-4}$alkylcarbonyl", "$C_{1-4}$alkoxycarbonyl$C_{1-4}$alkyl", "$C_{1-4}$alkoxycarbonyl", "amino$C_{1-4}$alkyl", "$C_{1-4}$alkylamino","$C_{1-4}$alkylcarbamoyl$C_{1-6}$alkyl", "$C_{1-4}$dialkylcarbamoyl$C_{1-4}$alkyl" "mono- or di-$C_{1-4}$alkylamino$C_{1-4}$alkyl", "amino$C_{1-4}$alkylcarbonyl" "diphenyl$C_{1-4}$alkyl", "phenyl$C_{1-4}$alkyl", "phenylcarboyl $C_{1-4}$alkyl" and "phenoxy$C_{1-4}$alkyl" are to be construed accordingly.

As used herein, the expression "cycloalkyl" includes all of the known cyclic radicals. Representative examples of "cycloalkyl" includes without any limitation cyclopropyl, cyclobutyl, cyclopentyl, cyclohexyl, cycloheptyl, cyclooctyl, and the like. Derived expressions such as "cycloalkoxy", "cycloalkylalkyl", "cycloalkylaryl", "cycloalkylcarbonyl" are to be construed accordingly.

As used herein, the expression "aryl" means substituted or unsubstituted phenyl or naphthyl, and the like. Specific examples of substituted phenyl or naphthyl include o-, p-, m-tolyl, 1,2-, 1,3-, 1,4-xylyl, 1-methylnaphthyl, 2-methylnaphthyl, etc. "Substituted phenyl" or "substituted naphthyl"

also include any of the possible substituents as further defined herein or one known in the art. Derived expression, "$C_{6-12}$arylsulfonyl," is to be construed accordingly.

As used herein, the expression "aryl$C_{1-4}$alkyl" means that the aryl as defined herein is further attached to $C_{1-4}$alkyl as defined herein. Representative examples include benzyl, phenylethyl, 2-phenylpropyl, 1-naphthylmethyl, 2-naphthylmethyl and the like.

As used herein, the expression "heteroaryl" includes all of the known heteroatom containing aromatic radicals. Representative 5-memebered heteroaryl radicals include furanyl, thienyl or thiophenyl, pyrrolyl, isopyrrolyl, pyrazolyl, imidazolyl, oxazolyl, thiazolyl, isothiazolyl, and the like. Representative 6-membered heteroaryl radicals include pyridinyl, pyridazinyl, pyrimidinyl, pyrazinyl, triazinyl, and the like radicals. Representative examples of bicyclic heteroaryl radicals include, benzofuranyl, benzothiophenyl, indolyl, quinolinyl, isoquinolinyl, cinnolyl, benzimidazolyl, indazolyl, pyridofuranyl, pyridothienyl, and the like radicals.

"Halogen" or "halo" means chloro, fluoro, bromo, and iodo. As used herein, "patient" means a warm blooded animal, such as for example rat, mice, dogs, cats, guinea pigs, and primates such as humans.

As used herein, the expression "pharmaceutically acceptable carrier" means a non-toxic solvent, dispersant, excipient, adjuvant, or other material which is mixed with the compound of the present invention in order to permit the formation of a pharmaceutical composition, i.e., a dosage form capable of administration to the patient. One example of such a carrier is pharmaceutically acceptable oil typically used for parenteral administration.

The term "pharmaceutically acceptable salts" as used herein means that the salts of the compounds of the present invention can be used in medicinal preparations. Other salts may, however, be useful in the preparation of the compounds according to the invention or of their pharmaceutically acceptable salts. Suitable pharmaceutically acceptable salts of the compounds of this invention include acid addition salts which may, for example, be formed by mixing a solution of the compound according to the invention with a solution of a pharmaceutically acceptable acid such as hydrochloric acid, hydrobromic acid, sulfuric acid, methanesulfonic acid, 2-hydroxyethanesulfonic acid, p-toluenesulfonic acid, fumaric acid, maleic acid, hydroxymaleic acid, malic acid, ascorbic acid, succinic acid, glutaric acid, acetic acid, salicylic acid, cinnamic acid, 2-phenoxybenzoic acid, hydroxybenzoic acid, phenylacetic acid, benzoic acid, oxalic acid, citric acid, tartaric acid, glycolic acid, lactic acid, pyruvic acid, malonic acid, carbonic acid or phosphoric acid. The acid metal salts such as sodium monohydrogen orthophosphate and potassium hydrogen sulfate can also be formed. Also, the salts so formed may present either as mono- or di-acid salts and can exist substantially anhydrous or can be hydrated. Furthermore, where the compounds of the invention carry an acidic moiety, suitable pharmaceutically acceptable salts thereof may include alkali metal salts, e.g. sodium or potassium salts; alkaline earth metal salts, e.g. calcium or magnesium salts, and salts formed with suitable organic ligands, e.g. quaternary ammonium salts.

The expression "stereoisomers" is a general term used for all isomers of the individual molecules that differ only in the orientation of their atoms in space. Typically it includes mirror image isomers that are usually formed due to at least one asymmetric center, (enantiomers). Where the compounds according to the invention possess two or more asymmetric centers, they may additionally exist as diastereoisomers, also certain individual molecules may exist as geometric isomers (cis/trans). Similarly, certain compounds of this invention may exist in a mixture of two or more structurally distinct forms that are in rapid equilibrium, commonly known as tautomers. Representative examples of tautomers include keto-enol tautomers, phenol-keto tautomers, nitroso-oxime tautomers, imine-enamine tautomers, etc. It is to be understood that all such isomers and mixtures thereof in any proportion are encompassed within the scope of the present invention.

In a broad sense, the term "substituted" is contemplated to include all permissible substituents of organic compounds. In a few of the specific embodiments as disclosed herein, the term "substituted" means substituted with one or more substituents independently selected from the group consisting of $C_{1-6}$alkyl, $C_{2-6}$alkenyl, $C_{1-6}$perfluoroalkyl, phenyl, hydroxy, —$CO_2H$, an ester, an amide, $C_1$-$C_6$alkoxy, $C_1$-$C_6$thioalkyl, $C_1$-$C_6$perfluoroalkoxy, —$NH_2$, Cl, Br, I, F, —NH-lower alkyl, and —N(lower alkyl)$_2$. However, any of the other suitable substituents known to one skilled in the art can also be used in these embodiments.

"Therapeutically effective amount" means an amount of the compound which is effective in treating the named disease, disorder or condition.

The following is particularly preferred in the compounds of formula (I):

W is preferably O.

Preferred aryl and heteroaryl radicals are independently chosen from:

(i) monocyclic radicals containing from zero to four hetero atoms chosen from O, N and S, and (ii) condensed bicyclic radicals comprising:

(a) a monocyclic radical containing 5, 6, 7 or 8 ring members and containing from zero to four hetero atoms chosen from O, N and S, condensed with (b) another ring containing 5 or 6 ring members, and containing from zero to three hetero atoms chosen from O, N and S.

More preferably, the aryl or heteroaryl radicals are independently selected from the group consisting of: phenyl, pyridyl, pyrimidyl, triazinyl, pyrrolyl, imidazolyl, thiazolyl, furyl, thienyl, indolyl, indazolyl, azaindazolyl, isobenzofuranyl, isobenzothienyl, benzimidazolyl, benzoxazolyl, benzothiazolyl, arylvinylene, arylamido, arylcarboxamide, aralkylamine, quinolinyl, isoquinolinyl, cinnolyl, quinazolyl, naphthyridyl, triazolyl or tetrazolyl.

Very preferably, the aryl or heteroaryl radicals are independently selected from the group consisting of: phenyl, pyrrolyl, optionally substituted indolyl, and arylvinylene.

The invention is particularly advantageously implemented when X represents a covalent bond and R1 represents a heterocyclic radical, in particular indolyl, for the definition of the products of general formula (I).

A preferred R2 substituent is a ($C_1$-$C_4$)alkyl radical.

Preferably, Y is advantageously a bond, and R3 is H.

According to a second aspect, the invention relates to the use of a product according to its first aspect, in human therapy, in particular for treating diseases linked to the deregulation of kinases such as Tie2, Aurora-2, linked to the appearance of cancers.

According to a third aspect, the invention relates to a product of formula (I) below:

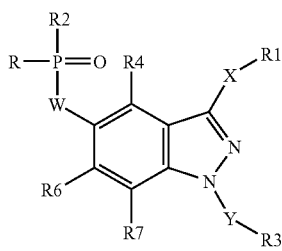

(I)

in which
- W represents a group chosen from a covalent bond or O;
- X represents a covalent bond, a group —C=O—NR$_a$—, NR$_a$—C=O, —(CH$_2$)$_n$—, —CH=CH—, —C≡C—, —NR$_a$—, S, O, —SO$_2$—, —SO, —CO or —COO in which R$_a$ represents H or a (C$_1$-C$_4$)alkyl group which can optionally form a ring with R1, and in which n is chosen from the range [0 to 12], these two limits inclusive;
- R$_1$ represents H (except when X=—SO$_2$— or —SO—), alkyl, cycloalkyl, aryl or heteroaryl; in which R$_1$ can be optionally substituted;
- R and R$_2$, which may be identical or different, represent independently of each other H or a group chosen from alkyl, cycloalkyl aryl, heteroaryl, hydroxyl, alkoxy and aryloxy radicals, in which R and R$_2$ are optionally substituted;
- Y represents a covalent bond or a radical chosen from: —C=O—NR$_a$—, —C=O—O—, —C=O—, —(CH$_2$)$_n$— or —SO$_2$—, in which R$_a$ is selected from the group consisting of H, (C$_1$-C$_4$)alkyl, and (C$_1$-C$_4$) alkyl linked to R3 so as to form a ring

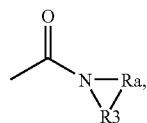

- R$_3$ is selected from the group consisting of H (except when Y=C=O—O or SO$_2$), alkyl, cycloalkyl, aryl and heteroaryl; R$_3$ can optionally be substituted;
- R4, R6 and R7, which may be identical or different, can be independently chosen from: H, halogen, (C$_1$-C$_4$)alkyl, (C$_1$-C$_4$)alkoxy, cyano, —N(R$_b$)R$_c$, —C=O—N(R$_b$)R$_c$ and —N(R$_b$)—CO—R$_c$, in which R$_b$ and R$_c$ are independently chosen from H, (C$_1$-C$_4$)alkyl and (C$_3$-C$_6$)cycloalkyl;

as a medicinal product.

Among the compounds corresponding to formula (I), mention may be made of the following compounds:
1) methylphosphonic acid methyl ester 3-[5-(2-morpholin-4-ylethoxy)-1H-indol-2-yl]-1H-indazol-5-yl ester
2) methylphosphonic acid methyl ester 3-{5-[2-(4-methylpiperazin-1-yl)-ethoxy]-1H-indol-2-yl}-1H-indazol-5-yl ester
3) phenylphosphonic acid methyl ester 3-thiophen-2-yl-1H-indazol-5-yl ester
4) (2-methanesulfonylphenyl)phosphonic acid 3-(1H-indol-2-yl)-1H-indazol-5-yl ester methyl ester
5) propylphosphonic acid 3-(1H-indol-2-yl)-1H-indazol-5-yl ester methyl ester
6) tert-butylphosphonic acid 3-(1H-indol-2-yl)-1H-indazol-5-yl ester methyl ester
7) cyclohexylphosphonic acid 3-(1H-indol-2-yl)-1H-indazol-5-yl ester methyl ester
8) (2-methoxyphenyl)phosphonic acid 3-(1H-indol-2-yl)-1H-indazol-5-yl ester methyl ester
9) (2-methylsulfanylphenyl)phosphonic acid 3-(1H-indol-2-yl)-1H-indazol-5-yl ester methyl ester
10) (2,6-dimethylphenyl)phosphonic acid 3-(1H-indol-2-yl)-1H-indazol-5-yl ester methyl ester
11) (2-trifluoromethoxyphenyl)phosphonic acid 3-(1H-indol-2-yl)-1H-indazol-5-yl ester methyl ester
12) thiophen-2-ylphosphonic acid 3-(1H-indol-2-yl)-1H-indazol-5-yl ester methyl ester
13) furan-2-ylphosphonic acid 3-(1H-indol-2-yl)-1H-indazol-5-yl ester methyl ester
14) methylphosphonic acid methyl ester 3-((E)-styryl)-1H-indazol-5-yl ester
15) phenylphosphonic acid methyl ester 3-((E)-styryl)-1H-indazol-5-yl ester
16) phenylphosphonic acid methyl ester 3-thiophen-2-yl-1H-indazol-5-yl ester
17) methylphosphonic acid methyl ester 3-thiophen-2-yl-1H-indazol-5-yl ester
18) methylphosphonic acid methyl ester 3-(1H-pyrrol-2-yl)-1H-indazol-5-yl ester
19) methylphosphonic acid 3-benzo[b]thiophen-2-yl-1H-indazol-5-yl ester methyl ester
20) phenylphosphonic acid 3-benzo[b]thiophen-2-yl-1H-indazol-5-yl ester methyl ester
21) phenylphosphonic acid 3-(5-methoxy-1H-pyrrolo[3,2-b]pyridin-2-yl)-1H-indazol-5-yl ester methyl ester
22) methylphosphonic acid 3-(5-methoxy-1H-pyrrolo[3,2-b]pyridin-2-yl)-1H-indazol-5-yl ester methyl ester

| Product | Structure |
|---------|-----------|
| 1 | 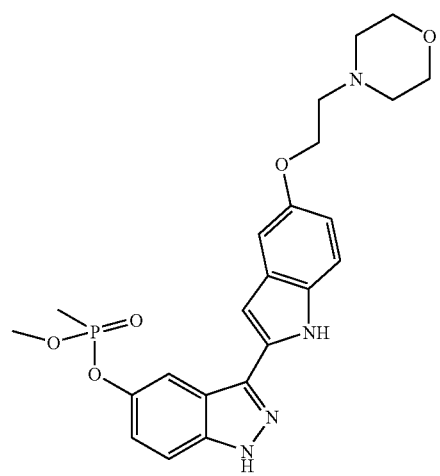 |

| Product | Structure |
|---|---|
| 2 | 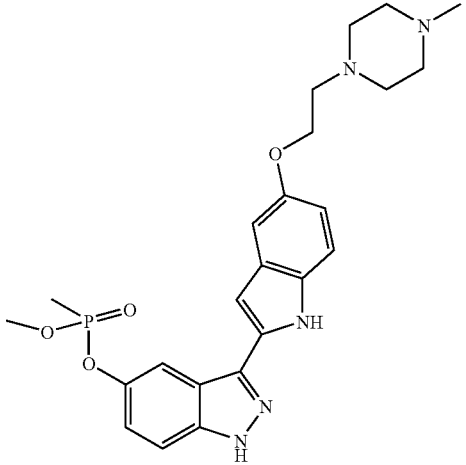 |
| 3 | 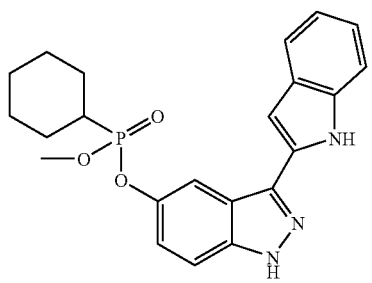 |
| 4 | 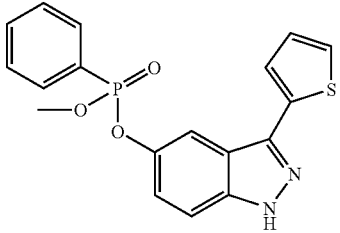 |
| 5 |  |
| 6 | 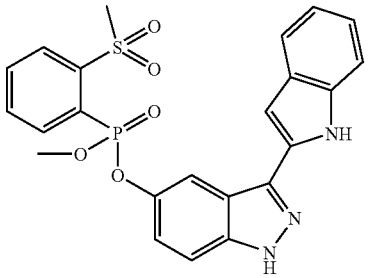 |
| Product | Structure |
|---|---|
| 7 | 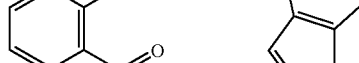 |
| 8 | 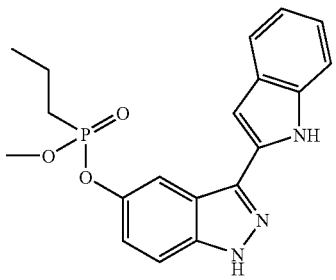 |
| 9 | 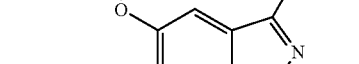 |
| 10 | 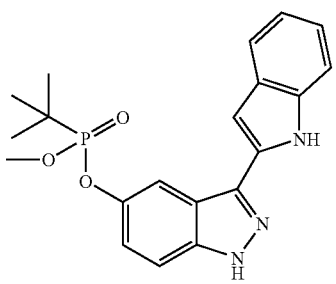 |
| 11 | 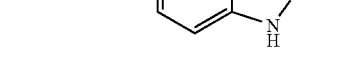 |

-continued

| Product | Structure |
|---|---|
| 12 | 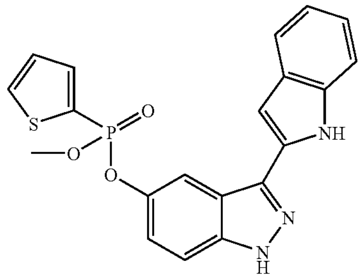 |
| 13 | 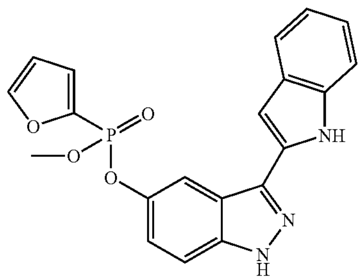 |
| 15 | |
| 15 | |
| 16 | 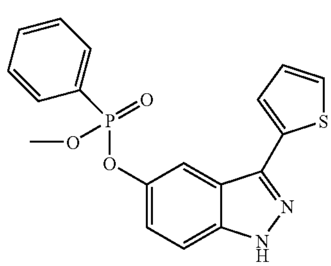 |
| 17 | 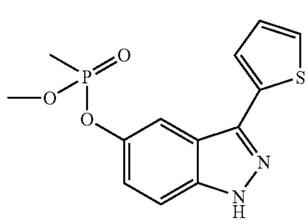 |

-continued

| Product | Structure |
|---|---|
| 18 | 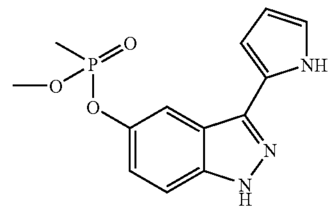 |
| 19 | 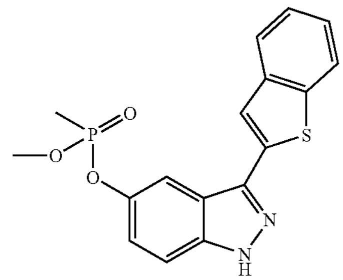 |
| 20 | 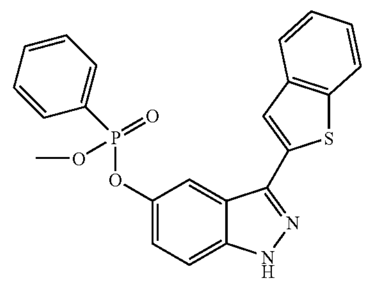 |
| 21 | 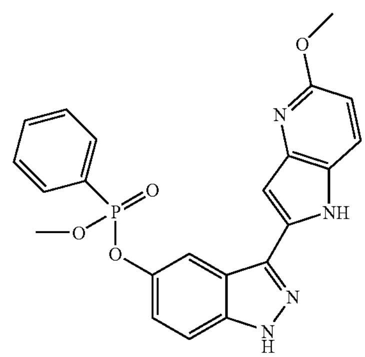 |
| 22 | 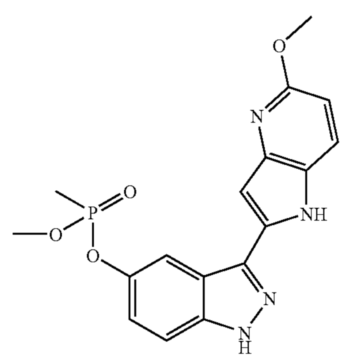 |

One of the processes for preparing the compounds according to the invention can be represented schematically in the following way:

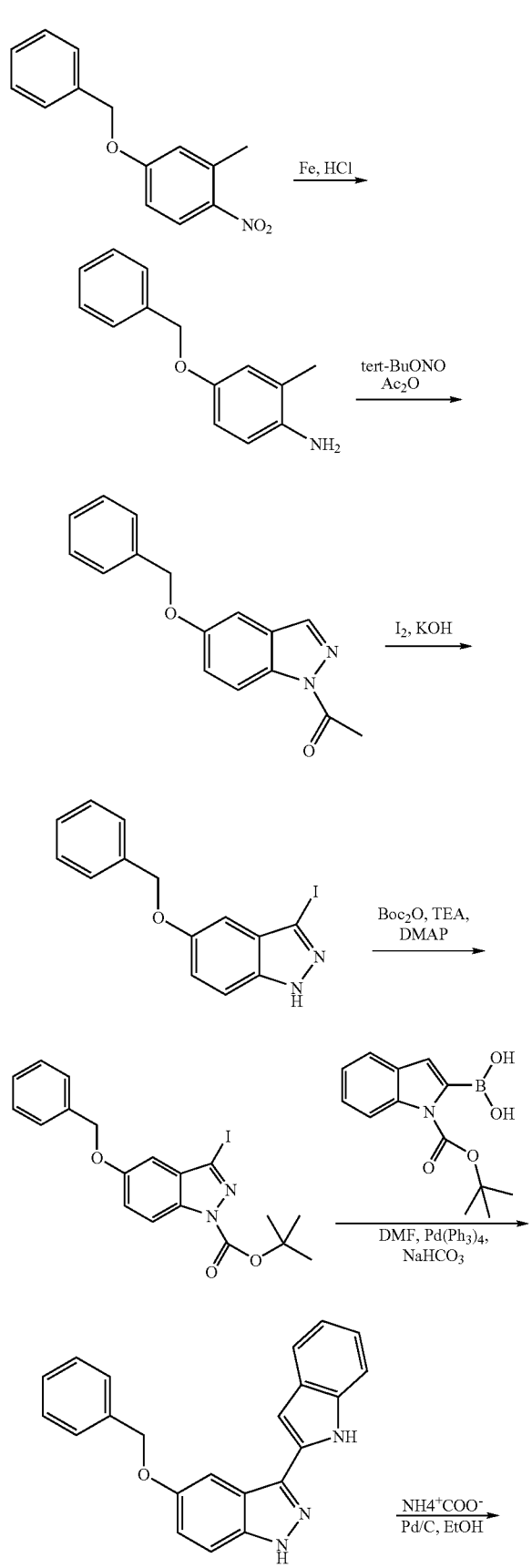

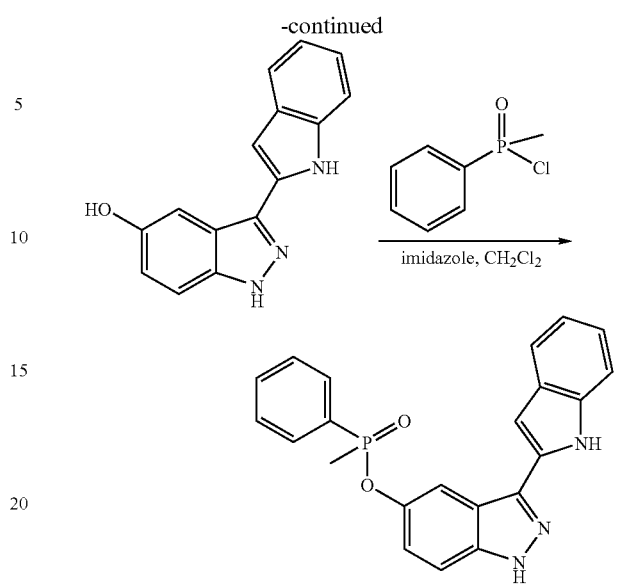

The compounds according to the invention can be used in human therapy, and more particularly in the treatment of cancer, more particularly of cancers sensitive to inhibitors of Aurora-2 and Tie2.

The present invention will be described more completely by means of the following examples, which should not be considered to limit the invention.

EXAMPLES (GENERAL)

LC/MS Analyses

The LC/MS analyses were carried out on a Micromass model LCT device connected to an HP 1100 device. The abundance of the products was measured using an HP G1315A diode array detector over a wavelength range of 200-600 nm and a Sedex 65 light scattering detector. The mass spectra were acquired over a range of 180 to 800. The data were analyzed using the Micromass MassLynx software. Separation was carried out on a Hypersil BDS C18, 3 μm (50×4.6 mm) column, by eluting with a linear gradient of from 5 to 90% of acetonitrile containing 0.05% (v/v) of trifluoroacetic acid (TFA) in water containing 0.05% (v/v) TFA, over 3.5 min at a flow rate of 1 ml/min. The total analysis time, including the period for re-equilibrating the column, is 7 min.

Purification by Preparative LC/MS:

The products were purified by LC/MS using a Waters FractionsLynx system composed of a Waters model 600 gradient pump, a Waters model 515 regeneration pump, a Waters Reagent Manager dilution pump, a Waters model 2700 auto-injector, two Rheodyne model LabPro valves, a Waters model 996 diode array detector, a Waters model ZMD mass spectrometer and a Gilson model 204 fraction collector. The system was controlled by means of the Waters FractionLynx software. Separation was carried out alternately on two Waters Symmetry columns ($C_{18}$, 5 μM, 19×50 mm, catalogue reference 186000210), one column undergoing regeneration with a 95/5 (v/v) water/acetonitrile mixture containing 0.07%

(v/v) of trifluoroacetic acid, while the other column was being used for separation. The columns were eluted using a linear gradient of from 5 to 95% of acetonitrile containing 0.07% (v/v) of trifluoroacetic acid in water containing 0.07% (v/v) of trifluoroacetic acid, at a flow rate of 10 ml/min. At the outlet of the separation column, one thousandth of the effluent is separated by means of an LC Packing Accurate, diluted with methyl alcohol at a flow rate of 0.5 ml/min and sent to the detectors, in a proportion of 75% to the diode array detector and the remaining 25% to the mass spectrometer. The rest of the effluent (999/1000) is sent to the fraction collector, where the flow is discarded for as long as the mass of expected product is not detected by the FractionLynx software. The molecular formulae of the expected products are supplied to the FractionLynx software, which actuates the collection of the product when the mass signal detected corresponds to the ion $[M+H]^+$ and/or to $[M+Na]^+$. In certain cases, depending on the analytical LC/MS results, when an intense ion corresponding to $[M+2H]^{++}$ was detected, the value corresponding to half the calculated molecular mass (MW/2) is also supplied to the FractionLynx software. Under these conditions, the collection is also actuated when the mass signal of the ion $[M+2H]^{++}$ and/or $[M+Na+H]^{++}$ are detected. The products were collected in tared glass tubes. After collection, the solvents were evaporated in a Savant AES 2000 or Genevac HT8 centrifugal evaporator and the masses of the products were determined by weighing the tubes after evaporation of the solvents.

Purification by Flash Chromatography: The crude products are purified by flash chromatography on silica with a particle size of 15-35 μm, under an argon pressure of 0.5 bar. The fractions corresponding to the expected product are combined and concentrated under reduced pressure in a rotary evaporator.

Intermediate A, 5-benzyloxy-3-iodoindazole-1-carboxylic acid tert-butyl ester, was prepared in 4 stages, according to scheme 1.

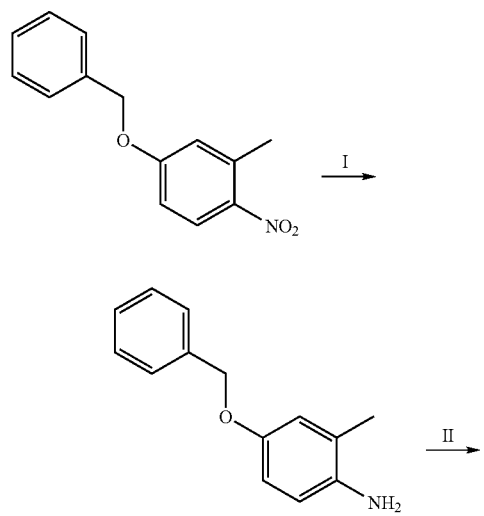

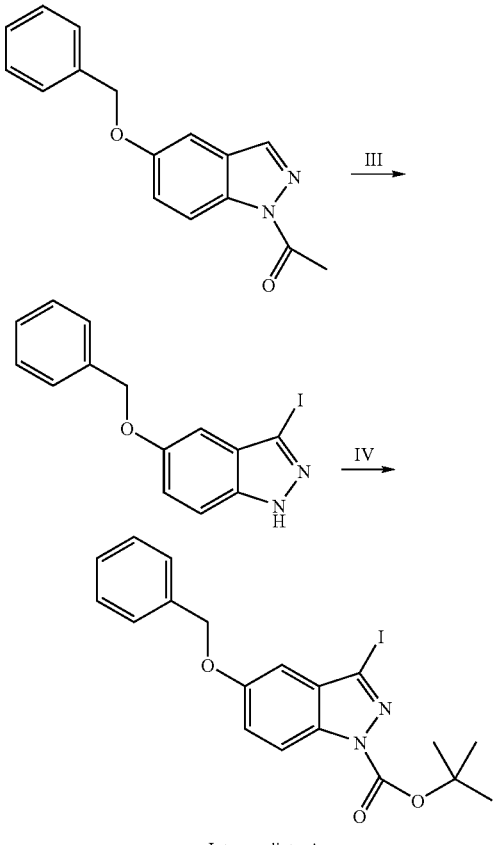

Intermediate A

Stage I: Preparation of 4-benzyloxy-2-methylphenylamine

A solution of 190 ml of concentrated hydrochloric acid in 300 ml of ethanol is added dropwise to a mixture of 50 g of 4-benzyloxy-2-methyl-1-nitrobenzene and of 46 g of zinc. The solution is cooled to around 45° C. by means of an ice bath throughout the running-in process. The medium is stirred for 3 hours at ambient temperature. The pH of the solution is adjusted to around pH 8 by adding 500 ml of a saturated potassium carbonate solution. The precipitate is filtered off and washed with 5×500 ml of ethyl acetate. The organic phases are combined and washed with 2×1 liter of distilled water, then with 1 liter of a saturated sodium chloride solution. After drying over magnesium sulfate, the solvent is evaporated off under reduced pressure in a rotary evaporator. The reaction crude is purified by flash chromatography (silica 35-70 μm), eluent: ethyl acetate/cyclohexane 80:20; 75:25; 70:30. 30.81 g of 4-benzyloxy-2-methylphenylamine are isolated.

$^1$H NMR spectrum (300 MHz, $(CD_3)_2SO$ d6, δ in ppm): 2.04 (s: 3H); 4.40 (broad s: 2H); 4.95 (s: 2H); 6.55 (d, J=8.5 Hz: 1H); 6.61 (dd, J=8.5 and 2.5 Hz: 1H); 6.68 (d, J=2.5 Hz: 1H); from 7.25 to 7.55 (mt: 5H).

Stage II: Preparation of 1-(5-benzyloxyindazol-1-yl)ethanone 10.5 ml of acetic anhydride are run into a solution of 7.14 g of 4-benzyloxy-2-methylphenylamine in 26 ml of toluene.

The medium is heated to around 90° C. and 9.28 ml of tert-butyl nitrite are run in to the solution, dropwise. The reaction medium is heated at around 90° C. for two hours. The reaction crude is concentrated to dryness in a rotary evaporator. The solid is taken up in ethyl acetate and then filtered and rinsed with isopropyl ether. 3.41 g of 1-(5-benzyloxyindazol-1-yl)ethanone are collected.

$^1$H NMR spectrum (300 MHz, $(CD_3)_2SO$ d6, δ in ppm): 2.72 (s: 3H); 5.21 (broad s: 2H); 7.34 (dd, J=9 and 2.5 Hz: 1H); from 7.35 to 7.50 (mt: 3H); 7.47 (d, J=2.5 Hz: 1H); 7.51 (broad dd, J=7.5 and 1.5 Hz: 2H); 8.23 (d, J=9 Hz: 1H); 8.39 (d, J=1 Hz: 1H).

Stage III: Procedure A Preparation of 5-benzyloxy-3-iodo-1H-indazole 68.84 g of iodine and then 23 g of potassium hydroxide are added to a solution of 28.24 g of 1-(5-benzyloxyindazol-1-yl)ethanone in 620 ml of dimethylformamide. The reaction medium is stirred at ambient temperature for approximately 3 hours. 23 g of potassium hydroxide are added and the medium is stirred at ambient temperature for 48 hours. The medium is treated with 600 ml of a sodium thiosulfate solution (100 g of sodium thiosulfate in 250 ml of distilled water), 600 ml of distilled water and 1 liter of ethyl acetate. The medium is stirred for a few minutes and is then separated by settling out. The aqueous phase is extracted with 4×600 ml of ethyl acetate. The combined organic phases are washed with 1 liter of a saturated sodium chloride solution, and then dried over magnesium sulfate. The solvent is evaporated off under reduced pressure in a rotary evaporator. The reaction crude is taken up in dichloromethane, and the solid is filtered off and rinsed with dichloromethane and with ethyl ether. 20.8 g of 5-benzyloxy-3-iodo-1H-indazole are collected.

$^1$H NMR spectrum (300 MHz, $(CD_3)_2SO$ d6, δ in ppm): 5.19 (broad s: 2H); 6.90 (d, J=2 Hz: 1H); 7.18 (dd, J=9 and 2 Hz: 1H); 7.35 (broad t, J=7.5 Hz: 1H); 7.43 (broad t, J=7.5 Hz: 2H); 7.50 (d, J=9 Hz: 1H); 7.52 (broad d), J=7.5 Hz: 2H); from 13.00 to 13.70 (very broad unresolved peak: 1H).

LC/MS: [M+H]$^+$=351.10; retention time: 3.97 minutes.

Stage IV: Procedure B Preparation of 5-benzyloxy-3-iodoindazole-1-carboxylic acid tert-butyl ester 1.70 g of 4-dimethylaminopyridine are added to a solution of 19.54 g of 5-benzyloxy-3-iodo-1H-indazole, 36.50 g of di-tert-butyl dicarbonate and 23.30 ml of triethylamine in 550 ml of dichloromethane. A substantial amount of gas is seen to be given off. The solution is stirred overnight at ambient temperature. The organic phase is washed with 2×500 ml of distilled water, dried over magnesium sulfate, filtered, and concentrated under reduced pressure in a rotary evaporator. The crude solid is taken up in acetonitrile. The solid is filtered off, and rinsed with acetonitrile and ethyl ether. 19.43 g of 5-benzyloxy-3-iodoindazole-1-carboxylic acid tert-butyl ester are collected. The filtrate is purified by flash chromatography (silica 70-200 μm), eluent: 3/97 ethyl acetate/cyclohexane. 3.05 g of 5-benzyloxy-3-iodoindazole-1-carboxylic acid tert-butyl ester are collected.

LC/MS : [M+H]+=451.08; retention time: 4.91 minutes.

Intermediate B, 5-benzyloxy-3-(1H-indol-2-yl)-1H-indazole, was prepared in two stages from intermediate A according to scheme 2:

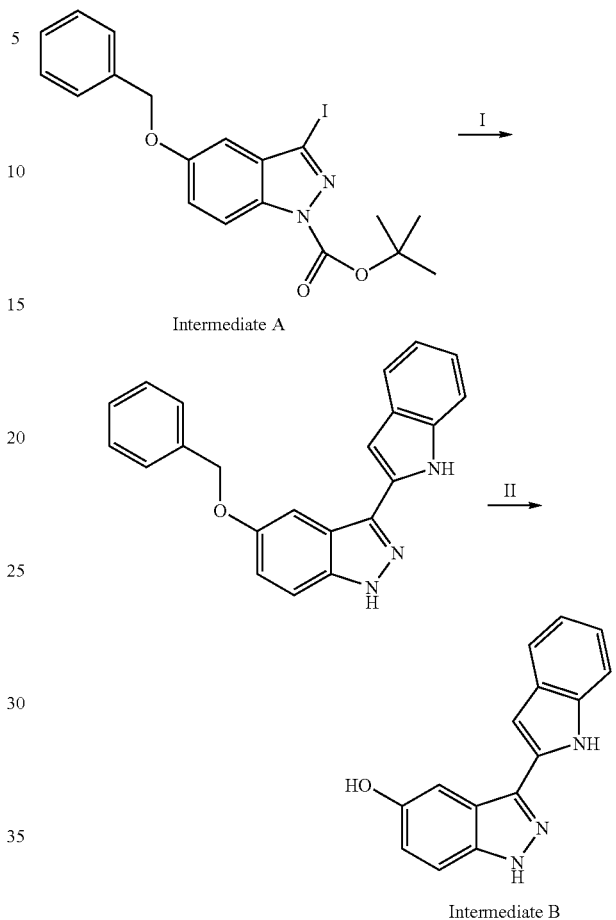

Procedure C

Stage Ia: Preparation of 2-[4-(1-tert-butoxycarbonyl-2,3-dihydro-1H-indol-2-yl)-1,3,2,4-dioxadiboretan-2-yl]indole-1-carboxylic acid tert-butyl ester according to the procedure described in the article by E. Vasquez, *J. Org. Chem.*, 67, 7551-7552 (2002).

21 ml of triisopropyl borate are added dropwise to a solution of 13 g of N-Boc indole in 50 ml of anhydrous THF. The reaction medium is cooled to around 5° C. 50 ml of a 1.5M LDA solution in THF are added dropwise so as to maintain the temperature of the medium at around 5° C. The solution is stirred for 90 minutes at this temperature and the medium is then treated with 40 ml of a 2N aqueous hydrochloric acid solution. The suspension is filtered and the solid is washed with 2×40 ml of THF. The filtrate is separated by settling out. The aqueous phase is extracted with 80 ml of ethyl acetate and the combined organic phases are then dried over magnesium sulfate and filtered. The solvent is evaporated off under reduced pressure in a rotary evaporator to obtain 19 g of 2-[4-(1-tert-butoxycarbonyl-2,3-dihydro-1H-indol-2-yl)-1,3,2,4-dioxadiboretan-2-yl]indole-1-carboxylic acid tert-butyl ester in the form of an orange oil.

LC/MS: [M+H]+=487.19; retention time: 3.30 minutes.

Stage Ib: A suspension of 3.23 g of 5-benzyloxy-3-iodoindazole-1-carboxylic acid tert-butyl ester, 7.31 g of 2-[4-(1-tert-butoxycarbonyl-2,3-dihydro-1H-indol-2-yl)-1,3,2,4-dioxadiboretan-2-yl]indole-1-carboxylic acid tert-butyl ester, 2.07 g of palladium tetrakistriphenylphosphine and 11 ml of a saturated aqueous sodium bicarbonate solution is heated at reflux for approximately two hours and then at ambient temperature overnight. The reaction medium is filtered through paper, and the filtrate is then diluted with 150 ml of ethyl acetate. The organic phase is washed with 200 ml of distilled water. The aqueous phase is extracted with 2×150 ml of ethyl acetate. The organic phases are combined and washed with a saturated aqueous sodium chloride solution, dried over magnesium sulfate and filtered. The solvent is evaporated off under vacuum in a rotary evaporator. The resulting crude product is purified by flash chromatography on silica 70-200 μm, eluent: cyclohexane/ethyl acetate gradient 95:5 to 70:30 to obtain 1.97 g of 5-benzyloxy-3-(1H-indol-2-yl)-1H-indazole.

$^1$H NMR spectrum (300 MHz, $(CD_3)_2SO$ d6, δ in ppm): 5.28 (broad s: 2H); 7.03 (split t, J=7.5 and 1.5 Hz: 1H); 7.12 (split t, J=7.5 and 1.5 Hz: 1H); 7.12 (broad s: 1H); 7.19 (dd, J=9 and 2.5 Hz: 1H); 7.36 (broad t, J=7.5 Hz: 1H); 7.44 (broad t, J=7.5 Hz: 2H); 7.47 (broad d, J=7.5 Hz: 1H); 7.54 (d, J=9 Hz: 1H); 7.58 (broad d, J=7.5 Hz: 2H); 7.62 (broad d, J=7.5 Hz: 1H); 7.65 (d, J=2.5 Hz: 1H); 11.50 (unresolved peak: 1H); from 12.90 to 13.40 (very broad unresolved peak: 1H).

LC/MS: [M+H]+=340.24; retention time: 4.23 minutes.

Stage II: Procedure D Preparation of 3-(1H-indol-2-yl)-1H-indazol-5-ol

A solution of 2.54 g of 3-(1H-indol-2-yl)-5-phenoxy-1H-indazole, of 2.83 g of ammonium formate and 2.54 g of palladium-on-charcoal at 10% in 150 ml of ethanol is refluxed for one hour. The catalyst is filtered through paper and rinsed with ethanol. The filtrate is concentrated to dryness to obtain 1.74 g of 3-(1H-indol-2-yl)-1H-indazol-5-ol.

$^1$H NMR spectrum (300 MHz, $(CD_3)_2SO$ d6, δ in ppm): 6.90 (d, J=1.5 Hz: 1H); from 6.95 to 7.05 (mt: 1H); 7.01 (dd, J=9 and 2.5 Hz: 1H); 7.10 (split t, J=7.5 and 1.5 Hz: 1H); 7.39 (d, J=2.5 Hz: 1H); from 7.40 to 7.50 (mt: 2H); 7.60 (broad d, J=7.5 Hz: 1H); 9.26 (broad s: 1H); 11.48 (broad s: 1H); 13.05 (broad s: 1H).

Analytical LC/MS: [M+H]$^+$=250.22; retention time: 3.16 minutes.

The compound, 5-benzyloxy-3-((E)-styryl)-1H-indazole is prepared according to procedure C, step Ib, using 300 mg of 5-benzyloxy-3-iodoindazole-1-carboxylic acid tert-butyl ester, 197 mg of E-phenylethenyl boronic acid, 192 mg of palladium tetrakistriphenylphosphine in suspension in 12 ml of dimethylformamide and 0.61 ml of a saturated sodium bicarbonate solution. The resulting crude product is treated as described hereinabove to obtain 150 mg of 5-benzyloxy-3-((E)-styryl)-1H-indazole.

$^1$H NMR spectrum (300 MHz, $(CD_3)_2SO$ d6, δ in ppm): 5.24 (broad s: 2H); 7.14 (dd, J=9 and 2 Hz: 1H); 7.30 (broad t, J=7.5 Hz: 1H); from 7.30 to 7.50 (mt:5H); 7.38 (d,J=16.5 Hz: 1H);7.49 (d,J=9 Hz: 1H); 7.56 (d, J=16.5 Hz: 1H); 7.56 (broad d, J=7.5 Hz: 2H); 7.68 (d, J=2 Hz: 1H); 7.73 (broad d, J=7.5 Hz : 2H); from 12.50 to 13.50 (very broad unresolved peak: 1H).

IR (KBr): 3178; 3153; 2924; 1587; 1497; 1228; 1075; 957; 947; 812; 787; 758 and 691 cm$^{-1}$.

Analytical LC/MS: [M+H]$^+$=327.24; retention time: 4.74 minutes.

Preparation of 3-styryl-1H-indazol-5-ol: A solution of 652 mg of 5-benzyloxy-3-((E)-styryl)-1H-indazole in 60 ml of acetonitrile is stirred under argon. 1.13 ml of iodotrimethylsilane are added dropwise under an inert atmosphere. The suspension is stirred at approximately 50° C. for 3 hours and then at ambient temperature overnight. The medium is heated to around 50° C. and then 1.2 ml of iodotrimethylsilane are added. After stirring for 3 hours, 0.8 ml of iodotrimethylsilane is added. After stirring for approximately 4 hours, the medium is treated with 10 ml of methanol and stirred at ambient temperature for about fifteen minutes. The suspension is filtered through a paper filter and the filtrate is concentrated under vacuum in a rotary evaporator. The reaction crude is taken up in 50 ml of ethyl acetate and the organic phase is washed with 2×50 ml of a sodium thiosulfate solution, 2×50 ml of a saturated sodium bicarbonate solution, and 50 ml of a saturated sodium chloride solution. The organic phase is dried over magnesium sulfate and then concentrated under vacuum in a rotary evaporator. The reaction crude is purified by flash chromatography on silica (Varian 20 g cartridge), eluent: ethyl acetate/cyclohexane gradient 5:95 to 35:65 to obtain 265.4 mg of 3-styryl-1H-indazol-5-ol.

$^1$H NMR spectrum (300 MHz, $(CD_3)_2SO$ d6, δ in ppm): 7.08 (dd, J=9 and 2 Hz: 1H); from 7.30 to 7.50 (mt: 4H); 7.31 (broad t, J=7.5 Hz: 1H); 7.38 (d, J=17 Hz: 1H); 7.49 (d, J=17 Hz: 1H); 7.69 (broad d, J=7.5 Hz: 2H); 9.20 (s: 1H); 12.41 (unresolved peak: 1H).

IR (KBr): 3397; 3261; 3058; 2923; 1629; 1490; 1222; 1071; 952; 846; 804; 787; 760; 742; 691; 564 cm$^{-1}$.

Analytical LC/MS: [M+H]$^+$=237.27; retention time: 3.16 minutes.

Procedure E: Preparation of the p-nitrophenol esters according to DS Tawfik, *Synthesis*, 968-972 (1993); S Gobec, *Tetrahedron Lett.*, 43,167-170 (2002).

The methylphenylphosphinic acid 4-nitrophenyl ester is prepared in the following way: A suspension of 173 mg of NaH at 50% in oil, in 2 ml of anhydrous tetrahydrofuran, is stirred at ambient temperature under argon. A solution of 500 mg of 4-nitrophenol in 2 ml of anhydrous tetrahydrofuran is added dropwise at ambient temperature. After stirring for approximately 1 hour at ambient temperature, a solution of 630 mg of methylphenylphosphinic chloride in 2 ml of anhydrous tetrahydrofuran is added dropwise over about ten minutes. After stirring for approximately 2 hours, the reaction medium is diluted with 20 ml of distilled water and the aqueous phase is extracted with 2×20 ml of dichloromethane. The combined organic phases are dried over magnesium sulfate, filtered, and concentrated under reduced pressure in a rotary evaporator. 995 mg of methylphenylphosphinic acid 4-nitrophenyl ester are obtained with a purity of 50%.

Analytical LC/MS : [M+H]$^+$=278.1; retention time: 3.16 minutes.

Example 1

Methylphenylphosphinic acid 3-((E)-styryl)-1H-indazol-5-yl ester

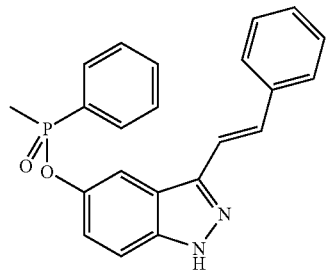

A solution of 20 mg of 3-styryl-1H-indazol-5-ol, 5.76 mg of imidazole and 20.7 mg of methylphenylphosphinic chloride in 5 ml of dichloromethane is stirred at ambient temperature. After stirring for approximately one hour, 5.76 mg of imidazole and 20.7 mg of methylphenylphosphinic chloride are added. The suspension is stirred at ambient temperature for approximately 18 hours. 10 mg of imidazole and 70 mg of methylphenylphosphinic chloride are added. After 30 hours at ambient temperature, the reaction medium is treated with 10 ml of distilled water. The aqueous phase is extracted with 2×10 ml of dichloromethane. The organic phase is dried over magnesium sulfate and concentrated under reduced pressure in a rotary evaporator. The reaction crude is purified by preparative LC/MS to obtain 9.1 mg of methylphenylphosphinic acid 3-((E)-styryl)-1H-indazol-5-yl ester.

$^1$H NMR spectrum (300 MHz, (CD$_3$)$_2$SO d6, δ in ppm): 1.93 (d, J=14.5 Hz: 3H); 7.23 (ddd, J=9-2and 1 Hz: 1H); 7.31 (d, J=17 Hz: 1H); 7.32 (broad t, J=7.5 Hz: 1H);7.43 (broad t, J=7.5 Hz: 2H); 7.50 (d, J=17 Hz: 1H); 7.50 (d, J=9 Hz: 1H); from 7.50 to 7.65 (mt: 3H); 7.70 (broad d, J=7.5 Hz: 2H); 7.82 (mt: 1H); 7.95 (ddd, J=12-7.5 and 1.5 Hz: 2H); 13.21 (unresolved peak: 1H).

IR (KBr): 3427; 3056; 2921; 1487; 143; 1211; 1183; 1124; 1070; 959; 911; 806; 783; 761; 745; 693 cm$^{-1}$.

Analytical LC/MS: [M+H]$^+$=375.22; retention time: 3.45 minutes.

Example 2

Diphenylphosphinic acid 3-((E)-styryl)-1H-indazol-5-yl ester

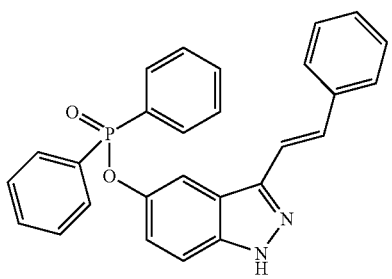

A solution of 70 mg of 3-styryl-1H-indazol-5-ol, 300 mg of imidazole and of 273 μl of diphenylphosphinyl chloride in 15 ml of dichloromethane is stirred at ambient temperature. After stirring for approximately 90 minutes, the medium is treated with 30 ml of distilled water. The aqueous phase is extracted twice with 30 ml of dichloromethane and the organic phases are then dried over magnesium sulfate, filtered, and concentrated under reduced pressure on a rotary evaporator. The crude is taken up with ethyl acetate. The solid is filtered through sintered glass, and rinsed with ethyl ether. The filtrate is concentrated under reduced pressure in a rotary evaporator, and purified by flash chromatography on silica 35-70 μm. Eluent: cyclohexane/ethyl acetate gradient of 80:20 to 70:30. 143 mg of a yellow solid are collected. This compound is purified by preparative LC/MS to obtain 47.3 mg of diphenylphosphinic acid 3-((E)-styryl)-1H-indazol-5-yl ester.

$^1$H NMR spectrum (300 MHz, (CD$_3$)$_2$SO d6, δ in ppm): 7.31 (d, J=17 Hz: 1H); 7.32 (broad t, J=7.5 Hz: 1H); 7.23 (broad dd, J=9 and 2 Hz: 1H); 7.44 (broad t, J=7.5 Hz: 2H); 7.50 (d, J=17 Hz: 1H); 7.50 (d, J=9 Hz: 1H); from 7.50 to 7.70 (mt: 6H); 7.70 (broad d, J=7.5 Hz: 2H); 7.97 (mt: 1H); 8.00 (ddd, J=12-8 and 2 Hz: 4H); 13.24 (broad unresolved peak: 1H).

IR (KBr): 3433; 3174; 3057; 1484; 1439; 1226; 1130; 1072; 962; 755; 734; 692 and 565 cm$^{-1}$.

Analytical LC/MS: [M+H]$^+$=437.16; retention time: 3.89 minutes.

Example 3

Methylphenylphosphinic acid 3-(1H-indol-2-yl)-1H-indazol-5-yl ester

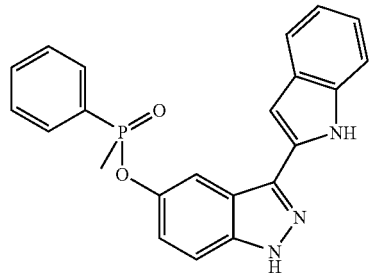

Procedure F:

A solution of 497 mg of 50%-pure methylphenylphosphinic acid 4-nitrophenyl ester in 8 ml of dichloromethane is stirred at ambient temperature. A suspension of 403 mg of 3-(1H-indol-2-yl)-1H-indazol-5-ol and 268 μl of 1,8-diazabicyclo[5.4.0]undec-7-ene in 12 ml of dichloromethane is added dropwise. The reaction medium is stirred at ambient temperature overnight and then evaporated to dryness under reduced pressure in a rotary evaporator. The reaction crude is purified by flash chromatography on a cartridge of 50 g of silica 15-35 μm. 300 mg of methylphenylphosphinic acid 3-(1H-indol-2-yl)-1H-indazol-5-yl ester are collected and recrystallized from ethyl acetate to obtain 220 mg of methylphenylphosphinic acid 3-(1H-indol-2-yl)-1H-indazol-5-yl ester.

$^1$H NMR spectrum (300 MHz, (CD$_3$)$_2$SO d6, δ in ppm): 1.95 (d, J=14.5 Hz: 3H); 6.87 (broad s: 1H); 7.04 (split t, J=7.5 and 1 Hz: 1H); 7.13 (split t, J=7.5 and 1 Hz: 1H); 7.26 (broad dd, J=8.5 and 2 Hz: 1H); 7.46 (broad d, J=8.5 Hz: 1H); from 7.50 to 7.70 (mt: 5H); 7.81 (mt: 1H); 7.97 (ddd, J=12-8 and 2 Hz: 2H); 11.57 (unresolved peak: 1H); from 13.00 to 13.70 (broad unresolved peak: 1H).

Example 4

Diphenylphosphinic acid 3-(1H-indol-2-yl)-1H-indazol-5-yl ester

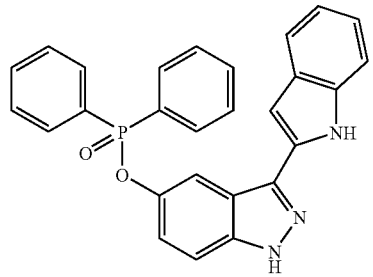

3-(1-tert-Butoxycarbonyl-2,3-dihydro-1H-indol-2-yl)-5-hydroxyindazole-1-carboxylic acid tert-butyl ester is prepared, according to procedure D, using 800 mg of 5-benzyloxy-3-(1-tert-butoxycarbonyl-1H-indol-2-yl)indazole-1- carboxylic acid tert-butyl ester, 560 mg of ammonium formate, and 800 mg of 10% palladium-on-charcoal in 30 ml of absolute ethanol. 700 mg of 3-(1-tert-butoxycarbonyl-2,3-dihydro-1H-indol-2-yl)-5-hydroxyindazole-1-carboxylic acid tert-butyl ester are obtained.

$^1$H NMR spectrum (300 MHz, (CD$_3$)$_2$SO d6, δ in ppm): 1.20 (unresolved peak: 9H); 1.63 (s: 9H); 3.09 (broad dd, J=16.5 and 5 Hz: 1H); 3.79 (dd, J=16.5 and 11 Hz: 1H); 5.79 (dd,J=11 and5 Hz: 1H); 6.62 (d, J=2 Hz: 1H); from 6.95 to 7.10 (mt: 2H); from 7.20 to 7.35 (mt: 2H); 7.81 (unresolved peak: 1H); 7.91 (d, J=9 Hz: 1H); 9.57 (unresolved peak: 1H).

Preparation of 3-(1-tert-butoxycarbonyl-2,3-dihydro-1H-indol-2-yl)-5-(diphenyl-phosphinoyloxy)indazole-1-carboxylic acid tert-butyl ester:

90 mg of imidazole and 250 μl of diphenylphosphinyl chloride are added to a solution of 140 mg of 3-(1-tert-butoxycarbonyl-2,3-dihydro-1H-indol-2-yl)-5-hydroxyindazole-1-carboxylic acid tert-butyl ester in 15 ml of dichloromethane. The reaction medium is stirred at ambient temperature overnight. After dilution with 10 ml of dichloromethane and 10 ml of distilled water, the medium is separated by settling out. The organic phase is dried over magnesium sulfate, filtered, and concentrated under reduced pressure in a rotary evaporator. The crude is taken up in a dichloromethane/methanol mixture and the solid is filtered off. After concentration under reduced pressure, the filtrate is purified by flash chromatography, eluent: cyclohexane/ethyl acetate 8:2 to obtain 200 mg of 3-(1-tert-butoxycarbonyl-2,3-dihydro-1H-indol-2-yl)-5-(diphenylphosphinoyloxy)indazole-1-carboxylic acid tert-butyl ester.

Analytical LC/MS: [M+H]$^+$=652.14; retention time: 4.74 min.

Preparation of diphenylphosphinic acid 3-(2,3-dihydro-1H-indol-2-yl)-1H-indazol-5-yl ester:

A solution of 200 mg of 3-(1-tert-butoxycarbonyl-2,3-dihydro-1H-indol-2-yl)-5-(diphenylphosphinoyloxy)indazole-1-carboxylic acid tert-butyl ester in 4 ml of dioxane and 1 ml of a 4M hydrochloric acid solution in dioxane is stirred at ambient temperature. After 1 hour, 1 ml of a 4M hydrochloric acid solution in dioxane is added. The reaction medium is stirred overnight at ambient temperature. The suspension is filtered through sintered glass. The solid is rinsed with ethyl ether. The solid is taken up in 200 ml of dichloromethane and 8 ml of a 2N aqueous sodium hydroxide solution. The solution is stirred for a few minutes and is then separated by settling out. The organic phase is dried over magnesium sulfate, filtered, and concentrated under reduced pressure to obtain 114 mg of diphenylphosphinic acid 3-(2,3-dihydro-1H-indol-2-yl)-1H-indazol-5-yl ester.

Analytical LC/MS: [M+H]$^+$=452.20; retention time: 3.35 min.

Preparation of diphenylphosphinic acid 3-(1H-indol-2-yl)-1H-indazol-5-yl ester:

170 mg of diphenylphosphinic acid 3-(2,3-dihydro-1H-indol-2-yl)-1H-indazol-5-yl ester are stirred for 10 hours at 100° C. in dimethyl sulfoxide. The solvent is evaporated off under reduced pressure at 30° C. The reaction crude is purified by flash chromatography on silica (8 g Interchim cartridge), eluent: cyclohexane/ethyl acetate 4:6, 2:8; and ethyl acetate/methanol 9:1 to obtain 23 mg of diphenylphosphinic acid 3-(1H-indol-2-yl)-1H-indazol-5-yl ester.

$^1$H NMR spectrum (300 MHz, (CD$_3$)$_2$SO d6, δ in ppm): 6.90 (broad s:1H); 7.04 (broad t, J=7.5 Hz: 1H); 7.13 (broad t, J=7.5 Hz: 1H); 7.45 (mt: 2H); from 7.50 to 7.70 (mt: 8H); 7.99 (mt: 1H); 8.02 (broad dd, J=12 and 7.5 Hz: 4H); 11.57 (unresolved peak: 1H); from 13.00 to 13.70 (unresolved peak: 1H).

Analytical LC/MS : [M+H]$^+$=450.19; retention time: 4.06 min.

Intermediate C, 3-[1-tert-butoxycarbonyl-5-(2-morpholin-4-ylethoxy)-1H-indol-2-yl]-5-hydroxyindazole-1-carboxylic acid tert-butyl ester can be prepared in 5 stages, according to scheme 3.

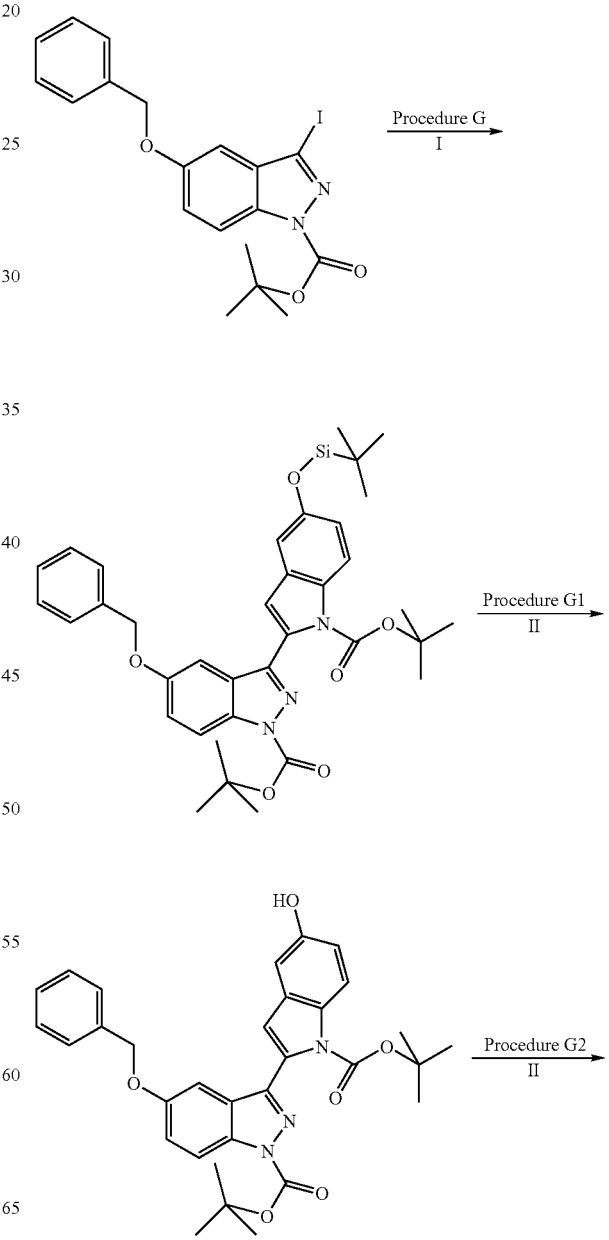

Scheme 3

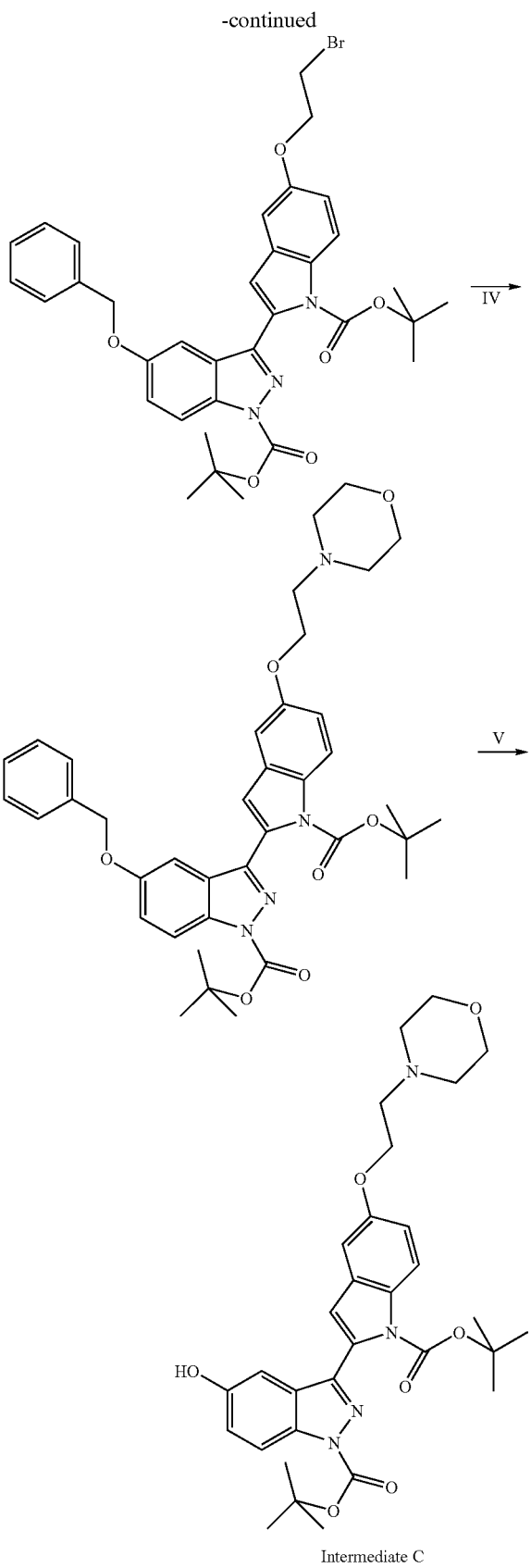

Intermediate C

Stage I: Procedure G

Preparation of 5-benzyloxy-3-(1-tert-butoxycarbonyl-5-tert-butylsilanyloxy-1H-indol-2-yl)-indazole-1-carboxylic acid tert-butyl ester:

13 g of 1-(tert-butyldimethylsilyloxy)-5-indole-2-boronic acid, 28.9 g of cesium carbonate, 906.4 mg of palladium (II) [1,1'-bis(diphenylphosphino)ferrocene] dichloride in a complex with dichloromethane and 51 ml of water are added to a solution of 10 g of 5-benzyloxy-3-iodoindazole-1-carboxylic acid tert-butyl ester in 156 ml of dioxane. The medium is stirred and heated at 88° C. for 45 minutes and then cooled to ambient temperature. The reaction mixture is then separated by settling out, and the organic phase is evaporated under reduced pressure in a rotary evaporator. The reaction crude is solubilized with 250 ml of dichloromethane, and the solution obtained is then washed with 3 times 50 ml of water. The pH of the aqueous washes changes from 11 to 7.

After drying of the organic phase, over magnesium sulfate, the solvent is evaporated off under reduced pressure in a rotary evaporator. The reaction crude is purified by flash chromatography (silica 40-63 μm), eluent: cyclohexane/dichloromethane 40:60 to obtain 13.4 g of 5-benzyloxy-3-(1-tert-butoxycarbonyl-5-tert-butylsilanyloxy-1H-indol-2-yl)indazole-1-carboxylic acid tert-butyl ester.

$^1$H NMR spectrum (300 MHz, $(CD_3)_2SO$ d6, δ in ppm): 0.26 (s: 6H); 1.02 (s: 9H); 1.17 (s: 9H); 1.67 (s: 9H); 5.16 (broad s: 2H); 7.00 (dd, J=9 and 2.5 Hz: 1H); 7.06 (s: 1H); 7.17 (d, J=2.5 Hz: 1H); from 7.30 to 7.50 (mt: 3H); 7.32 (d, J=2.5 Hz: 1H); 7.38 (dd, J=9 and 2.5 Hz: 1H); 7.47 (broad d, J=7.5 Hz: 2H); 8.08 (d, J=9 Hz: 2H).

Stage II: Procedure G1 Preparation of 5-benzyloxy-3-(1-tert-butoxycarbonyl-5-hydroxy-1H-indol-2-yl)indazole-1-carboxylic acid tert-butyl ester:

6.15 g of tetrabutylammonium fluoride are added to a solution of 13.4 g of 5-benzyloxy-3-(1-tert-butoxycarbonyl-5-tert-butylsilanyloxy-1H-indol-2-yl)-indazole-1-carboxylic acid tert-butyl ester in 140 ml of tetrahydrofuran. The medium is stirred for 30 minutes at ambient temperature. The reaction crude is washed with 3 times 25 ml of water, the organic phase is then dried over magnesium sulfate and then filtered, and the solvent is evaporated off under reduced pressure in a rotary evaporator. 14.4 g of crude product are obtained, which are purified by flash chromatography (silica 40-63 μm), eluent: dichloromethane/methanol 98:2 to obtain 8.54 g of 5-benzyloxy-3-(1-tert-butoxycarbonyl-5-hydroxy-1H-indol-2-yl)-indazole-1-carboxylic acid tert-butyl ester.

LC/MS: $[M+H]^+$=556.35; retention time: 4.76 minutes.

Stage III: Procedure G2 Preparation of 5-benzyloxy-3-[5-(2-bromoethoxy)-1-tert-butoxycarbonyl-1H-indol-2-yl]indazole-1-carboxylic acid tert-butyl ester.

A suspension of 2.22 g of 5-benzyloxy-3-(1-tert-butoxycarbonyl-5-hydroxy-1H-indol-2-yl)indazole-1-carboxylic acid tert-butyl ester and of 3.90 g of cesium carbonate in 22 ml of 1,2-dibromoethane is heated at 80° C. for 40 hours and then cooled to ambient temperature and evaporated under reduced pressure. The reaction crude is purified by flash chromatography (silica 40-63 μm), eluent: dichloromethane; 2 g of 5-benzyloxy-3-[5-(2-bromoethoxy)-1-tert-butoxycarbonyl-1H-indol-2-yl]-indazole-1-carboxylic acid tert-butyl ester are isolated.

$^1$H NMR spectrum (300 MHz, (CD$_3$)$_2$SO d6, δ in ppm): 1.17 (s: 9H); 1.67 (s: 9H); 3.85 (broad t, J=5.5 Hz: 2H); 4.41 (broad t, J=5.5 Hz: 2H); 5.16 (s: 2H); 7.07 (s: 1H) 7.11 (dd, J=9 and 2.5 Hz: 1H); 7.29 and 7.30 (2d, J=2.5 Hz: 2H in total); from 7.30 to 7.50 (mt: 6H); 8.08 and 8.11 (2d, J=9 Hz : 2H in total).

LC/MS: [M+H]$^+$=664.22; retention time: 5.67 minutes.

Stage IV: Preparation of 5-benzyloxy-3-[1-tert-butoxycarbonyl-5-(2-morpholin-4-ylethoxy)-1H-indol-2-yl]indazole-1-carboxylic acid tert-butyl ester A suspension of 2.0 g of 5-benzyloxy-3-[5-(2-bromoethoxy)-1-tert-butoxycarbonyl-1H-indol-2-yl]indazole-1-carboxylic acid tert-butyl ester and of 498 mg of potassium iodide in 90 ml of acetonitrile is heated at 80° C. for 7 hours. 394 μl of morpholine, 150 mg of potassium iodide and 1.24 g of potassium carbonate are then added and the mixture is heated at 80° C. for 15 hours. The reaction mixture is cooled to ambient temperature and then filtered. The filtrate is evaporated under reduced pressure in a rotary evaporator to obtain 1.90 g of 5-benzyloxy-3-[1-tert-butoxycarbonyl-5-(2-morpholin-4-ylethoxy)-1H-indol-2-yl]indazole-1-carboxylic acid tert-butyl ester.

LC/MS: [M+H]$^+$=669.43; retention time: 3.99 minutes.

Stage V: Preparation of 3-[1-tert-butoxycarbonyl-5-(2-morpholin-4-ylethoxy)-1H-indol-2-yl]-5-hydroxyindazole-1-carboxylic acid tert-butyl ester.

A solution of 740 mg of 5-benzyloxy-3-[1-tert-butoxycarbonyl-5-(2-morpholin-4-ylethoxy)-1H-indol-2-yl]indazole-1-carboxylic acid tert-butyl ester, of 328 mg of ammonium formate and of 234 mg of 10% palladium-on-charcoal in 56 ml of ethanol is heated at 70° C. for 35 minutes. The reaction mixture is then cooled to ambient temperature. The catalyst is filtered through paper and washed abundantly with ethanol to obtain 533 mg of the crude compound 3-[1-tert-butoxycarbonyl-5-(2-morpholin-4-ylethoxy)-1H-indol-2-yl]-5-hydroxyindazole-1-carboxylic acid tert-butyl ester.

LC/MS: [M+H]$^+$=579.32; retention time: 3.92 minutes.

Preparation of 3-[1-tert-butoxycarbonyl-5-(2-morpholin-4-ylethoxy)-1H-indol-2-yl]-5-(methylphenylphosphinoyloxy)indazole-1-carboxylic acid tert-butyl ester.

16 mg of imidazole and 40.5 mg of methylphenylphosphinic chloride are added to a solution of 27 mg of 3-[1-tert-butoxycarbonyl-5-(2-morpholin-4-yl-ethoxy)-1H-indol-2-yl]-5-hydroxyindazole-1-carboxylic acid tert-butyl ester in 2 ml of dichloromethane. The solution obtained is stirred at ambient temperature. After stirring for 15 hours, a further 16 mg of imidazole and 40.5 mg of methylphenylphosphinic chloride are added and the mixture is stirred at ambient temperature for another 3½ hours in order for the reaction to be complete. The reaction mixture is then filtered and evaporated under reduced pressure in a rotary evaporator. The residue obtained is purified by LC/MS to obtain 10.5 mg of 3-[1-tert-butoxycarbonyl-5-(2-morpholin-4-ylethoxy)-1H-indol-2-yl]-5-(methylphenylphosphinoyloxy)indazole-1-carboxylic acid tert-butyl ester.

LC/MS: [M+H]$^+$=717.41; retention time: 3.61 minutes.

Example 5

Methylphenylphosphinic acid 3-[5-(2-morpholin-4-ylethoxy)-1H-indol-2-yl]-1H-indazol-5-yl ester

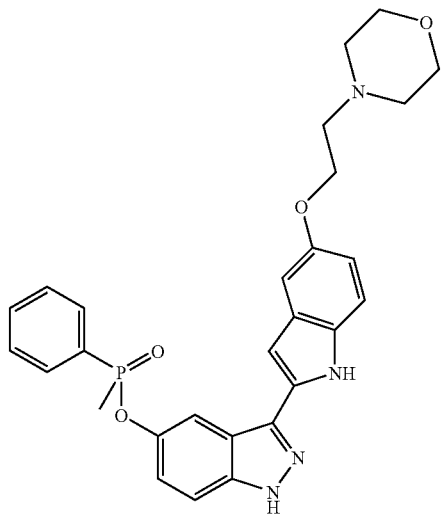

A solution of 10.5 mg of 3-[1-tert-butoxycarbonyl-5-(2-morpholin-4-ylethoxy)-1H-indol-2-yl]-5-(methylphenylphosphinoyloxy)indazole-1-carboxylic acid tert-butyl ester in a mixture of 500 μl of dichloromethane and 500 μl of trifluoroacetic acid is agitated at ambient temperature for 4 hours. The reaction medium is evaporated under a stream of nitrogen and then redissolved in 1.4 ml of DMSO. The solution obtained is stirred at 60° C. for 3 days and then purified by LC/MS to obtain 5.1 mg of methylphenylphosphinic acid 3-[5-(2-morpholin-4-ylethoxy)-1H-indol-2-yl]-1H-indazol-5-yl ester.

LC/MS: [M+H]$^+$=517.35; retention time: 2.64 minutes.

Example 6

Phenylphosphonic acid 3-(1H-indol-2-yl)-1-H-indazol-5-yl ester methyl ester

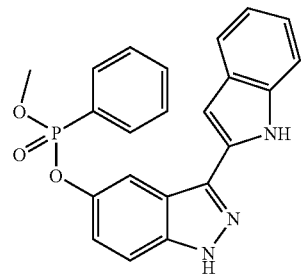

Stage I: Phenylphosphonic acid bis-(4-nitrophenyl) ester is prepared according to procedure E using 0.345 g of sodium hydride in 3 ml of anhydrous tetrahydrofuran and a solution of 1 g of 4-nitrophenol in 5 ml of tetrahydrofuran and of 0.701 g of phenylphosphinic dichloride. 1.46 g of phenylphosphonic acid bis-(4-nitrophenyl) ester are obtained.

Stage II: Phenylphosphonic acid 3-(1H-indol-2-yl)-1H-indazol-5-yl ester methyl ester is prepared according to procedure F using 230 mg of phenyl-phosphonic acid bis-(4-nitrophenyl) ester in solution in 4 ml of dichloromethane to which is added a solution of 120 mg of 3-(1H-indol-2-yl)-1H-indazol-5-ol and 72 μl of 1,8-diazabicyclo[5.4.0]undec-7-ene in 4 ml of dichloromethane. After stirring for 2 hours at ambient temperature, the medium is treated with 4 times 50 ml of a saturated sodium bicarbonate solution, and then with 2×50 ml of a saturated sodium chloride solution. The organic phase is dried over magnesium sulfate and then concentrated to dryness to obtain 200 mg of crude phenylphosphonic acid 3-(1H-indol-2-yl)-1H-indazol-5-yl ester methyl ester.

Stage III: Phenylphosphonic acid 3-(1H-indol-2-yl)-1H-indazol-5-yl ester methyl ester is prepared according to procedure F using 200 mg of crude phenylphosphonic acid 3-(1H-indol-2-yl)-1H-indazol-5-yl ester methyl ester in 4 ml of dichloromethane, 95 μl of methanol, 72 μl of 1,8-diazabicyclo[5.4.0]undec-7-ene and 4 ml of dichloromethane. After concentration under reduced pressure in a rotary evaporator, the crude is purified on an 8 g interchim flash cartridge of silica with a particle size of 15-35 μm. The product is eluted with a gradient of 15 to 50% of ethyl acetate in cyclohexane. 70 mg of an impure product are obtained and repurified by preparative LCMS. The product obtained in solution is concentrated to dryness in a Jouan RC1010 evaporator to obtain 34 mg of phenylphosphonic acid 3-(1H-indol-2-yl)-1H-indazol-5-yl ester methyl ester in the form of a yellow solid.

$^1$H NMR spectrum (300 MHz, $(CD_3)_2SO$ d6, δ in ppm): 3.86 (d, J=11 Hz: 3H); 6.93 (broad s: 1H); 7.04 (broad t, J=7,5 Hz: 1H); 7.13 (broad t J=7.5 Hz: 1H); 7.31 (broad d, J=9 Hz: 1H); 7.46 (broad d, J=7.5 Hz: 1H); from 7.55 to 7.65 (mt: 4H); 7.73 (very broad t, J=7.5 Hz: 1H); 7.86 (broad s: 1H); 7.93 (broad dd, J=13.5 and 7.5 Hz: 2H); 11.59 (unresolved peak: 1H); 13.41 (unresolved peak: 1H).

Analytical LC/MS: $[M+H]^+$=404.19; retention time: 3.62 minutes.

Example 7

Phenylphosphonic acid 3-(1H-indol-2-yl)-1H-indazol-5-yl ester isopropyl ester

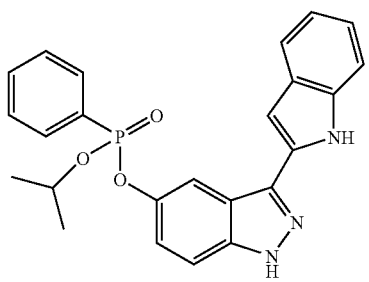

Phenylphosphonic acid 3-(1H-indol-2-yl)-1H-indazol-5-yl ester isopropyl ester is prepared according to procedure F using 100 mg of crude phenyl-phosphonic acid bis-(4-nitrophenyl) ester in solution in 5 ml of dichloromethane, 150 pl of isopropanol and 30 μl of 1,8-diazabicyclo[5.4.0]undec-7-ene. After concentration of the reaction medium, the crude is purified by preparative LC/MS to obtain 21.5 mg of the title compound.

$^1$H NMR spectrum (300 MHz, $(CD_3)_2SO$ d6, δ in ppm): 1.29 (d, J=6 Hz: 3H); 1.33 (d, J=6 Hz: 3H); 4.84 (mt: 1H); 6.90 (d, J=1.5 Hz: 1H); 7.04 (broad t, J=7.5 Hz: 1H); 7.14 (broad t, J=7.5 Hz: 1H); 7.30 (broad dd, J=8.5 and 1.5 Hz: 1H); 7.46 (d, J=8.5 Hz: 1H); from 7.50 to 7.65 (mt: 4H); 7.70 (mt: 1H); 7.86 (broad s: 1H); 7.91 (mt: 2H); 11.58 (broad s: 1H); 13.39 (broad s: 1H).

Example 8

Phenylphosphonic acid 3-(1H-indol-2-yl)-1H-indazol-5-yl ester benzyl ester

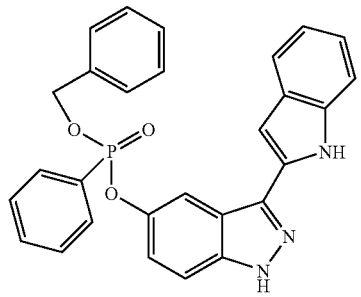

Phenylphosphonic acid 3-(1H-indol-2-yl)-1H-indazol-5-yl ester benzyl ester is prepared according to procedure F using 150 mg of phenyl-phosphonic acid 3-(1H-indol-2-yl)-1H-indazol-5-yl ester 4-nitrophenyl ester (prepared according to procedure F) in solution in 2 ml of dichloromethane stabilized with amylene, 310 μl of benzyl alcohol and 44 μl of 1,8-diazabicyclo[5.4.0]undec-7-ene. The reaction crude is purified by preparative LC/MS to obtain 16.9 mg of phenylphosphonic acid 3-(1H-indol-2-yl)-1-indazol-5-yl ester benzyl ester.

$^1$H NMR spectrum (300 MHz, $(CD_3)_2SO$ d6, δ in ppm): 5.28 (d, J=8 Hz: 2H); 6.87 (d, J=1.5 Hz: 1H); 7.04 (broad t, J=7.5 Hz: 1H); 7.14 (broad t, J=7.5 Hz: 1H); from 7.20 to 7.75 (mt: 12H); 7.86 (broad s: 1H); 7.94 (mt: 2H); 11.58 (broad s: 1H); 13.40 (broad s: 1H).

Example 9

Methylphosphonic acid 3-(1H-indol-2-yl)-1H-indazol-5-yl ester methyl ester

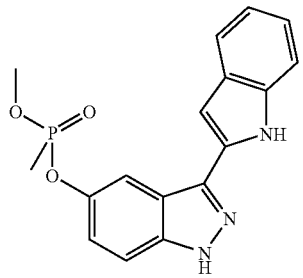

Stage I: Methylphosphonic acid bis-(4-nitrophenyl) ester is prepared according to procedure E using 1 g of 4-nitrophenol, 12 ml of THF, 345 mg of sodium hydride at 50% in oil and 478 mg of methylphosphonic dichloride. 1.07 g of crude methylphosphonic acid bis-(4-nitrophenyl) ester are obtained.

Stage II: Methylphosphonic acid 3-(1H-indol-2-yl)-1H-indazol-5-yl ester methyl ester is prepared according to procedure F using 150 mg of methylphosphonic acid bis-(4-nitrophenyl) ester, 4 ml of dichloromethane, 100 mg of 3-(1H-indol-2-yl)-1H-indazol-5-ol, 67 µl of 1,8-diazabicyclo [5.4.0]undec-7-ene and 4 ml of dichloromethane. After stirring for 3 hours, a solution of 100 µl of methanol in 2 ml of dichloromethane is added dropwise. The reaction medium is stirred for approximately 16 hours and then concentrated to dryness under reduced pressure. The oil obtained is purified on a 5 g Interchim flash cartridge of silica with a particle size of 15-35 µ. Eluent: 30% of ethyl acetate in cyclohexane, then with 80% of ethyl acetate in methanol. The solvents are evaporated off under reduced pressure and the product obtained is crystallized from ethyl acetate. 36 mg of methylphosphonic acid 3-(1H-indol-2-yl)-1H-indazol-5-yl ester methyl ester are obtained in the form of white crystals.

$^1$H NMR spectrum (300 MHz, (CD$_3$)$_2$SO d6, δ in ppm): 1.72 (d, J=17.5 Hz: 3H); 3.80(d, J=11 Hz: 3H); 7.04 (broad t,J=7.5 Hz: 1H); 7.07 (broad s: 1H); 7.13 (broad t, J=7.5 Hz: 1H); 7.35 (broad d, J=9 Hz: 1H); 7.47 (broad d, J=7.5 Hz: 1H); 7.63 (broad d, J=7.5 Hz: 1H); 7.65 (d, J=9 Hz: 1H); 7.95 (broad s: 1H); 11.59 (unresolved peak: 1H).

Example 10

Phenylphosphonic acid 1H-indazol-5-yl ester methyl ester

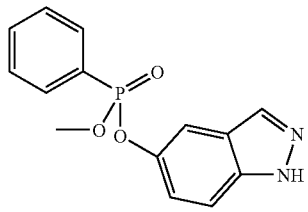

Stage I: Preparation of 1-(5-hydroxyindazol-1-yl)ethanone. A suspension of 939 mg of 1-(5-benzyloxyindazol-1-yl)ethanone, 1.33 g of ammonium formate and 939 mg of palladium-on-charcoal at 10% in 100 ml of absolute ethanol is heated at around 50° C. for about thirty minutes. When gas is no longer being given off, the catalyst is filtered through a paper filter and rinsed with absolute ethanol. The filtrate is concentrated under reduced pressure in a rotary evaporator to obtain 571.1 mg of 1-(5-hydroxyindazol-1-yl)ethanone.

$^1$H NMR spectrum (300 MHz, (CD$_3$)$_2$SO d6, δ in ppm): 2.69 (s: 3H); 7.11 (dd, J=9 and 2 Hz: 1H); 7.14 (d, J=2 Hz: 1H); 8.15 (d, J=9 Hz: 1H); 8.31 (d, J=1 Hz: 1H); from 9.40 to 9.90 (broad unresolved peak: 1H).

Stage II: Preparation of phenylphosphonic acid 1-acetyl-1H-indazol-5-yl ester 4-nitrophenyl ester according to procedure F using 200 mg of phenyl-phosphonic acid bis-(4-nitrophenyl) ester, 88 mg of 1-(5-hydroxyindazol-1-yl)-ethanone, 74.7 µl of 1,8-diazabicyclo[5.4.0]undec-7-ene and 8 ml of dichloromethane. After washing the organic phase with a 0.1M sodium bicarbonate solution, drying over magnesium sulfate, filtration and concentration under reduced pressure in a rotary evaporator, 219 mg of crude phenylphosphonic acid 1-acetyl-1H-indazol-5-yl ester 4-nitrophenyl ester are collected and used without purification in the subsequent step.

Stage III: Phenylphosphonic acid 1H-indazol-5-yl ester methyl ester is prepared according to procedure F using 219 mg of phenyl-phosphonic acid 1-acetyl-1H-indazol-5-yl ester 4-nitrophenyl ester, 5 ml of dichloromethane, 74.8 µl of 1,8-diazabicyclo[5.4.0]undec-7-ene and 202 µl of methanol. The crude is purified by flash chromatography on silica with a particle size of 35-70 µm. Eluent: cyclohexane then 80:20 cyclohexane/ethyl acetate to obtain 15 mg of phenylphosphonic acid 1H-indazol-5-yl ester methyl ester in the form of a colorless oil.

$^1$H NMR spectrum (300 MHz, (CD$_3$)$_2$SO d6, δ in ppm): 3.82 (d, J=11 Hz: 3H); 7.19 (broad dd, J=9 and 2.5 Hz: 1H); from 7.50 to 7.75 (mt: 4H); 7.53 (broad d, J=9 Hz: 1H); 7.86 (broad dd, J=13.5 and 8 Hz: 2H); 8.05 (broad s: 1H); 13.13 (unresolved peak: 1H).

IR (CCl$_4$): 3232; 3064; 2953; 1500; 1440; 1247; 1133; 1044; 964; 943; 907; 693 and 559 cm$^{-1}$.

Analytical LC/MS: [M+H]$^+$=289.18; retention time: 2.84 minutes

3-Iodo-5-(methoxyphenylphosphinoyloxy)indazole-1-carboxylic acid tert-butyl ester, intermediate D is next prepared starting from phenylphosphonic acid 1H-indazol-5-yl ester methyl ester (Example 10) as follows:

Stage IV: Phenylphosphonic acid 3-iodo-1H-indazol-5-yl ester methyl ester is prepared according to procedure A using 76 mg of phenylphosphonic acid 1H-indazol-5-yl ester methyl ester, 134 mg of iodine and 30.6 mg of potassium hydroxide ground beforehand in 3 ml of dimethylformamide. The crude is purified by flash chromatography on silica with a particle size of 15-35 µm. Eluent: ethyl acetate/cyclohexane 1:1 to obtain 77.6 mg of phenyl-phosphonic acid 3-iodo-1H-indazol-5-yl ester methyl ester.

$^1$H NMR spectrum (300 MHz, (CD$_3$)$_2$SO d6, δ in ppm): 3.83 (d, J=11 Hz: 3H); 7.19 (t, J=2 Hz: 1H); 7.27 (ddd, J=9-2 and 1 Hz: 1H); from 7.50 to 7.65 (mt: 2H); 7.56 (d, J=9 Hz: 1H); 7.72 (tq, J=7.5 and 2 Hz: 1H); 7.88 (ddd, J=13.5-7.5 and 1.5 Hz: 2H); from 13.20 to 13.90 (broad unresolved peak: 1H).

IR (CH$_2$Cl$_2$): 3444; 3184; 2853; 1494; 1440; 1165; 1133; 1045; 958; 906; 817 and 559 cm$^{-1}$.

Analytical LC/MS: [M+H]$^+$=415.04; retention time: 3.24 minutes

Stage V: 3-Iodo-5-(methoxyphenylphosphinoyloxy)indazole-1-carboxylic acid tert-butyl ester, intermediate D, is prepared according to procedure B using 77.6 mg of phenylphosphonic acid 3-iodo-1H-indazol-5-yl ester methyl ester, 122.7 mg of di-tert-butyl dicarbonate, 78.1 µl of triethylamine and 5.7 mg of 4-dimethylaminopyridine in solution in 2.4 ml of dichloromethane. The reaction crude is purified by flash chromatography on silica with a particle size of 15-35 µm. Eluent: cyclohexane/ethyl acetate 80:20, then 50:50 to obtain 66.3 mg of 3-iodo-5-(methoxyphenylphosphinoyloxy)indazole-1-carboxylic acid tert-butyl ester.

Analytical LC/MS: [M+H]$^+$=515.02; retention time: 4.13 minutes.

3-(1-Tert-butoxycarbonyl-1H-pyrrol-2-yl)-5-(methoxyphenylphosphinoyloxy)indazole-1-carboxylic acid tert-butyl ester is prepared according to procedure G using 66.34 mg of 3-iodo-5-(methoxyphenylphosphinoyloxy)-indazole-1-carboxylic acid tert-butyl ester, 54.44 mg of 2-pyrrole-1-(tert-butoxycarbonyl) boronic acid, 5.28 mg of 1,1'-bis(diphenylphosphino)ferrocene palladium(II) dichloride, 168 mg of cesium carbonate, 328 µl of water and 1 ml of dioxane. The crude is purified by flash chromatography on silica with a particle size of 15-35 µm. Eluent: ethyl acetate/cyclohexane 20:80 then 30:70 to obtain 35.3 mg of 3-(1-tert-butoxycarbonyl-1H-pyrrol-2-yl)-5-(methoxyphenyl-phosphinoyloxy)indazole-1-carboxylic acid tert-butyl ester are recovered.

Analytical LC/MS: [M+H]$^+$=554.18; retention time: 4.42 minutes.

Example 11

Phenylphosphonic acid methyl ester 3-(1H-pyrrol-2-yl)-1H-indazol-5-yl ester

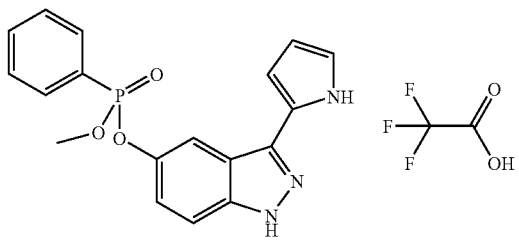

39 mg of 3-(1-tert-butoxycarbonyl-1H-pyrrol-2-yl)-5-(methoxyphenyl-phosphinoyloxy)indazole-1-carboxylic acid tert-butyl ester are dissolved in 0.5 ml of dichloromethane and then 0.5 ml of trifluoroacetic acid is added. The solution is stirred at ambient temperature for approximately two hours. The solvent is evaporated off under reduced pressure in a rotary evaporator. The reaction crude is purified by preparative LC/MS to obtain 19 mg of phenylphosphonic acid methyl ester 3-(1H-pyrrol-2-yl)-1H-indazol-5-yl ester as a trifluoroacetate salt.

$^1$H NMR spectrum (300 MHz, (CD$_3$)$_2$SO d6, δ in ppm): 3.84 (d, J=11.5 Hz: 3H); 6.20 (q, J=3 Hz: 1H); 6.52 (mt: 1H); 6.83 (mt: 1H); 7.24 (ddd, J=9-2.5 and 1.5 Hz: 1H); 7.51 (d, J=9 Hz: 1H); from 7.50 to 7.65 (mt: 2H); from 7.65 to 7.75 (mt: 2H); 7.89 (ddd, J=13.5-8 and 1.5 Hz: 2H); 11.33 (broad s: 1H); 13.02 (broad s: 1H).

Analytical LC/MS: [M+H]$^+$=354.19; retention time: 3.23 minutes

Example 12

[3-((E)-styryl)-1H-indazol-5-yl]phosphonic acid dimethyl ester

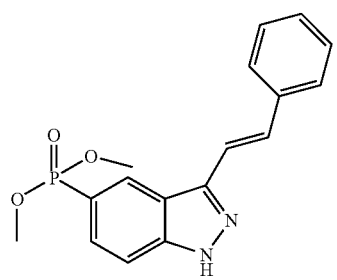

Trifluoromethanesulfonic acid 3-((E)-styryl)-1H-indazol-5-yl ester is prepared in one stage, according to scheme 4:

Scheme 4

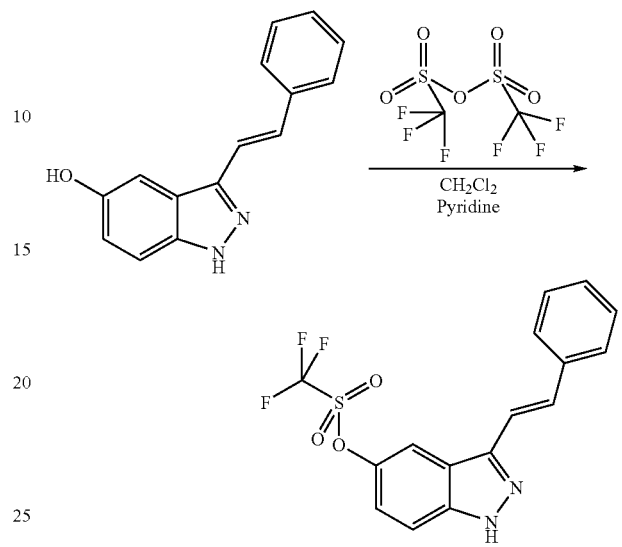

171 µl of trifluoromethanesulfonic anhydride, followed by 512 µl of pyridine, are added dropwise to a solution of 200 mg of 3-((E)-styryl)-1H-indazol-5-ol in 20 ml of dichloromethane on amylene, pre-cooled to 0° C. The medium is stirred and kept at 0° C. for 4 hours, and then left at ambient temperature for an entire weekend, with stirring. The reaction mixture is then washed with 2 times 20 ml of water. The aqueous phase is extracted with 3 times 30 ml of dichloromethane. The organic phase is dried over magnesium sulfate and then filtered and the solvent is evaporated off under reduced pressure in a rotary evaporator, with 10 ml of toluene being added to obtain 343.8 mg of crude product.

LC/MS: [M+H]$^+$=369.13; retention time=4.98 minutes.

Procedure H according to scheme 5:

Scheme 5

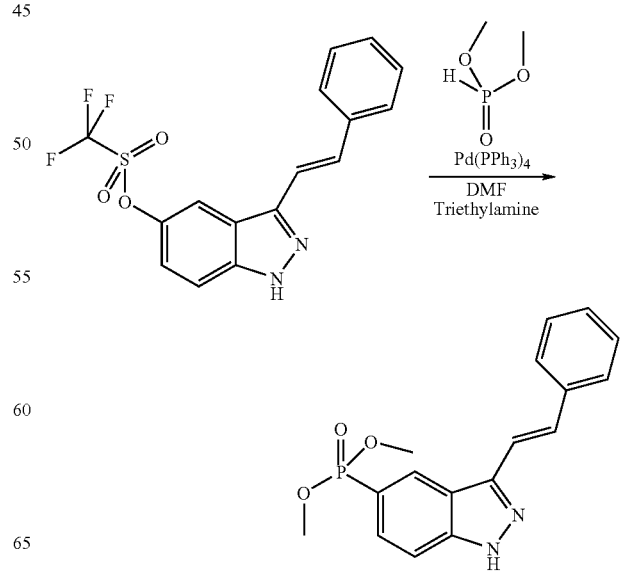

40.7 µl (1.09 eq; 0.444 mmol) of dimethyl phosphite, 61.9 µl (1.09 eq; 0.444 mmol) of triethylamine and 18.8 mg (0.04 eq; 0.016 mmol) of tetrakis(triphenylphosphine)palladium (0) are stirred under an argon atmosphere for 15 minutes. 150 mg (1 eq; 0.407 mmol) of trifluoromethanesulfonic acid 3-((E)-styryl)-1H-indazol-5-yl ester in solution in 5 ml of dimethylformamide are added. The medium is heated at 85° C. overnight. 41 µl of dimethylphosphite, 62 µl of triethylamine and 20 mg of tetrakis(triphenylphosphine)palladium (0) are added to the medium, which is heated for a further two hours. 100 µl of dimethylphosphite, 100 µl of triethylamine and 30 mg of tetrakis(triphenylphosphine)palladium(0) are then added to the medium, which is heated overnight at 105° C. After filtration of the catalyst through filter paper, the solvent is evaporated off under reduced pressure in a rotary evaporator. The reaction crude is purified by LC/MS to obtain 8.6 mg of [3-((E)-styryl)-1H-indazol-5-yl]phosphonic acid dimethyl ester, along with 27.2 mg of [3-((E)-styryl)-1H-indazol-5-yl]phosphonic acid monomethyl ester (Example 13).

Analytical data of [3-((E)-styryl)-1H-indazol-5-yl]phosphonic acid dimethyl ester are as follows:

LC/MS: [M+H]$^+$=329.20; retention time: 3.20 minutes.

$^1$H NMR spectrum (300 MHz, (CD$_3$)$_2$SO d6, δ in ppm): 3.71 (d, J=11.5 Hz: 6H); 7.32 (broad t, J=7.5 Hz: 1H); 7.43 (broad t, J=7.5 Hz : 2H); from 7.45 to 7.70 (mt: 4H); 7.78 (broad d, J=7.5 Hz: 2H); 8.57 (d, J=14 Hz: 1H); 13.52 (broad s: 1H).

Analytical data of [3-((E)-styryl)-1H-indazol-5-yl]phosphonic acid monomethyl ester are as follows:

LC/MS: [M+H]$^+$=315.18; retention time: 2.66 minutes.

Example 13

[3-((E)-styryl)-1H-indazol-5-yl]phosphonic acid monomethyl ester

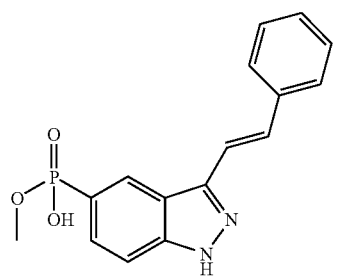

18.5 mg of [3-((E)-Styryl)-1H-indazol-5-yl]phosphonic acid dimethyl ester are dissolved in 500 µl of 1M sodium hydroxide solution in methanol. The medium is stirred at ambient temperature for 4 hours. 100 µl of 2N hydrochloric acid are added to the mixture, which is stirred for 15 min at ambient temperature. The organic phase is extracted with 3 ml of ethyl acetate. The solvent is evaporated off under vacuum in a centrifugal evaporator to obtain 18 mg of the title compound.

$^1$H NMR spectrum (300 MHz, (CD$_3$)$_2$SO d6, δ in ppm): 3.20 (d, J=10.5 Hz: 3H); 7.31 (broad t, J=7.5 Hz: 1H); from 7.35 to 7.50 (mt: 3H); 7.45 (d, J=17 Hz: 1H); 7.58 (d, J=17 Hz: 1H); 7.62 (d, J=9 Hz: 1H); 7.72 (broad d, J=7.5 Hz: 2H); 8.33 (d, J=13 Hz: 1H); 13.10 (unresolved peak: 1H).

LC/MS: [M+H]$^+$=315.18; retention time: 2.73 minutes.

Example 14

[3-((E)-styryl)-1H-indazol-5-yl]phosphonic acid diethyl ester

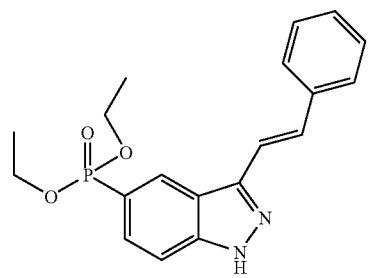

Procedure H is followed, introducing 70 mg (1 eq; 0.190 mmol) of trifluoromethanesulfonic acid 3-((E)-styryl)-1H-indazol-5-yl ester in solution in 3 ml of dimethylformamide, 26.7 µl (1.09 eq; 0.207 mmol) of diethylphosphite, 8.9 mg (0.04 eq-0.0076 mmol) of tetrakis(triphenylphosphine)palladium(0) and 28.8 µl (1.09 eq; 0.207 mmol) of triethylamine. The additions made are successively 27 µl of diethylphosphite, 29 µl of triethylamine, 10 mg of tetrakis(triphenylphosphine)palladium(0), then 50 µl of diethylphosphite, 50 µl of triethylamine, 20 mg of tetrakis(triphenylphosphine)palladium(0) and, finally, 27 µl of diethylphosphite, 29 µl of triethylamine and 9 mg of tetrakis(triphenylphosphine) palladium(0). 22 mg of [3-((E)-styryl)-1H-indazol-5-yl]phosphonic acid diethyl ester are isolated, along with 8.7 mg of [3-((E)-styryl)-1H-indazol-5-yl]phosphonic acid monoethyl ester.

Analytical data of [3-((E)-styryl)-1H-indazol-5-yl]phosphonic acid diethyl ester are as follows:

LC/MS: [M+H]$^+$=357.19; retention time: 3.63 min.

$^1$H NMR spectrum (300 MHz, (CD$_3$)$_2$SO d6, δ in ppm): 1.28 (t, J=7 Hz: 6H); 4.07 (mt: 4H); 7.33 (broad t, J=7.5 Hz: 1H); 7.43 (broad t, J=7.5 Hz: 2H); from 7.45 to 7.75 (mt: 2H); 7.53 (d, J=16.5 Hz: 1H); 7.72 (d, J=16.5 Hz: 1H); 7.78 (broad d, J=7.5 Hz: 2H); 8.56 (d, J=14 Hz: 1H); 13.50 (unresolved peak: 1H).

Analytical data of [3-((E)-styryl)-1H-indazol-5-yl]phosphonic acid monoethyl ester are as follows:

LC/MS: [M+H]$^+$=329.17; retention time: 3.00 minutes.

The reaction intermediate E, 5-(dimethoxyphosphoryl)-3-iodoindazole-1-carboxylic acid tert-butyl ester, is prepared in four stages, according to scheme 6.

Scheme 6

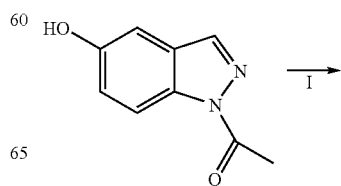

-continued

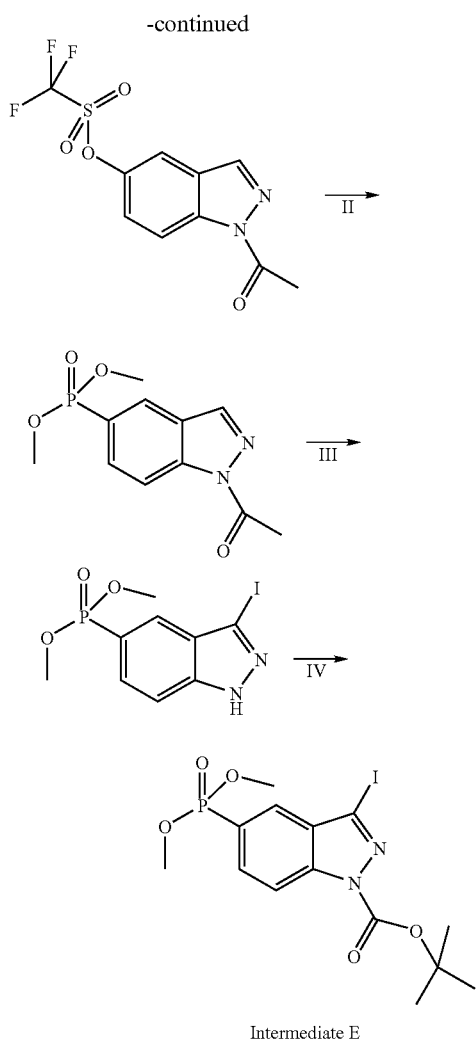

Intermediate E

Stage I: Procedure I Preparation of trifluoromethanesulfonic acid 1-acetyl-1H-indazol-5-yl ester 112 μl (1.2 eq; 0.667 mmol) of trifluoromethanesulfonic anhydride and 337 μl (17.5 eq; 49.557 mmol) of pyridine, under an argon atmosphere, are added dropwise to a solution of 98 mg (1 eq; 0.556 mmol) of 1-(5-hydroxyindazol-1-yl) ethanone in 10 ml of dichloromethane on amylene, precooled to 0° C. The medium is stirred and kept at 0° C. overnight under an argon atmosphere. 112 μl of trifluoromethanesulfonic anhydride and 337 μl of pyridine are added to the medium, which is stirred for 2 hours at 0° C. 112 μl of trifluoromethanesulfonic anhydride and 337 μl of pyridine are then added, and the medium is then stirred for 3 hours at 0° C. The reaction mixture is washed with 10 ml of water. The aqueous phase is treated with 2 times 10 ml of dichloromethane. The organic phase is dried over magnesium sulfate and then filtered and the solvent is evaporated off under reduced pressure in a rotary evaporator to obtain 168.9 mg of trifluoromethanesulfonic acid 1-acetyl-1H-indazol-5-yl ester are obtained.

$^1$H NMR spectrum (300 MHz, $(CD_3)_2SO$ d6, δ in ppm): 2.76 (s: 3H); 7.77 (dd, J=9 and 2.5 Hz: 1H); 8.17 (d, J=2.5 Hz: 1H); 8.47 (d, J=9 Hz: 1H); 8.60 (s: 1H).

Stage II: Preparation of (1-acetyl-1H-indazol-5-yl)phosphonic acid dimethyl ester.

291 μl (1.09 eq; 3.172 mmol) of dimethylphosphite, 442 μl (1.09 eq; 3.172 mmol) of triethylamine and 134 mg (0.04 eq; 0.116 mmol) of tetrakis(triphenylphosphine)palladium(0) are stirred under an argon atmosphere for 15 minutes. 897 mg (1 eq; 2.91 mmol) of trifluoromethanesulfonic acid 1-acetyl-1H-indazol-5-yl ester in solution in 60 ml of dimethylformamide. The medium is heated at 105° C. for 4 hours under an argon atmosphere. The solvent is evaporated off under reduced pressure in a rotary evaporator, with 40 ml of toluene being added. The reaction crude is taken up in 40 ml of ethyl acetate and then washed with 50 ml of water. The organic phase is dried over magnesium sulfate and then filtered and the solvent is evaporated off under reduced pressure in a rotary evaporator. 973.6 mg of crude product are obtained. The reaction crude is purified by flash chromatography (silica 35-70 μm), eluent: ethyl acetate/cyclohexane 80:20 to obtain 430.5 mg of (1-acetyl-1H-indazol-5-yl)phosphonic acid dimethyl ester.

LC/MS: [M+H]$^+$=269.18, retention time: 2.79 min.

Stage III: Preparation of (3-iodo-1H-indazol-5-yl)phosphonic acid dimethyl ester.

814 mg (2 eq-3.206 mmol) of iodine and 180 mg (2 eq-3.206 mmol) of ground potassium hydroxide are added to a solution of 430 mg (1 eq-1.603 mmol) of (1-acetyl-1H-indazol-5-yl)phosphonic acid dimethyl ester in 20 ml of dimethylformamide. The medium is stirred at ambient temperature over a weekend. Another portion of 814 mg of iodine and 180 mg of potassium hydroxide are added to the reaction mixture, which is continued to stir for an additional period of 3 hours at ambient temperature. 20 ml of a saturated sodium thiosulfate solution are added and the medium is stirred for 10 minutes. The reaction mixture is washed with 40 ml of water. The aqueous phase is treated with 4 times 50 ml of ethyl acetate. The organic phase is dried over magnesium sulfate and then filtered and the solvent is evaporated off under reduced pressure in a rotary evaporator to obtain 458 mg of (3-iodo-1H-indazol-5-yl)phosphonic acid dimethyl ester.

LC/MS: [M+H]$^+$=353.06, retention time: 2.65 minutes.

Stage IV: Preparation of 5-(dimethoxyphosphoryl)-3-iodoindazole-1-carboxylic acid tert-butyl ester.

851.7 mg (3 eq; 3.903 mmol) of di-tert-butyl dicarbonate, 39.7 mg (0.25 eq; 0.325 mmol) of 4-dimethylaminopyridine and 544 μl (3 eq; 3.903 mmol) of triethylamine are added to a solution of 458 mg (1 eq; 1.301 mmol) of (3-iodo-1H-indazol-5-yl)phosphonic acid dimethyl ester in solution in 10 ml of dichloromethane. The medium is stirred at ambient temperature overnight. The reaction mixture is washed with 20 ml of water and then 10 ml of a saturated sodium chloride solution. The aqueous phase is treated with 4 times 20 ml of ethyl acetate. The organic phase is dried over magnesium sulfate and then filtered and the solvent is evaporated off under reduced pressure in a rotary evaporator to obtain 415 mg of crude product.

LC/MS: [M+H]$^+$=452.99, retention time: 3.61 minutes.

Example 15

[3-(1H-Indol-2-yl)-1H-indazol-5-yl]phosphonic acid monomethyl ester

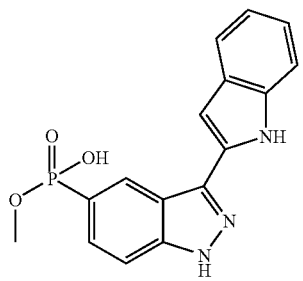

82.9 mg (0.25 eq; 0.072 mmol) of tetrakis(triphenylphosphine)palladium(0), 150.1 mg (2 eq; 0.575 mmol) of 1-boc-indole-2-boronic acid, 5 ml of dimethylformamide and 250 µl of saturated sodium bicarbonate solution are added to 130 mg (1 eq; 0.287 mmol) of 5-(dimethoxyphosphoryl)-3-iodo-indazole-1-carboxylic acid tert-butyl ester. The medium is stirred at 130° C. for 5 hours. The reaction medium is filtered through paper and the solvent is evaporated off under reduced pressure in a rotary evaporator. The reaction crude is purified by LC/MS to obtain 41 mg of [3-(1H-indol-2-yl)-1H-indazol-5-yl]-phosphonic acid monomethyl ester.

$^1$H NMR spectrum (300 MHz, $(CD_3)_2SO$ d6, δ in ppm): 3.58 (d, J=11 Hz: 3H); 7.05 (split t, J=7.5 and 1 Hz: 1H); 7.08 (broad s: 1H); 7.16 (split t, J=7.5 and 1 Hz: 1H); 7.49 (broad d, J=7.5 Hz: 1H); from 7.60 to 7.75 (mt: 2H); 7.67 (broad d, J=7.5 Hz: 1H); 8.51 (d, J=14 Hz: 1H); 11.69 (broad s: 1H); 13.62 (unresolved peak: 1H).

LC/MS: [M+H]$^+$=328.17; retention time: 2.57 minutes.

Example 16

(3-Thiophen-2-yl-1H-indazol-5-yl)phosphonic acid monomethyl ester

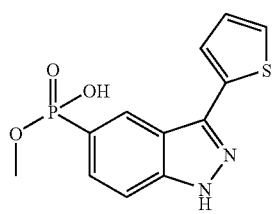

44.8 mg (0.25 eq; 0.039 mmol) of tetrakis(triphenylphosphine)palladium(0), 39.6 mg (2 eq; 0.310 mmol) of 2-thiopheneboronic acid, 3 ml of dimethylformamide and 150 µl of saturated sodium bicarbonate solution are added to 70 mg (1 eq; 0.155 mol) of 5-(dimethoxyphosphoryl)-3-iodoindazole-1-carboxylic acid tert-butyl ester. The medium is stirred at 130° C. for 5 hours. The reaction medium is filtered through paper and the solvent is evaporated off under reduced pressure in a rotary evaporator. The reaction crude is purified by LC/MS to obtain 2 mg of (3-thiophen-2-yl-1H-indazol-5-yl)phosphonic acid dimethyl ester (40% purity by NMR), along with 12.9 mg of (3-thiophen-2-yl-1H-indazol-5-yl) phosphonic acid monomethyl ester.

$^1$H NMR spectrum (300 MHz, $(CD_3)_2SO$ d6, δ in ppm): 3.53 (d, J=11 Hz: 3H); 7.26 (dd, J=5.5 and 3 Hz: 1H); 7.65 (dd, J=5.5 and 1 Hz: 1H); from 7.65 to 7.75 (mt: 2H); 7.68 (broad d, J=3 Hz: 1H); 8.41 (d, J=14 Hz: 1H); 13.49 (unresolved peak: 1H).

Example 17

[3-(1H-Pyrrol-2-yl)-1H-indazol-5-yl]phosphonic acid monomethyl ester

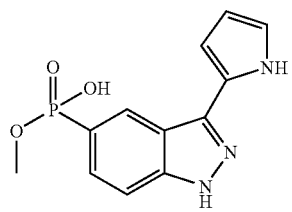

44.8 mg (0.25 eq; 0.039 mmol) of tetrakis(triphenylphosphine)palladium(0), 65.3 mg (2 eq; 0.310 mmol) of 1-boc-pyrrole-2-boronic acid, 3 ml of dimethylformamide and 150 µl of saturated sodium bicarbonate solution are added to 70 mg (1 eq; 0.155 mmol) of 5-(dimethoxyphosphoryl)-3-iodo-indazole-1-carboxylic acid tert-butyl ester. The medium is stirred at 130° C. for 5 hours. The reaction medium is filtered through paper and the solvent is evaporated off under reduced pressure in a rotary evaporator. The reaction crude is purified by LC/MS to obtain 4.10 mg of ([3-(1H-pyrrol-2-yl)-1H-indazol-5-yl]-phosphonic acid monomethyl ester.

$^1$H NMR spectrum (300 MHz, $(CD_3)_2SO$ d6, δ in ppm): 3.55 (d, J=11 Hz: 3H); 6.24 (q, J=3 Hz: 1H); 6.66 (mt: 1H); 6.91 (mt: 1H); 7.65 (mt: 2H); 8.36 (d, J=14.5 Hz: 1H); 11.46 (unresolved peak: 1H); 13.24 (unresolved peak: 1H).

Example 18

Dimethylphosphinic acid 3-(1H-indol-2-yl)-1H-indazol-5-yl ester

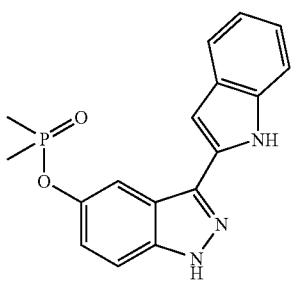

The dimethylphosphinic acid 4-nitrophenyl ester reactant is prepared according to procedure E using 500 mg of dimethylphosphinic chloride, 214 mg of sodium hydride (50% in oil), and 618 mg of p-nitrophenol in solution in 10 ml of tetrahydrofuran. 700 mg of expected product are collected. Yield=26%.

The dimethylphosphinic acid 3-(1H-indol-2-yl)-1H-indazol-5-yl ester compound is prepared according to procedure F using 230 mg of 3-(1H-indol-2-yl)-1H-indazol-5-ol (intermediate B) in solution with 245 mg of dimethylphosphinic acid 4-nitrophenyl ester in 5 ml of dichloromethane (stabilized with amylene) to which 170 μl of 1,8-diazabicyclo[5.4.0]undec-7-ene (DBU) in solution in 2 ml of dichloromethane are added. After stirring for 24 h at ambient temperature, the solvent is evaporated off and the crude is purified by preparative LC/MS. The crystals obtained after concentration of the fractions are washed with ethyl acetate and then with isopropyl ether. 129 mg of expected product are collected. Yield=43%.

NMR spectrum chemical shifts (δ in ppm)—in the solvent dimethyl sulfoxide—d6 (DMSO-d6) referenced at 2.50 ppm:

1.65 (d, J=15.0 Hz, 6H); from 7.00 to 7.06 (m, 2H); 7.13 (broad t, J=8.0 Hz, 1H); 7.30 (broad d, J=8.0 Hz, 1H); 7.46 (broad d, J=8.0 Hz, 1H); from 7.58 to 7.65 (m, 2H); 7.91 (m, 1H); 11.6 (broad m, 1H); 13.4 (broad s, 1H).

Example 19

3-[5-(2-Piperidin-1-yl-ethoxy)-1H-indol-2-yl]-1H-indazol-5-yl-phosphinic acid methyl ester The compound can be prepared in 6 stages according to the scheme:

Scheme

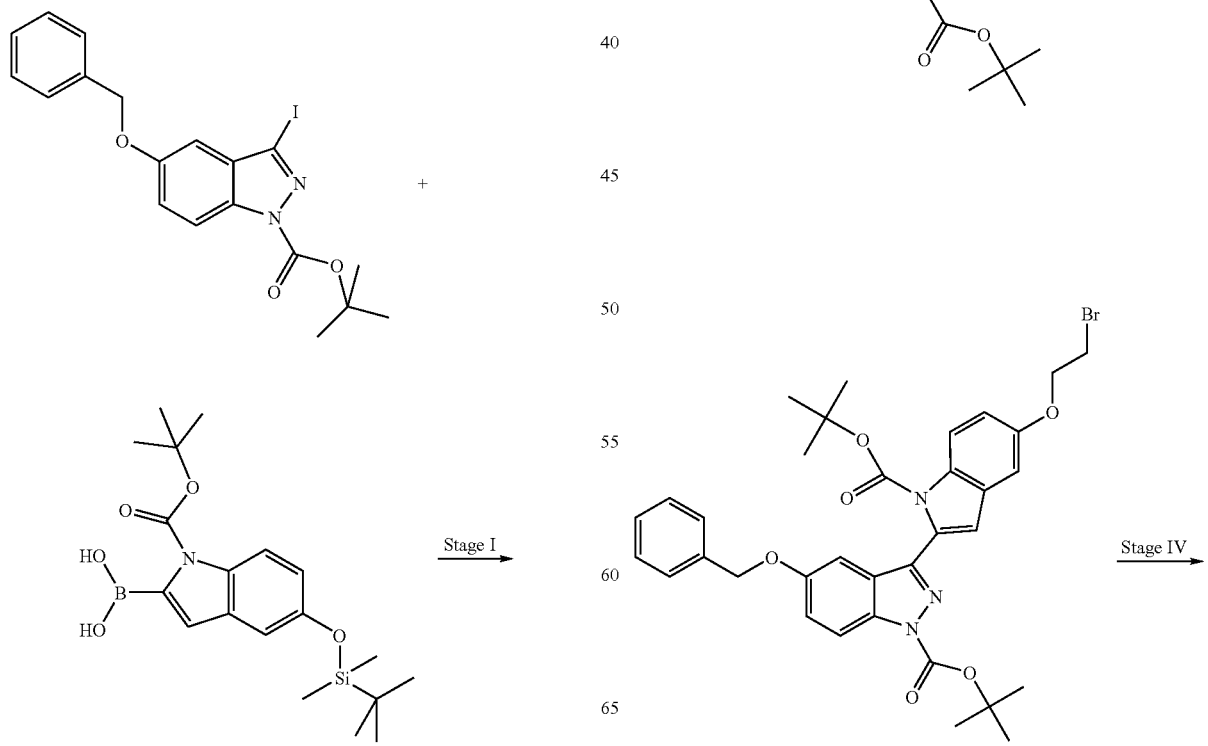

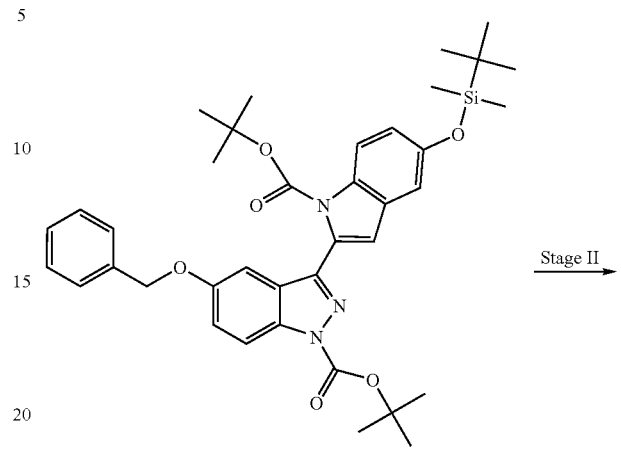

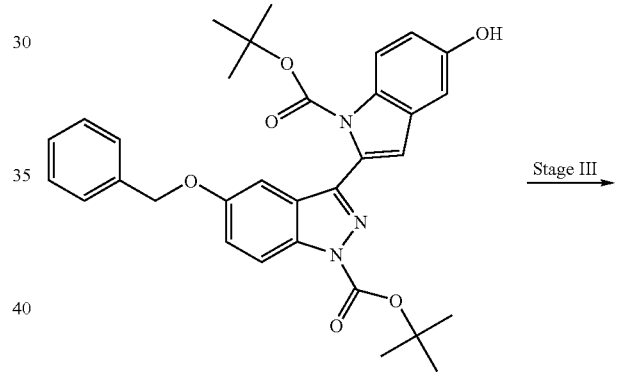

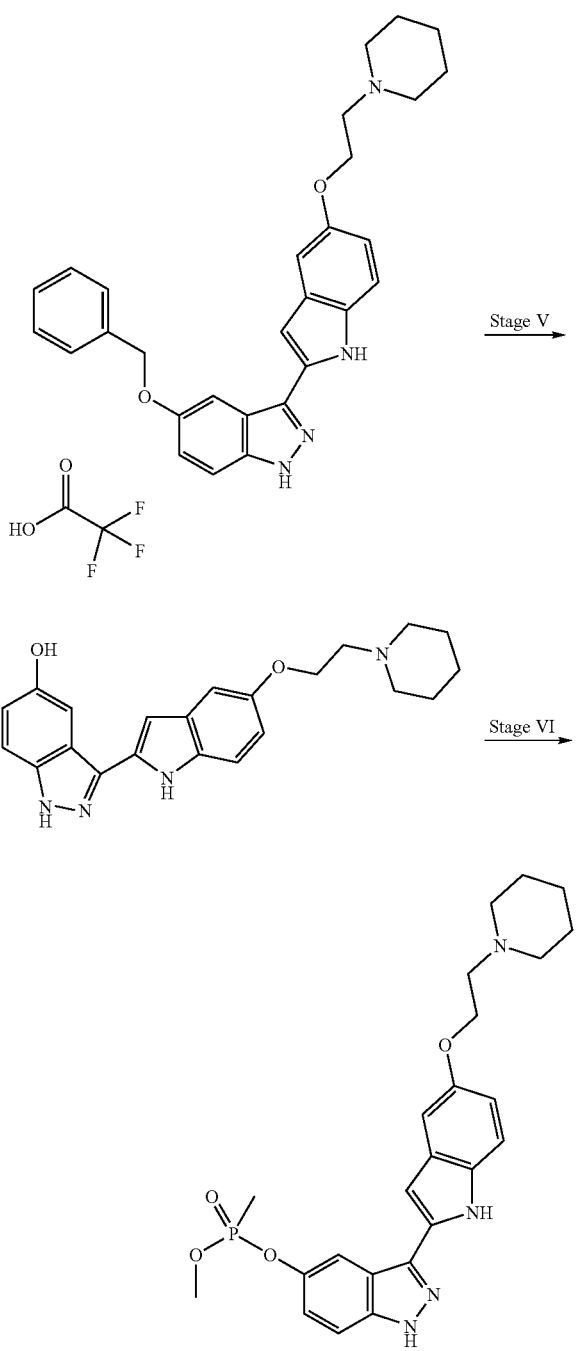

Stage II: 5-Benzyloxy-3-(1-tert-butoxycarbonyl-5-hydroxy-1H-indol-2-yl)-indazole-1-carboxylic acid tert-butoxide is prepared according to procedure G1.

Stage III: 5-Benzyloxy-3-[5-(2-bromoethoxy)-1-tert-butoxycarbonyl-1H-indol-2-yl]indazole-1-carboxylic acid tert-butoxide is prepared according to procedure G2.

Stage IV: 5-Benzyloxy-3-[5-(2-piperidin-1-ylethoxy)-1H-indol-2-yl]-1H-indazole trifluoroacetate is obtained in the following way:

A suspension of 600 mg of 5-benzyloxy-3-[5-(2-bromoethoxy)-1-tert-butoxycarbonyl-1H-indol-2-yl]indazole-1-carboxylic acid tert-butoxide, 442 mg of potassium carbonate and 272 mg of piperidine in 30 ml of acetonitrile is stirred at 85° C. for 5 hours. After returning to 20° C., the reaction mixture is evaporated under reduced pressure and the residue is then taken up in a mixture of ethyl acetate (100 ml) and of water (100 ml). After separation by settling out and extraction with ethyl acetate (1×50 ml), the organic extracts are combined, dried over magnesium sulfate and then evaporated under reduced pressure. The compound derived from the evaporation is taken up in a mixture of 15 ml of dichloromethane and 5 ml of trifluoroacetic acid and then stirred at 20° C. for one hour. The reaction mixture is evaporated under reduced pressure and the residue is taken up in a mixture of ethyl acetate (50 ml) and of sodium bicarbonate at 10% (50 ml). After separation by settling out and extraction with ethyl acetate (2×50 ml), the organic extracts are combined, dried over magnesium sulfate and then evaporated under reduced pressure. The crude compound thus obtained is purified by chromatography on silica (Interchrom column, DC0210, 20 g silica; eluent dichloromethane: methanol 9:1 by volume, 15 ml/min). The fractions containing the expected compound are combined and evaporated under reduced pressure to obtain 360 mg of 5-benzyloxy-3-[5-(2-piperidin-1-ylethoxy)-1H-indol-2-yl]-1H-indazole trifluoroacetate.

Stage V: 3-[5-(2-Piperidin-1-ylethoxy)-1H-indol-2-yl]-1H-indazol-5-ol is obtained in the following way:

A suspension of 360 mg of 5-benzyloxy-3-[5-(2-piperidin-1-ylethoxy)-1H-indol-2-yl]-1H-indazole, 916 mg of ammonium formate and 120 mg of palladium in 10 ml of ethanol is placed in a reactor that is irradiated in a microwave field (Synthwave 402) at a temperature of 90° C. for 30 minutes and the reaction mixture is then filtered through a bed of celite. The filtrate is evaporated under reduced pressure and the residue is then-taken up in a mixture of ethyl acetate (150 ml) and of water (50 ml). A 30% ammonium hydroxide solution is added so as to bring the pH to 10. After separation by settling out and extraction with ethyl acetate (1×50 ml), the organic extracts are combined, dried over magnesium sulfate and then evaporated under reduced pressure. 193 mg of 3-[5-(2-piperidin-1-ylethoxy)-1H-indol-2-yl]-1H-indazol-5-ol are isolated and characterized.

Stage I:

5-Benzyloxy-3-[1-tert-butoxycarbonyl-5-(tert-butyldimethylsilanyloxy)-1H-indol-2-yl]indazole-1-carboxylic acid tert-butoxide is prepared according to procedure G, using 5-benzyloxy-3-iodoindazole-1-carboxylic acid tert-butyl ester and [5-(tert-butyldimethylsilanyloxy)indole-1-carboxylic acid tert-butyl ester]-2 boronic acid, the title compound is obtained as described in WO 2003020699 A2.

Stage VI: Preparation of 3-[5-(2-piperidin-1-ylethoxy)-1H-indol-2-yl]-1H-indazol-5-ylphosphonic acid methyl ester:

77 µl of 1,8-diazabicyclo[5.4.0]undec-7-ene are added to a solution of 193 mg of 3-[5-(2-piperidin-1-ylethoxy)-1H-indol-2-yl]-1H-indazol-5-ol and 173.5 mg of methylphosphonic acid bis-(4-nitrophenyl) ester in 10 ml of dichloromethane and the mixture is allowed to react at 20° C. After reaction for three hours, 300 µl of methanol and then 77 µl of 1,8-diazabicyclo[5.4.0]undec-7-ene are added and the reaction is continued at 20° C. for 16 hours. The reaction medium is then taken up in a mixture of dichloromethane (150 ml) and a saturated sodium bicarbonate solution (100 ml). After separation by settling out and extraction with dichloromethane (50 ml), the organic extracts are combined, dried over magnesium sulfate and then evaporated under reduced pressure. The crude compound thus obtained is purified by chromatography on silica (Interchrom column, reference DC0210, 20 g silica, eluent dichloromethane/methanol 9/1 v/v, 15 ml/min). The fractions containing the expected compound are combined and evaporated under reduced pressure. 89 mg of 3-[5-(2-piperidin-1-ylethoxy)-1H-indol-2-yl]-1H-indazol-5-ylphosphonic acid methyl ester are isolated and characterized.

Analytical LC/MS: $[M+H]^+$=469.25; retention time=3.02 minutes

Example 20

Methylphosphonic acid mono-{3-[5-(2-piperazin-1-ylethoxy)-1H-indol-2-yl]-1H-indazol-5-yl}ester The title compound is prepared in 6 stages according to the following scheme:

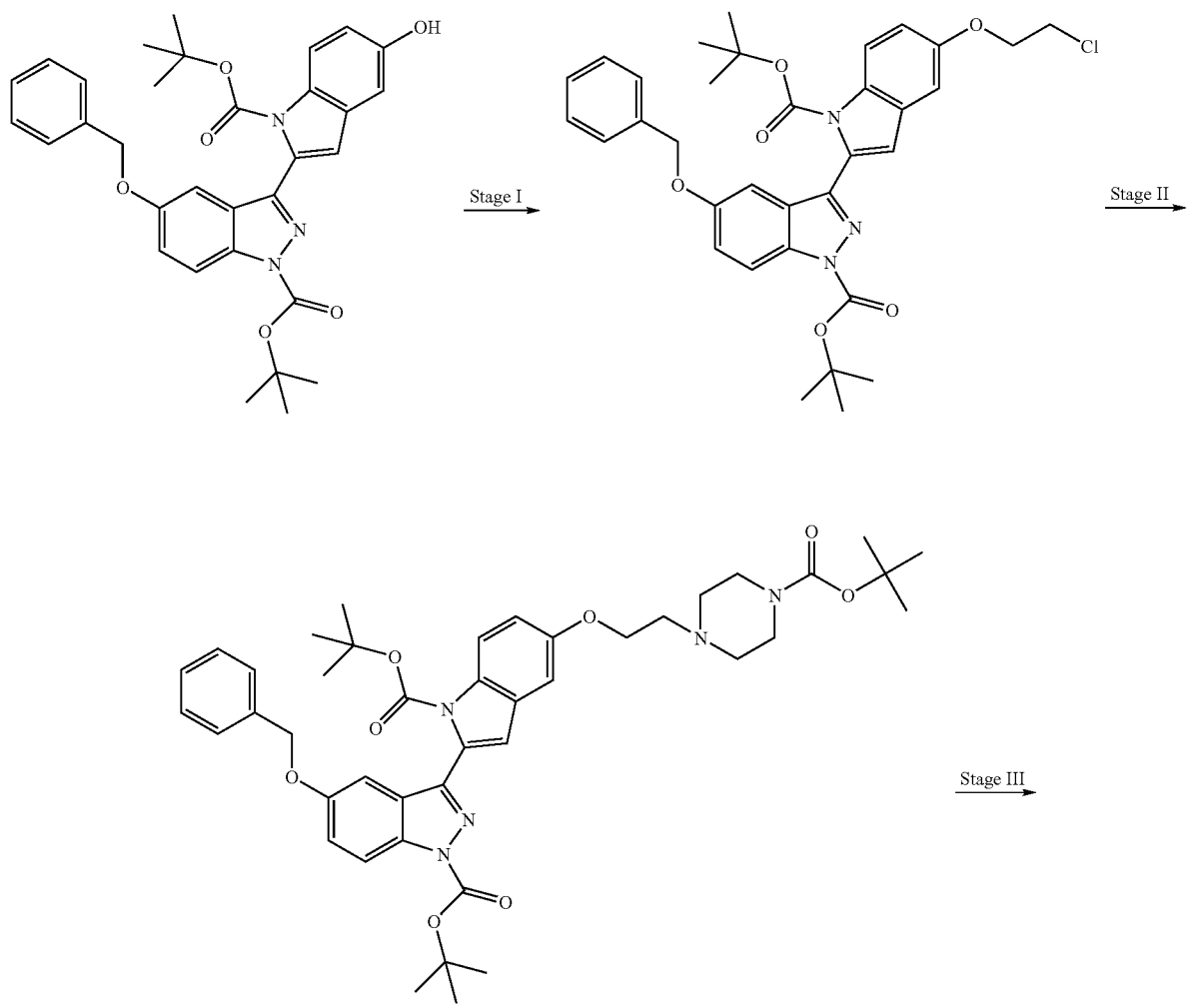

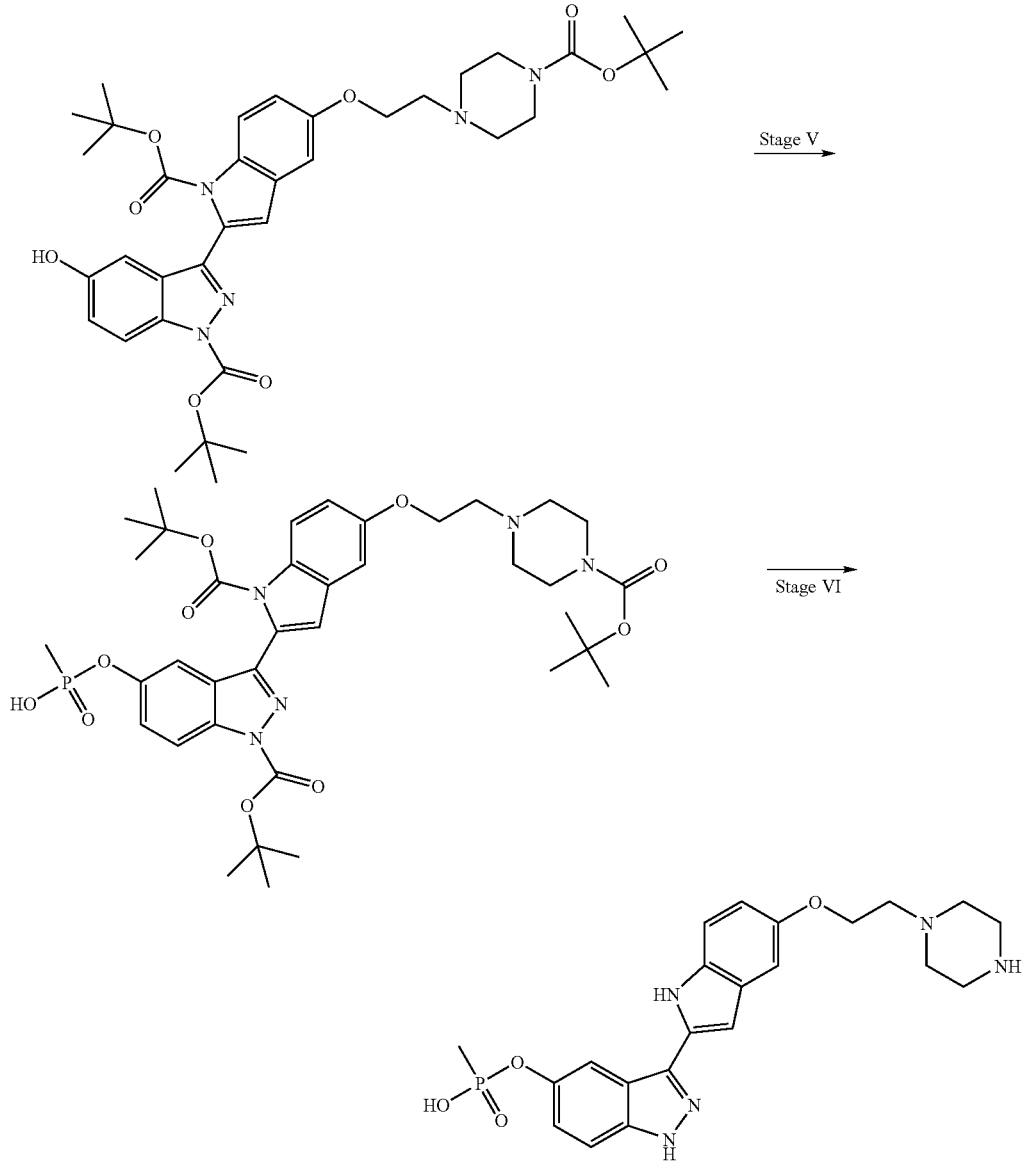

Stage I: Procedure J 5-Benzyloxy-3-[1-tert-butoxycarbonyl-5-(2-chloro-ethoxy)-1H-indol-2-yl]indazole-1-carboxylic acid tert-butyl ester is prepared in the following way:

A solution of 100 mg of 5-benzyloxy-3-(1-tert-butoxycarbonyl-5-hydroxy-1H-indol-2-yl)indazole-1-carboxylic acid tert-butyl ester and 132 µl of 1-bromo-2-chloroethane in 5 ml of dichloromethane is mixed with an aqueous solution of 72 mg of tetrabutylammonium bromide and of 270 µl of 2N sodium hydroxide in 5 ml of distilled water. The reaction mixture is stirred vigorously at 20° C. for 6 hours. After separation by settling out and washing with water (4×5 ml), the organic extracts are combined, dried over magnesium sulfate and then evaporated under reduced pressure. The crude compound obtained is purified by preparative LC/MS. The fractions containing the expected compound are combined and evaporated under reduced pressure to obtain 18.1 mg of 5-benzyloxy-3-[1-tert-butoxycarbonyl-5-(2-chloroethoxy)-1H-indol-2-yl]-indazole-1-carboxylic acid tert-butyl ester, which is characterized as follows:

Analytical LC/MS: [M+H]$^+$=618.15; retention time=5.56 minutes.

Stage II: 5-Benzyloxy-3-{1-tert-butoxycarbonyl-5-[2-(4-tert-butoxycarbonyl-piperazin-1-yl)ethoxy]-1H-indol-2-yl}indazole-1-carboxylic acid tert-butyl ester is prepared in the following way:

A suspension of 330 mg of 5-benzyloxy-3-[1-tert-butoxycarbonyl-5-(2-chloro-ethoxy)-1H-indol-2-yl]indazole-1-carboxylic acid tert-butyl ester, 442 mg of potassium carbonate, 133 mg of potassium iodide and 596 mg of N-1-Boc-piperazine in 15 ml of acetonitrile is stirred at 85° C. for 48 hours. After returning to 20° C, the reaction mixture is evaporated under reduced pressure and the residue is then taken up in a mixture of ethyl acetate (15 ml) and of water (15 ml).

After separation by settling out and extraction with ethyl acetate (1×15 ml), the organic extracts are combined, dried over magnesium sulfate and then evaporated under reduced pressure. The crude compound thus obtained is purified by chromatography on silica (AIT column, BPSUP 20-40 μm, 25 g silica; eluent cyclohexane: ethyl acetate 1:1 by volume). The fractions containing the expected compound are combined and evaporated under reduced pressure. The compound thus obtained is dissolved in 10 ml of dichloromethane and then treated with 350 mg of di-tert-butyl dicarbonate and 10 mg of dimethylaminopyridine at 20° C. for 3 hours. The reaction mixture is evaporated under reduced pressure to obtain 220 mg of 5-benzyloxy-3-{1-tert-butoxycarbonyl-5-[2-(4-tert-butoxycarbonylpiperazin-1-yl)ethoxy]-1H-indol-2-yl}indazole-1-carboxylic acid tert-butyl ester, which is characterized, and used without purification.

Analytical LC/MS: $[M+H]^+$=768.39; retention time=4.00 minutes.

Stage III: 3-{1-tert-Butoxycarbonyl-5-[2-(4-tert-butoxycarbonylpiperazin-1-yl)-ethoxy]-1H-indol-2-yl}-5-hydroxyindazole-1-carboxylic acid tert-butyl ester is prepared in the following way:

A suspension of 220 mg of 5-benzyloxy-3-{1-tert-butoxycarbonyl-5-[2-(4-tert-butoxycarbonylpiperazin-1-yl)ethoxy]-1H-indol-2-yl}indazole-1-carboxylic acid tert-butyl ester, 108 mg of ammonium formate and 29.8 mg of palladium in 30 ml of ethanol is placed in a reactor, which is vigorously stirred while at the same time bringing it to a temperature of 80° C. After 4 hours, the reaction mixture is filtered through a bed of celite. The filtrate is again reacted with 108 mg of ammonium formate and 29.8 mg of palladium for a further 4 hours. The reaction mixture is then filtered through a bed of celite, and evaporated under reduced pressure, and the residue is then taken up in a mixture of ethyl acetate (20 ml) and of a saturated sodium bicarbonate solution (20 ml). After separation by settling out and extraction with ethyl acetate (2×20 ml), the organic extracts are combined, dried over magnesium sulfate and then evaporated under reduced pressure.

The compound obtained (60 mg) is subjected to a third reaction cycle in the presence of 38 mg of ammonium formate and of 12 mg of palladium in 30 ml of ethanol, irradiating in a microwave oven (temperature 90° C.) for 30 minutes. The reaction mixture is filtered through a bed of celite, and evaporated under reduced pressure. 34 mg of a crude compound containing 3-{1-tert-butoxycarbonyl-5-[2-(4-tert-butoxycarbonylpiperazin-1-yl)ethoxy]-1H-indol-2-yl}-5-hydroxyindazole-1-carboxylic acid tert-butyl ester are isolated, which is used in the subsequent stage without purification.

Analytical LC/MS: $[M+H]^+$=678.74; retention time=3.31 minutes.

Stage IV: 3-{1-tert-Butoxycarbonyl-5-[2-(4-tert-butoxycarbonylpiperazin-1yl)-ethoxy]-1H-indol-2-yl}-5-(hydroxymethylphosphinoyloxy)indazole-1-carboxylic acid tert-butyl ester A solution of 34 mg of 3-{1-tert-butoxycarbonyl-5-[2-(4-tert-butoxycarbonyl-piperazin-1-yl)ethoxy]-1H-indol-2-yl}-5-hydroxyindazole-1-carboxylic acid tert-butyl ester in 1.5 ml of dichloromethane is cooled in an ice bath. 16.9 mg of methylphosphonic acid bis-(4-nitrophenyl)ester prepared according to procedure E and 7.6 mg of 1,8-diazabicyclo [5.4.0]undec-7-ene in 500 μl of dichloromethane are added and the reaction is continued at 20° C. for 3 hours. The reaction medium is washed with 2 times 3 ml of a saturated sodium bicarbonate solution and then with 3 ml of distilled water. After separation by settling out, the organic extracts are dried over magnesium sulfate and then evaporated under reduced pressure. 39 mg of a mixture containing mainly 3-{1-tert-butoxycarbonyl-5-[2-(4-tert-butoxycarbonylpiperazin-1-yl)ethoxy]-1H-indol-2-yl}-5-(hydroxymethylphosphinoyloxy)indazole-1-carboxylic acid tert-butyl ester are isolated, which is used in the subsequent stage without purification.

Analytical LC/MS: $[M+H]^+$=756.76; retention time=3.45 minutes.

Stage V: Methylphosphonic acid mono-{3-[5-(2-piperazin-1-ylethoxy)-1H-indol-2-yl]-1 H-indazol-5-yl}ester:

A solution of 39 mg of the preceding mixture containing mainly 3-{1-tert-butoxycarbonyl-5-[2-(4-tert-butoxycarbonylpiperazin-1-yl)ethoxy]-1H-indol-2-yl}-5-(hydroxymethylphosphinoyloxy)indazole-1-carboxylic acid tert-butyl ester in 1 ml of dichloromethane and 200 μl of trifluoroacetic acid is stirred at 20° C. for 4 hours and the reaction mixture is then evaporated under reduced pressure. The crude compound obtained is purified by preparative LCMS, and the fractions containing the compound of molecular mass 455 are combined and evaporated under reduced pressure to yield 4 mg of methylphosphonic acid mono-{3-[5-(2-piperazin-1-ylethoxy)-1H-indol-2-yl]-1H-indazol-5-yl}ester, which is characterized.

Analytical LC/MS: $[M+H]^+$=456.33; retention time=1.85 minutes.

Examples 21 and 22

Methylphosphonic acid mono-{3-[5-(2-diethylaminoethoxy)-1H-indol-2-yl]-1H-indazol-5-yl}ester (Example 21) and methyl-phosphonic acid 3-[5-(2-diethylaminoethoxy)-1H-indol-2-yl]-1H-indazol-5-yl ester methyl ester (Example 22)

The title compounds are prepared in 4 stages according to the following scheme:

Scheme

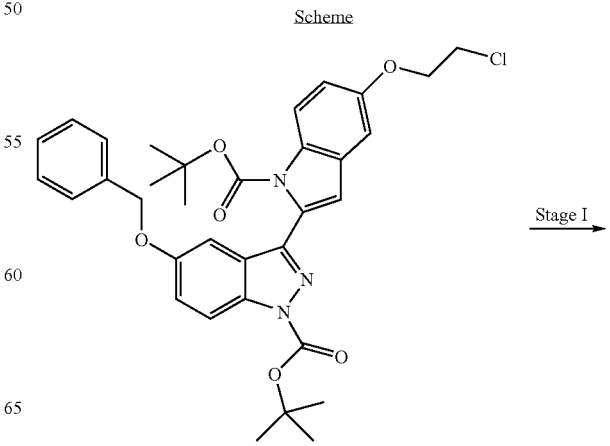

Stage I

-continued

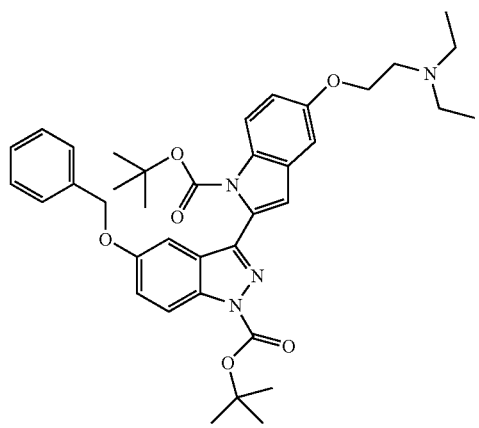

Stage II →

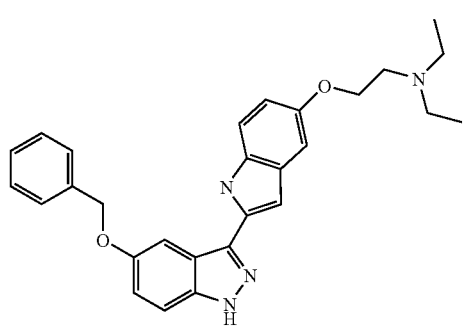

Stage III →

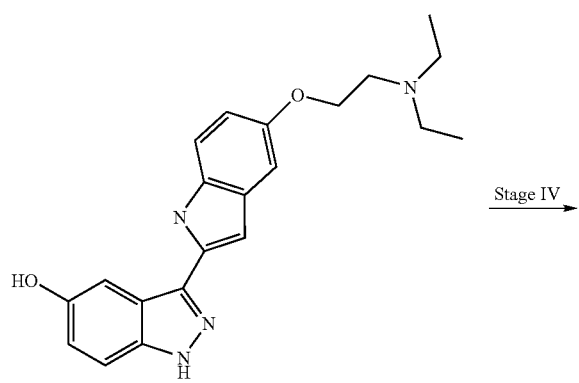

Stage IV →

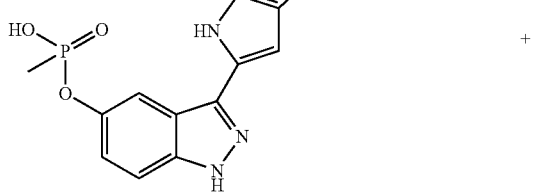

Example 21

-continued

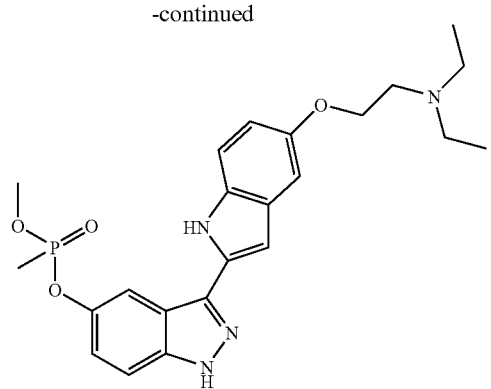

Example 22

Stage I: Preparation of 5-benzyloxy-3-[1-tert-butoxycarbonyl-5-(2-diethylaminoethoxy)-1H-indol-2-yl]indazole-1-carboxylic Acid Tert-butyl Ester A solution containing 1.5 g of 5-benzyloxy-3-[1-tert-butoxycarbonyl-5-(2-chloroethoxy)-1H-indol-2-yl]indazole-1-carboxylic acid tert-butyl ester prepared according to procedure J, 1 g of potassium carbonate, 600 mg of potassium iodide and 761 µl of ethylamine in 75 ml of acetonitrile is heated at 80° C. for 18 hours. After this period of time, 1.5 ml of ethylamine are added and the reaction is continued for a further 18 hours at 80° C. This operation is repeated after a further 18 hours and the reaction mixture is then evaporated under reduced pressure. The brown oil obtained is taken up in a mixture of ethyl acetate (80 ml) and of water (80 ml). After separation by settling out and extraction with ethyl acetate (80 ml), the organic extracts are combined, washed with water (100 ml) and with brine (100 ml), dried over magnesium sulfate and then evaporated under reduced pressure to obtain 1.15 g of 5-benzyloxy-3-[1-tert-butoxycarbonyl-5-(2-diethylaminoethoxy)-1H-indol-2-yl]indazole-1-carboxylic acid tert-butyl ester, which is used as it is in the subsequent stage.

Stage II: Preparation of {2-[2-(5-benzyloxy-1H-indazol-3-yl)-1H-indol-5-yloxy]-ethyl}diethylamine A solution containing 1.15 g of 5-benzyloxy-3-[1-tert-butoxycarbonyl-5-(2-diethylaminoethoxy)-1H-indol-2-yl]indazole-1-carboxylic acid tert-butyl ester and 4 ml of trifluoroacetic acid in 5 ml of dichloromethane is stirred at 20° C. for 2 hours. The reaction mixture is evaporated under reduced pressure and the crude compound thus obtained is purified by chromatography (Nucleodur C18 column, 100-10, 250 mm×40 mm, reference No. 762020, series No. 3051181, Batch No. 2023; eluent A: water/0.07% trifluoroacetic acid, eluent B: acetonitrile/0.07% trifluoroacetic acid, gradient of composition A/B of 95%//5% to 5%/95% over 52 minutes at 75 ml/min, detection 300 nm). The fractions containing the expected compound are combined and evaporated under reduced pressure. The compound is taken up in ethyl acetate (20 ml), dried over magnesium sulfate and then evaporated under reduced pressure to obtain 320 mg of {2-[2-(5-benzyloxy-1H-indazol-3-yl)-1H-indol-5-yloxy]ethyl}diethylamine, which is characterized.

Stage III: Preparation of 3-[5-(2-diethylaminoethoxy)-1H-indol-2-yl]-1H-indazol-5-ol A suspension of 320 mg of {2-[2-(5-benzyloxy-1H-indazol-3-yl)-1H-indol-5-yloxy]ethyl}diethylamine, 32 mg of palladium-on-charcoal at 10%, and 180 mg of ammonium formate is irradiated in a Synthwave 402 microwave oven at atmospheric pressure for 35 minutes at 75° C. at 5% power, and then for 10 minutes at 20% power. The catalyst is filtered through a bed of celite, and the filtrate is evaporated under reduced pressure. The compound obtained is taken up in ethyl acetate (20 ml) and a saturated sodium bicarbonate solution (20 ml), separated by settling out, dried over magnesium sulfate and then evaporated under reduced pressure to obtain 115 mg of 3-[5-(2-diethylaminoethoxy)-1H-indol-2-yl]-1H-indazol-5-ol, which is characterized.

Analytical LC/MS: $[M+H]^+$=365.29; retention time=2.33 minutes.

Stage IV: Preparation of Methylphosphonic Acid Mono-{3-[5-(2-diethylamino-ethoxy)-1H-indol-2-yl]-1H-indazol-5-yl}Ester and Methylphosphonic Acid 3-[5-(2-diethylaminoethoxy)-1H-indol-2-yl]-1H-indazol-5-yl Ester Methyl Ester A suspension of 115 mg of 3-[5-(2-diethylaminoethoxy)-1H-indol-2-yl]-1H-indazol-5-ol in 3 ml of dichloromethane is stirred at 20° C. during the addition of 107 mg of methylphosphonic acid bis-(4-nitrophenyl) ester (prepared according to procedure E) and of 48 μl of 1,8-diazabicyclo[5.4.0]undec-7-ene. After 18 hours at this temperature, 128 μl of methanol and 50 μl of 1,8-diazabicyclo[5.4.0]undec-7-ene in 1 ml of tetrahydrofuran are added and the reaction is continued for 4 hours. The reaction mixture is evaporated under reduced pressure. 300 mg of a compound are isolated, which compound is purified by chromatography (Nucleodur C18 column, 100-10, 250 mm×40 mm, reference No. 762020, series No. 3051181, Batch No. 2023; eluent A: water/0.07% trifluoroacetic acid, eluent B: acetonitrile/0.07% trifluoroacetic acid, gradient of composition A/B of 95%/5% to 5%/95% over 52 minutes at 75 ml/min, detection 300 nm).

The fractions containing the methylphosphonic acid mono-{3-[5-(2-diethylaminoethoxy)-1H-indol-2-yl]-1H-indazol-5-yl} ester (MM 442) are combined and evaporated under reduced pressure.

The fractions containing the methylphosphonic acid 3-[5-(2-diethylamino-ethoxy)-1H-indol-2-yl]-1H-indazol-5-yl ester methyl ester (MM 456) are combined and evaporated under reduced pressure.

Each compound isolated above is taken up in 500 μl of methanol and then loaded onto an SCX cartridge (Varian, 500 mg). After loading, the cartridge is first rinsed with methanol, and then eluted with a mixture of methanol and 2M ammonia. The eluents are evaporated under reduced pressure. The compounds obtained are purified by preparative LCMS.

The fractions containing the compound of molar mass 442 are combined and evaporated under reduced pressure. 22.9 mg of methylphosphonic acid mono-{3-[5-(2-diethylaminoethoxy)-1H-indol-2-yl]-1H-indazol-5-yl}ester (Example 21), are isolated, which compound is characterized by analytical LC/MS.

Analytical LC/MS: $[M+H]^+$=442.18; retention time=2.43 minutes.

The fractions containing the compound of molar mass 456 are combined and evaporated under reduced pressure. 12.8 mg of methylphosphonic acid 3-[5-(2-diethylaminoethoxy)-1H-indol-2-yl]-1H-indazol-5-yl ester methyl ester (Example 22) are isolated, which compound is characterized by LC/MS.

Analytical LC/MS: $[M+H]^+$=456.19; retention time=2.76 minutes.

Example 23

Phenylphosphonic acid ethyl ester 3-(5-methoxy-1H-pyrrolo[3,2-b]pyridin-2-yl)-1H-indazol-5-yl ester The compound is prepared in 6 stages according to the following scheme:

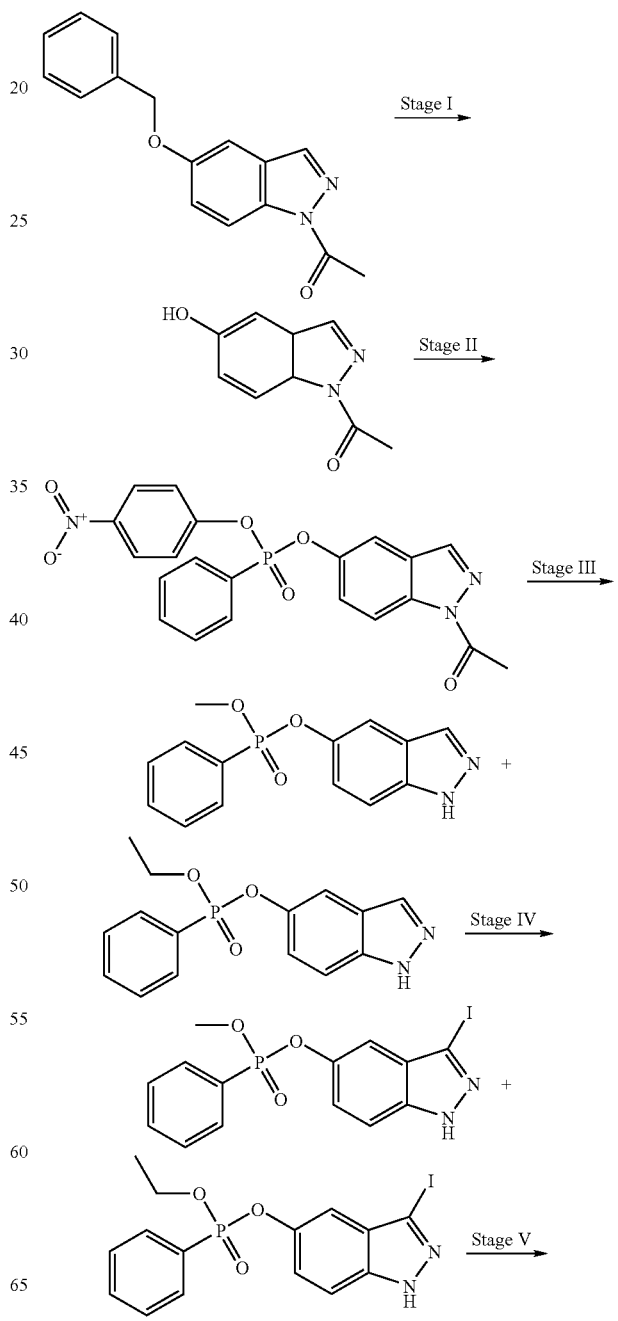

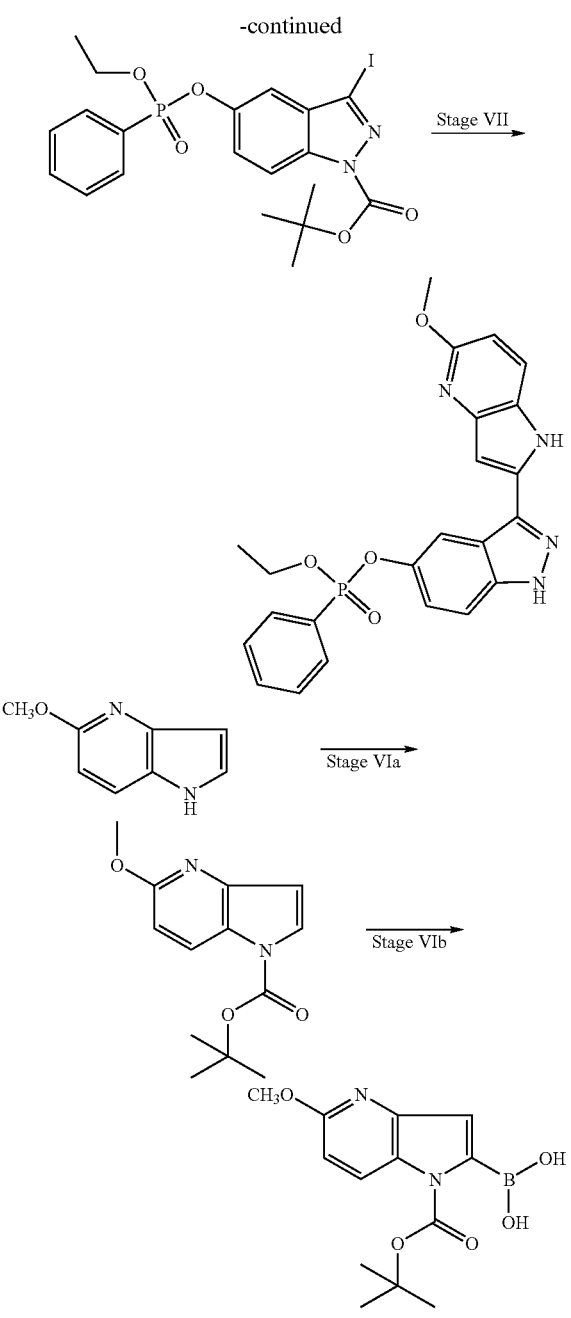

Procedure K corresponds to stages I to V

Stage I: Preparation of phenylphosphonic acid ethyl ester 3-(5-methoxy-1H-pyrrolo[3,2-b]pyridin-2-yl)-1H-indazol-5-yl ester 1-(5-Benzyloxyindazol-1-yl)ethanone is prepared according to the method described during stage 2 for synthesizing the intermediate A.

A suspension of 1 g of 1-(5-benzyloxyindazol-1-yl)ethanone, 1.42 g of ammonium formate and 0.59 g of palladium-on-charcoal at 10% in ethanol is refluxed for 16 hours. After returning to 20° C., the reaction mixture is filtered through a bed of celite and the filtrate is evaporated under reduced pressure. The crude compound thus obtained is triturated in 10 ml of diisopropyl ether and then filtered and dried under reduced pressure to obtain 400 mg of 1-(5-hydroxy-indazol-1-yl)-ethanone, which is characterized.

Stage II: Preparation of phenylphosphonic acid 1-acetyl-1H-indazol-5-yl ester 4-nitrophenyl ester A solution of 2.36 g of phenylphosphonic acid bis-(4-nitrophenyl) ester (prepared according to procedure E) in 60 ml of dichloromethane is cooled in an ice bath. 1.041 g of 1-(5-hydroxyindazol-1-yl)ethanone and 900 mg of 1,8-diazabicyclo[5.4.0]undec-7-ene in 40 ml of dichloromethane are added thereto and the reaction is continued at 20° C. for 2 hours. The reaction medium is washed with a saturated sodium bicarbonate solution until discoloration of the organic phase. After separation by settling out, the organic extracts are dried over magnesium sulfate and then evaporated under reduced pressure. 2.4 g of phenylphosphonic acid 1-acetyl-1H-indazol-5-yl ester 4-nitrophenyl ester are isolated, which compound is used without purification in the subsequent stage.

Stage III: Preparation of phenylphosphonic acid 1H-indazol-5-yl ester methyl ester Warning: during this reaction, the use of dichloromethane stabilized with ethanol makes it possible to identify a trace of phosphonic acid ethyl ester contaminating the main compound (25% UV).

A solution of 2.4 g of phenylphosphonic acid 1-acetyl-1H-indazol-5-yl ester 4-nitrophenyl ester in 30 ml of dichloromethane stabilized with ethanol is stirred at 20° C. A solution of 3.78 ml of methanol and of 836 mg of 1,8-diazabicyclo[5.4.0]undec-7-ene in 30 ml of dichloromethane is added thereto. The reaction is continued at this temperature overnight. The reaction mixture is evaporated under reduced pressure and the crude compound thus obtained is then purified by chromatography on silica (AIT BP-SUP 20-40 μm, eluent 90/10 dichloromethane/methanol). The fractions containing the expected compound are combined and evaporated under reduced pressure. 980 mg of phenylphosphonic acid 1H-indazol-5-yl ester methyl ester are isolated and characterized.

Analytical LC/MS: [M+H]$^+$=289.13; retention time=2.83 minutes.

This compound is contaminated with phenylphosphonic acid 1H-indazol-5-yl ester ethyl ester, which is not isolated.

Analytical LC/MS: M+H ]$^+$=303.0; retention time=3.01 minutes.

Stage IV: Preparation of phenylphosphonic acid 3-iodo-1H-indazol-5-yl ester methyl ester Warning: during this reaction, the use of the starting material described in stage II, containing 25% of the ethyl ester isomer, makes it possible to also isolate the corresponding iodinated derivative.

A solution of 980 mg of phenylphosphonic acid 1H-indazol-5-yl ester methyl ester contaminated with phenylphosphonic acid 1H-indazol-5-yl ester ethyl ester, in dimethylformamide, is stirred vigorously at 20° C. 1.72 g of iodine and 381.5 mg of potassium hydroxide are added thereto and the mixture is then allowed to react for 16 hours. The reaction medium is diluted with a mixture of ethyl acetate (60 ml) and saturated sodium thiosulfate solution (40 ml). After stirring for 10 minutes at 20° C., the reaction medium is separated by settling out, and washed with distilled water (40 ml); the organic extracts are combined, dried over magnesium sulfate and then evaporated under reduced pressure. 1.08 g of crude compound thus obtained is purified by chromatography (Nucleodur C18 column, 100-10, 250 mm×40 mm, reference No. 762020, series No. 3051181, Batch No. 2023; eluent A: water/0.07% trifluoroacetic acid, eluent B: acetonitrile/ 0.07% trifluoroacetic acid, gradient of composition A/B of 95%/5% to 5%/95% over 52 minutes at 75 ml/min).

The fractions containing the compound of molar mass 414 are combined and evaporated under reduced pressure to obtain 510 mg of phenylphosphonic acid 3-iodo-1H-indazol-5-yl ester methyl ester, which is characterized.

The fractions containing the compound of molar mass 428 are combined and evaporated under reduced pressure to obtain 80 mg of phenylphosphonic acid 3-iodo-1H-indazol-5-yl ester ethyl ester, which is characterized.

Stage V: Preparation of 5-(ethoxyphenylphosphinoyloxy)-3-iodoindazole-1-carboxylic Acid Tert-butyl Ester A solution of 80 mg of phenylphosphonic acid 3-iodo-1H-indazol-5-yl ester ethyl ester in 2 ml of dichloromethane is stirred at 20° C. 40 mg of di-tert-butyl dicarbonate and 22 mg of dimethylaminopyridine are added thereto and the reaction is continued at 20° C. for 16 hours. The reaction mixture is evaporated under reduced pressure to obtain 60 mg of 5-(ethoxyphenylphosphinoyloxy)-3-iodoindazole-1-carboxylic acid tert-butyl ester, which is characterized, and used as it is.

Analytical LC/MS: [M+H]$^+$=529.06; retention time=4.29 minutes.

Stage VI: Preparation of 5-methoxypyrrolo[3,2-b]pyridine-2-boronic acid 1-carboxylic acid tert-butyl ester This compound is prepared in two stages using 5-methoxypyrrolo[3,2-b]pyridine, as described below.

Stage VIa: Preparation of 5-methoxypyrrolo[3,2-b]pyridine-1-carboxylic acid tert-butyl ester 102 mg of 4-dimethylaminopyridine are added to a solution of 4.50 g of 5-methoxypyrrolo[3,2-b]pyridine (prepared as described in Liebigs Ann. Chem. 1988, 203-208) and 10.7 g of di-tert-butyl dicarbonate in 10 ml of anhydrous dichloromethane, with magnetic stirring at 20° C. The solution thus obtained is continued to stir at ambient temperature overnight and the reaction medium is then washed with 75 ml of water and then 75 ml of brine. The organic extract is dried over magnesium sulfate and then evaporated under reduced pressure. The crude compound thus obtained is purified by chromatography on silica, eluting with dichloromethane and then with a 90/10 mixture of dichloromethane and ethyl acetate, to give 7.06 g of 5-methoxypyrrolo[3,2-b]pyridine-1-carboxylic acid tert-butyl ester in the form of an amber oil which is characterized by NMR.

NMR: $^1$H NMR [300 MHz, (CD$_3$)$_2$SO]: δ 8.21 (d, J=9 Hz, 1H), 7.85 (d, J=4 Hz, 1H), 6.76 (d, J=9 Hz, 1H), 6.70 (d, J=4 Hz, 1 H), 3.89 (s, 3H), 1.63 (s, 9H).

Stage VIb: Introduction of Boronic Acid

A solution of 15 ml of 1.5M tert-butyllithium in pentane is added portionwise to a solution of 4.66 g of 5-methoxypyrrolo[3,2-b]pyridine-1-carboxylic acid tert-butyl ester (prepared above) in 85 ml of anhydrous tetrahydrofuran maintained under a dry nitrogen stream. The reaction medium thus obtained is stirred at −78° C. for 40 minutes and then 8 ml of a solution of triisopropyl borate (37.7 mmol) are added over a period of 2 minutes, and the reaction medium is then stirred and maintained at −78° C. for 20 minutes. The reaction medium is heated at 0° C. for 2 hours 30 min, and then 50 ml of water are added. After stirring for one hour at 20° C., the tetrahydrofuran is evaporated off under reduced pressure. The aqueous phase obtained is basified by adding 5N ammonium hydroxide, and then washed twice with ethyl acetate (30 ml). The aqueous extract is cooled to 0° C. and then treated with an aqueous acid potassium sulfate solution until a pH of 4 is obtained. The medium is stirred at 0° C. for 15 minutes. The solid formed is isolated by filtration and dried, to give 2.48 g of 5-methoxypyrrolo[3,2-b]pyridine-2-boronic acid 1-carboxylic acid tert-butyl ester in the form of a white powder.

RMN [300 MHz, (CD$_3$)$_2$SO]: δ 8.28 (s, 2H), 8.23 (d, J=9 Hz, 1H), 6.70 (d, J=9 Hz, 1H), 6.58 (s, 1H), 3.87 (s, 3H), 1.60 (s, 9H).

Stage VII: Preparation of phenylphosphonic acid ethyl ester 3-(5-methoxy-1H-pyrrolo[3,2-b]pyridin-2-yl)-1H-indazol-5-yl ester A suspension of 50 mg of 5-(ethoxyphenylphosphinoyloxy)-3-iodoindazole-1-carboxylic acid tert-butyl ester, 55.3 mg of 5-methoxypyrrolo[3,2-b]pyridine-2-boronic acid 1-carboxylic acid tert-butyl ester, 3.78 mg of 1,1'bis(diphenylphosphino)ferrocene palladium(II) dichloride and 123.4 mg of cesium carbonate in a mixture of 800 µl of dioxane and 250 µl of water is heated at 100° C. for 45 minutes. After returning to 20° C., the reaction medium is diluted with 3 ml of ethyl acetate and then washed with 2 times 1.5 ml of distilled water. After separation by settling out, the organic extract is dried over magnesium sulfate and then evaporated under reduced pressure.

The crude compound obtained is purified by preparative LCMS. The fractions containing the expected compound are combined and evaporated under reduced pressure to obtain 16.7 mg of phenylphosphonic acid ethyl ester 3-(5-methoxy-1H-pyrrolo[3,2-b]pyridin-2-yl)-1H-indazol-5-yl ester, which is characterized.

Analytical LC/MS: [M+H]$^+$=449.17; retention time=3.05 minutes.

Example 24

Procedure L: Preparation of phenylphosphonic acid 3-(5-methoxy-1H-pyrrolo[3,2-b]pyridin-2-yl)-1H-indazol-5-yl ester methyl ester A suspension composed of: 50 mg of 3-iodo-5-(methoxyphenyl-phosphinoyloxy)indazole-1-carboxylic acid tert-butyl ester obtained according to procedure K, 3.9 mg of 1,1'-bis(diphenylphosphino)ferrocene palladium(ii) dichloride, 56.81 mg of 5-methoxypyrrolo[3,2-b]pyridine-1-carboxylic acid tert-butyl ester 2-boronic acid, 126 mg of cesium carbonate, 260 µl of dioxane and 813 µl of distilled water is placed in a reactor and the reaction mixture is heated at 100° C. for 45 min. After returning to 20° C., the reaction medium is diluted with 4 ml of ethyl acetate and then washed with 2 times 3 ml of distilled water. After separation by settling out, the organic phase is dried over magnesium sulfate and then evaporated under reduced pressure. The crude compound obtained is purified by preparative LCMS. The fractions containing the expected compound are combined and evaporated under reduced pressure.

The intermediate compound thus obtained is dissolved in 300 μl of 1M hydrochloric acid solution in dioxane and stirred for 2 hours at 20° C., and the reaction mixture is then evaporated under reduced pressure. The crude compound obtained is purified by preparative LCMS. The fractions containing the expected compound are combined and evaporated under reduced pressure to obtain 3 mg of phenylphosphonic acid 3-(5-methoxy-1H-pyrrolo[3,2-b]pyridin-2-yl)-1H-indazol-5-yl ester methyl ester, which is characterized.

Analytical LC/MS: [M+H]$^+$=435; retention time=2.95 minutes.

Example 25

Phenylphosphonic acid methyl ester 3-styryl-1H-indazol-5-yl ester

The title compound is prepared according to procedure L employing 28.78 mg of trans-beta-styreneboronic acid to obtain 3 mg of phenylphosphonic acid methyl ester 3-styryl-1H-indazol-5-yl ester, which is characterized.

Analytical LC/MS: [M+H]$^+$=391; retention time=3.66 minutes.

Example 26

Phenylphosphonic acid 3-benzo[b]thiophen-2-yl-1H-indazol-5-yl ester methyl ester The title compound is prepared according to procedure L employing 24.89 mg of thiophene-2-boronic acid to obtain 3 mg of phenylphosphonic acid 3-benzo[b]thiophen-2-yl-1H-indazol-5-yl ester methyl ester, which is characterized.

Analytical LC/MS: [M+H]$^+$=371; retention time=3.41 minutes.

Example 27

Phenylphosphonic acid 3-benzo[b]thiophen-2-yl-1H-indazol-5-yl ester methyl ester The title compound is prepared according to procedure L employing 30 mg of 3-iodo-5-(methoxyphenylphosphinoyloxy)indazole-1-carboxylic acid tert-butyl ester, 21.2 mg of benzo[b]thiophene-2-boronic acid, 2.23 mg of 1,1'-bis(diphenylphosphino)ferrocene palladium(II) dichloride and 71 mg of cesium carbonate in 500 μl of dimethylformamide. 0.7 mg of phenylphosphonic acid 3-benzo[b]thiophen-2-yl-1H-indazol-5-yl ester methyl ester is isolated.

Analytical LC/MS: [M+H]$^+$=421.18; retention time=3.86 minutes.

Example 28

Methylphosphonic acid methyl ester 3-[5-(2-morpholin-4-ylethoxy)-1H-indol-2-yl]-1H-indazol-5-yl ester The product is prepared in 7 stages starting with intermediate A.

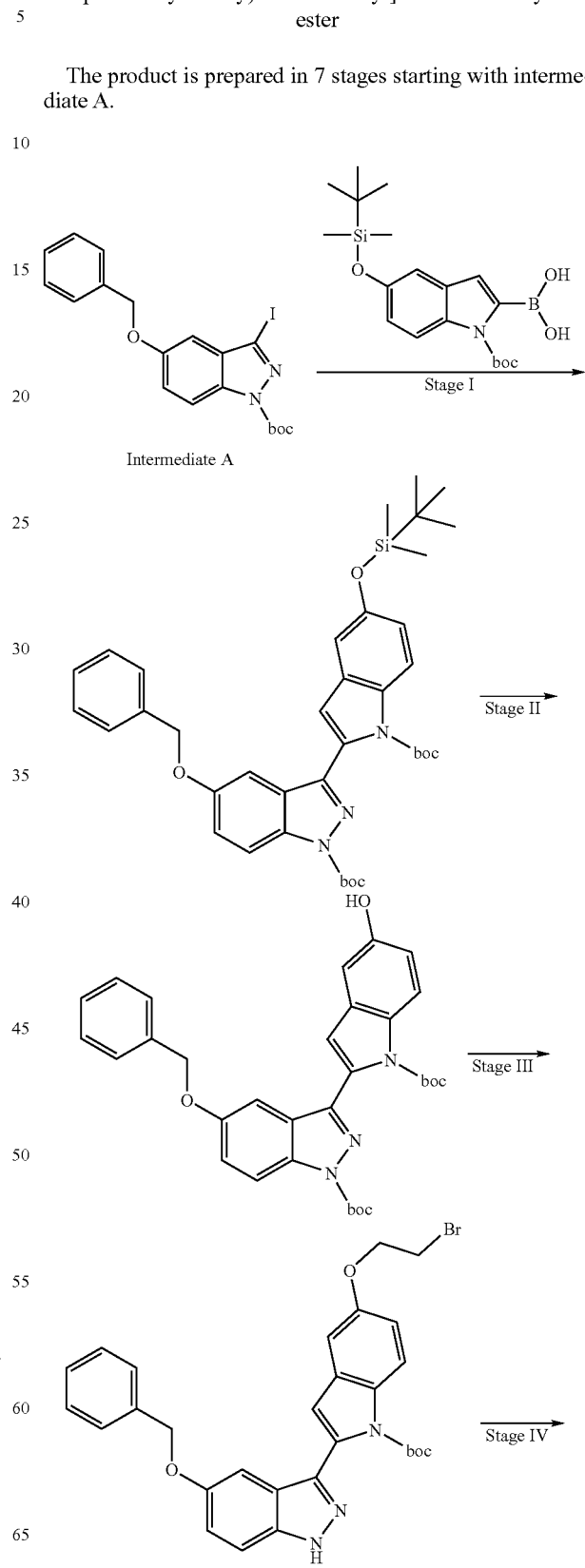

Stage I: Preparation of 5-benzyloxy-3-[1-tert-butoxycarbonyl-5-(tert-butyl-dimethylsilanyloxy)-1H-indol-2-yl]indazole-1-carboxylic acid tert-butyl ester
(Procedure M)

13 g of 1-(tert-butyldimethylsilyloxy)-5-indole-2-boronic acid, 28.9 g of cesium carbonate, 906.5 mg of [1.1'-bis(diphenylphosphino)ferrocene]-dichloropalladium II as a complex with dichloromethane and then 51 ml of distilled water are added successively to a solution of 10 g of 5-benzyloxy-3-iodoindazole-1-carboxylic acid tert-butyl ester (intermediate A) in 156 ml of dioxane. The reaction mixture is heated for 45 minutes by means of an oil bath preheated to 100° C. The mixture is cooled to ambient temperature by means of a water bath. The medium is separated by settling out. The lower phase is discarded (approximately 50 ml) and the organic phase is concentrated under vacuum. The brown gum obtained is solubilized in 250 ml of dichloromethane and the organic phase is washed with 3 times of 50 ml of distilled water. The organic phase is dried over magnesium sulfate and activated charcoal and then filtered through paper and concentrated in a rotary evaporator. The reaction crude is purified by flash chromatography on 500 g of 40-63 μm silica, eluting with a 40/60 cyclohexane/dichloromethane mixture to obtain 13.4 g of 5-benzyloxy-3-[1-tert-butoxycarbonyl-5-(tert-butyldimethylsilanyloxy)-1H-indol-2-yl]indazole-1-carboxylic acid tert-butyl ester.

Stage II: Preparation of 5-benzyloxy-3-(1-tert-butoxycarbonyl-5-hydroxy-1H-indol-2-yl)indazole-1-carboxylic acid tert-butyl ester A solution of 13.4 g of 5-benzyloxy-3-[1-tert-butoxycarbonyl-5-(tert-butyl-dimethylsilanyloxy)-1H-indol-2-yl]indazole-1-carboxylic acid tert-butyl ester and 6.15 g of tetrabutylammonium fluoride in 140 ml of anhydrous tetrahydrofuran is stirred at ambient temperature for 30 minutes. The solvent is evaporated off under vacuum. The reaction crude is taken up with 50 ml of dichloromethane and the organic phase is washed with 2 times 25 ml of distilled water. The organic phase is dried over magnesium sulfate. After filtration and concentration under vacuum, the reaction crude is purified by flash chromatography on 450 g of 40-63 μm silica. Elution is carried out with 100% dichloromethane and then a 98/2 then 95/5 dichloromethane/methanol mixture to Obtain 8.54 g of 5-benzyloxy-3-(1-tert-butoxycarbonyl-5-hydroxy-1H-indol-2-yl)indazole-1-carboxylic acid tert-butyl ester.

Analytical LC/MS: Tr=4.75 min; [M+H]$^+$=446.34

Stage III: Preparation of 5-benzyloxy-3-[5-(2-bromoethoxy)-1tert-butoxycarbonyl-1H-indol-2-yl]indazole-1-carboxylic acid tert-butyl ester 2.22 g of 5-benzyloxy-3-(1-tert-butoxycarbonyl-5-hydroxy-1H-indol-2-yl)-indazole-1-carboxylic acid tert-butyl ester and 7.8 g of cesium carbonate, in 22 ml of dibromoethane, are stirred at 80° C. (temperature of the oil bath) for 48 hours. The reaction mixture is filtered through sintered glass and the solid is rinsed with 20 ml of dichloromethane. The filtrate is concentrated under vacuum. The reaction crude is purified by flash chromatography on 160 g of silica. The eluent is 100% dichloromethane. 2 g of 5-benzyloxy-3-[5-(2-bromo-ethoxy)-1-tert-butoxycarbonyl-1H-indol-2-yl]indazole-1-carboxylic acid tert-butyl ester are isolated.

Stage IV: Preparation of 5-benzyloxy-3-[1-tert-butoxycarbonyl-5-(2-morpholin-4-ylethoxy)-1H-indol-2-yl]indazole-1-carboxylic acid tert-butyl ester (Procedure N)

2.0 g of 5-benzyloxy-3-[5-(2-bromoethoxy)-1-tert-butoxycarbonyl-1H-indol-2-yl]indazole-1-carboxylic acid tert-butyl ester are stirred in 90 ml of acetonitrile. 498 mg of potassium iodide are added and the suspension is heated to 80° C. After 7 h 20 min, the following reactants are successively added: 394 μl of morpholine, 1.24 g of potassium carbonate, 150 mg of potassium iodide. The suspension is heated at 80° C. overnight. The insoluble material is filtered off and the filtrate is concentrated under vacuum. The reaction crude is taken up in 50 ml of dichloromethane. The organic phase is washed with 2 times 25 ml of distilled water. The organic phase is dried over magnesium sulfate and filtered. The solvent is evaporated off in a rotary evaporator to obtain 1.90 g of 5-benzyloxy-3-[1-tert-butoxycarbonyl-5-(2-morpholin-4-ylethoxy)-1H-indol-2-yl]-indazole-1-carboxylic acid tert-butyl ester.

Analytical LC/MS : Tr=3.99 min ; [M+H]$^+$=669.43.

Stage V: Preparation of 5-benzyloxy-3-[5-(2-morpholin-4-ylethoxy)-1H-indol-2-yl]-1H-indazole 1.0 g of 5-benzyloxy-3-[1-tert-butoxycarbonyl-5-(2-morpholin-4-ylethoxy)-1H-indol-2-yl]indazole-1-carboxylic acid tert-butyl ester are stirred at ambient temperature for 18 hours in 6 ml of a 4M hydrochloric acid solution in dioxane. The product is filtered through sintered glass, and rinsed with dioxane to obtain 692.4 mg of 5-benzyloxy-3-[5-(2-morpholin-4-ylethoxy)-1H-indol-2-yl]-1H-indazole.

Analytical LC/MS: Tr=3.05 min; [M+H]$^+$=469.34.

Stage VI: Preparation of 3-[5-(2-morpholin-4-ylethoxy)-1H-indol-2-yl]-1H-indazol-5-ol 1.12 g of 5-benzyloxy-3-[5-(2-morpholin-4-ylethoxy)-1H-indol-2-yl]-1H-indazole are dissolved in 55 ml of absolute ethanol and then 424 mg of palladium-on-charcoal, 587 mg of ammonium formate and 227 μl of triethylamine are successively added. The reaction medium is stirred at 67° C. (internal temperature of the suspension). A substantial amount of gas is seen to be given off. After stirring for one hour, the medium is filtered through paper and the catalyst is rinsed with absolute ethanol. The filtrate is concentrated under vacuum to obtain 558 mg of 3-[5-(2-morpholin-4-ylethoxy)-1H-indol-2-yl]-1H-indazol-5-ol.

Analytical LC/MS: Tr=2.29 min; [M+H]$^+$=379.37.

Stage VII: Preparation of methylphosphonic acid methyl ester 3-[5-(2-morpholin-4-ylethoxy)-1H-indol-2-yl]-1H-indazol-5-yl ester A suspension of 170 mg of methylphosphonic acid bis-(4-nitrophenyl)ester (prepared according to procedure E) and 189.7 mg of 3-[5-(2-morpholin-4-yl-ethoxy)-1H-indol-2-yl]-1H-indazol-5-ol in 17 ml of dichloromethane (stabilized with amylene) is stirred at ambient temperature. A solution of 75 μl of DBU in 500 μl of dichloromethane is added dropwise over 10 minutes. Stirring is maintained overnight. 204 μl of methanol are added with 75 μl of DBU. The solution is stirred for 24 hours. The reaction medium is concentrated under vacuum and the crude is then taken up with 25 ml of ethyl acetate and washed with 4 times 25 ml of distilled water. The organic phase is dried over magnesium sulfate, filtered and concentrated under vacuum. The reaction crude is purified by flash chromatography on 5 g of 40-63 μm silica. Eluents: 98/2 then 95/5 dichloromethane/methanol. 95 mg of methylphosphonic acid methyl ester 3-[5-(2-morpholin-4-yl-ethoxy)-1H-indol-2-yl]-1H-indazol-5-yl ester are collected.

Analytical LC/MS: Tr=2.25 min; [M+H]$^+$=471.11.

Example 29

Methylphosphonic acid 3-[6-(2-diethylaminoethoxy)-1H-indol-2-yl]-1-indazol-5-yl ester methyl ester The title compound is prepared in 10 stages according to scheme 7 below:

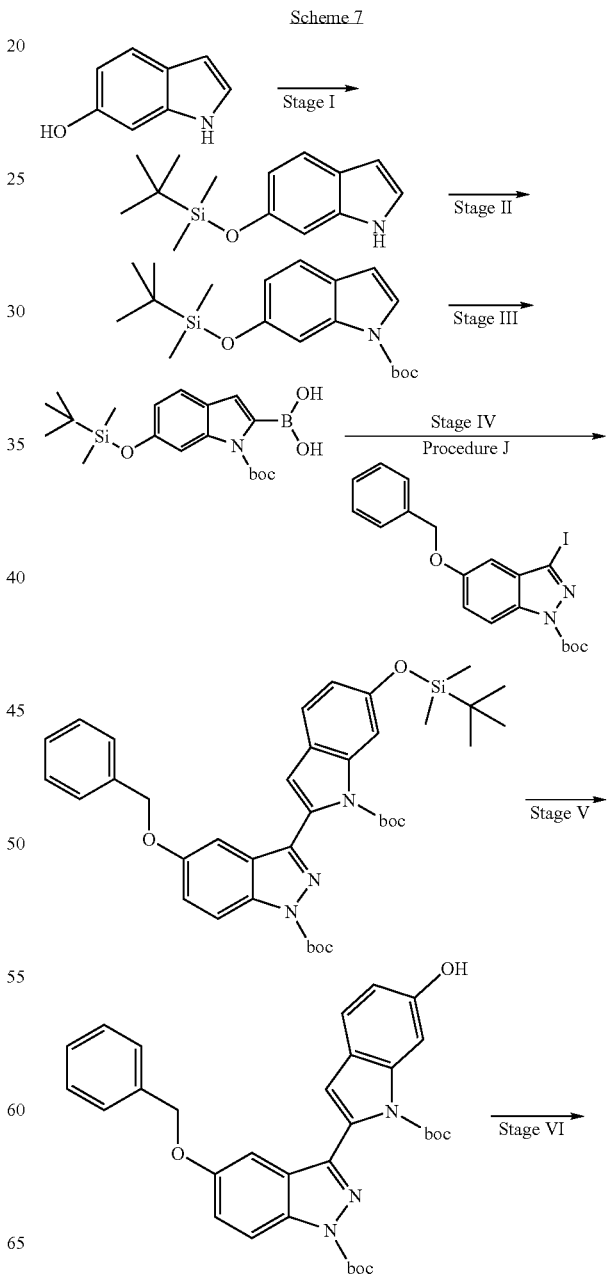

Scheme 7

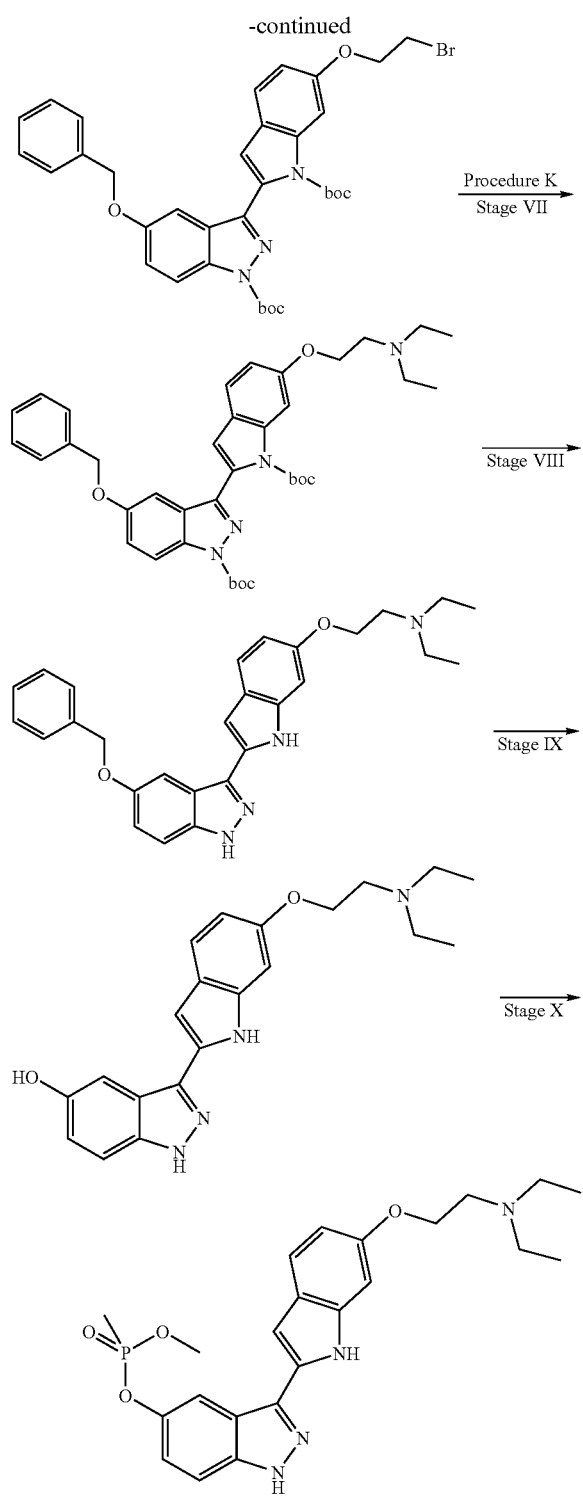

distilled water. The organic phase is dried over magnesium sulfate and filtered, and the solvent is evaporated off in a rotary evaporator to obtain 6.5 g of 6-(tert-butyl-dimethylsilanyloxy)-1H-indole.

Analytical LC/MS: Tr=4.55 min; $[M+H]^+$=248.30.

Stage II: Preparation of 6-(tert-butyldimethylsilanyloxy)indole-1-carboxylic acid tert-butyl ester A solution of 6.5 g of 6-(tert-butyldimethylsilanyloxy)-1H-indole, 9.23 g of di-tert-butyl dicarbonate and 646 mg of 4-dimethylaminopyridine in 65 ml of dichloromethane is stirred at ambient temperature. After stirring for 4 hours, the solvent is evaporated off in a rotary evaporator and the reaction crude is purified by flash chromatography on 35-70 µm silica, eluent: cyclohexane to isolate 9.20 g of 6-(tert-butyldimethylsilanyloxy)indole-1-carboxylic acid tert-butyl ester in the form of a yellow oil.

Analytical LC/MS: Tr=6.0 min; $[M+H]^+$=348.3.

Stage III: Preparation of 6-(tert-butyldimethylsilanyloxy)indole-1-carboxylic acid tert-butyl 3-boronic acid A solution of 8.20 g of 6-(tert-butyldimethylsilanyloxy)indole-1-carboxylic acid tert-butyl ester in 120 ml of anhydrous tetrahydrofuran is cooled to −78° C. by means of a bath of dry ice in acetone. 19 ml of 1.5 M tert-butyllithium in pentane are added dropwise over 40 minutes. The solution is stirred at −78° C. for 30 minutes. 5.3 ml of trimethyl borate are then added. After the medium has been reheated to 0° C., the solution is stirred at this temperature for 2 hours. 75 ml of a saturated aqueous ammonium chloride solution are added, along with 200 ml of ethyl ether. The medium is stirred for 20 minutes at ambient temperature. After acidification of the medium with 60 ml of a 10% aqueous NaHSO$_4$ solution and 2 ml of concentrated sulfuric acid, the organic phase is separated by settling out and washed with 120 ml of distilled water and 120 ml of a saturated aqueous sodium chloride solution. After drying over magnesium sulfate and filtration, the solvent is evaporated off. The solid obtained is washed with cyclohexane spin-filtered through sintered glass to collect 5.79 g of 6-(tert-butyidimethylsilanyloxy)indole-1-carboxylic acid tert-butyl 3-boronic acid.

Stage IV: Preparation of 5-benzyloxy-3-[1-tert-butoxycarbonyl-6-(tert-butyl-dimethylsilanyloxy)-1H-indol-2-yl]indazole-1-carboxylic acid tert-butyl ester The compound is prepared according to procedure M using 5.12 g of intermediate A, 5.79 g of 6-(tert-butyldimethylsilanyloxy)indole-1-carboxylic acid tert-butyl 3-boronic acid, 466 mg of [1.1'-bis-diphenylphospino)ferrocene]dichloropalladium 11 as a complex with dichloromethane, and 14.82 g of cesium carbonate in suspension in a water (30 ml) and dioxane (70 ml) mixture. The reaction medium is heated at 105° C. for 1 h 30 min. After treatment, the reaction crude is purified by flash chromatography on 35-70 µm silica, eluent: cyclohexane to obtain 5.56 g of 5-benzyloxy-3-[1-tert-butoxycarbonyl-6-(tert-butyldimethylsilanyloxy)-1H-indol-2-yl]indazole-1-carboxylic acid tert-butyl ester.

Stage I: Preparation of 6-(tert-butyldimethylsilanyloxy)-1H-indole

A solution of 3.52 g of 6-hydroxyindole, 4.78 g of tert-butyldimethylsilyl chloride, and 4.5 g of imidazole in 16 ml of dimethylformamide is stirred at ambient temperature overnight. The reaction medium is diluted with ethyl acetate and the organic phase is then washed with 2 times 50 ml of

Stage V: Preparation of 5-benzyloxy-3-(1-tert-butoxycarbonyl-6-hydroxy-1H-indol-2-yl)indazole-1-carboxylic acid tert-butyl ester 1.50 g of 5-benzyloxy-3-[1-tert-butoxycarbonyl-6-(tert-butyldimethyl-silanyloxy)-1H-indol-2-yl]indazole-1-carboxylic acid tert-butyl ester in solution in 35 ml of tetrahydrofuran with 770 mg of tetrabutylammonium fluoride hydrate are stirred at ambient temperature. After stirring for 1 h 30 min, the medium is diluted with dichloromethane and the organic phase is then washed with distilled water. After drying over magnesium sulfate and filtration, the solvent is evaporated off under vacuum in a rotary evaporator to obtain 1.05 g of 5-benzyloxy-3-(1-tert-butoxycarbonyl-6-hydroxy-1H-indol-2-yl)indazole-1-carboxylic acid tert-butyl ester.

Analytical LC/MS: Tr=4.73 min; [M+H]$^+$=556.06.

Stage VI: Preparation of 5-benzyloxy-3-[6-(2-bromoethoxy)-1tert-butoxycarbonyl-1H-indol-2-yl]indazole-1-carboxylic acid tert-butyl ester A solution of 1.05 g of 5-benzyloxy-3-(1-tert-butoxycarbonyl-6-hydroxy-1-indol-2-yl)indazole-1-carboxylic acid tert-butyl ester in 10.4 ml of dibromoethane is stirred at ambient temperature. 1.85 g of cesium carbonate are added and the medium is heated at 80° C. for 24 h. The solvent is evaporated off and the crude is taken up with a water/ethyl acetate mixture. The organic phase is dried over magnesium sulfate. After filtration, the solvent is evaporated off in a rotary evaporator. The reaction crude is purified by flash chromatography on a cartridge of 50 g of silica, with a cyclohexane/ethyl acetate gradient of 95/5 to 65/35 over 60 minutes to collect 1.23 g of 5-benzyloxy-3-[6-(2-bromoethoxy)-1-tert-butoxycarbonyl-1H-indol-2-yl]-indazole-1-carboxylic acid tert-butyl ester.

Analytical LC/MS: Tr=5.43 min; [M+H]$^+$=664.04.

Stage VII: The compound 5-benzyloxy-3-[1-tert-butoxycarbonyl-6-(2-diethylaminoethoxy)-1H-indol-2-yl]indazole-1-carboxylic acid tert-butyl ester is prepared according to procedure N using 1.23 g of 5-benzyloxy-3-[6-(2-bromoethoxy)-1-tert-butoxycarbonyl-1H-indol-2-yl]indazole-1-carboxylic acid tert-butyl ester, 50 ml of acetonitrile, 401 mg of potassium iodide, 204 mg of diethylamine, and 770 mg of cesium carbonate. After treatment, the reaction crude is purified by chromatography on a cartridge of 20 g of silica; eluent: 98/2, 95/5, 92/8 dichloromethane/methanol to obtain 390 mg of 5-benzyloxy-3-[1-tert-butoxycarbonyl-6-(2-diethylaminoethoxy)-1H-indol-2-yl]indazole-1-carboxylic acid tert-butyl ester.

Analytical LC/MS: Tr=4.62 min; [M+H]$^+$=655.45.

Stage VIII: The compound {2-[2-(5-benzyloxy-1H-indazol-3-yl)-1H-indol-6-yloxy]ethyl}diethylamine is prepared in the following way: 390 mg of 5-benzyloxy-3-[1-tert-butoxycarbonyl-6-(2-diethylaminoethoxy)-1H-indol-2-yl]-indazole-1-carboxylic acid tert-butyl ester in solution in 5 ml of dichloromethane and 2 ml of trifluoroacetic acid are stirred at ambient temperature for 20 hours. The solvent is evaporated off under vacuum in a rotary evaporator to obtain 480 mg of {2-[2-(5-benzyloxy-1H-indazol-3-yl)-1-indol-6-yloxy]ethyl}diethylamine in the form of a trifluoroacetate salt.

Analytical LC/MS: Tr=3.87 min; [M+H]$^+$=455.51.

Stage IX: The compound 3-[6-(2-diethylaminoethoxy)-1H-indol-2-yl]-1-indazol-5-ol is prepared in the following way: 990 mg of {2-[2-(5-benzyloxy-1H-indazol-3-yl)-1H-indol-6-yloxy]ethyl}diethylamine in solution in 15 ml of absolute ethanol in the presence of 100 mg of palladium-on-charcoal and 1.1 g of ammonium formate are heated in a microwave oven at atmospheric pressure at 90° C. for 30 minutes. The reaction crude is filtered through celite, the catalyst is rinsed with absolute ethanol and the filtrate is concentrated under vacuum. The reaction crude is taken up in 80 ml of ethyl acetate and washed with 2 times 50 ml of a saturated aqueous sodium bicarbonate solution. After drying over magnesium sulfate, the organic phase is concentrated to dryness. The solid obtained is washed with dichloromethane and with isopropyl ether to collect 280 mg of 3-[6-(2-diethylaminoethoxy)-1H-indol-2-yl]-1H-indazol-5-ol.

Stage X: The compound methylphosphonic acid 3-[6-(2-diethylamino-ethoxy)-1H-indol-2-yl]-1H-indazol-5-yl ester methyl ester is prepared as follows: 100 mg of 3-[6-(2-diethylaminoethoxy)-1H-indol-2-yl]-1H-indazol-5-ol in solution in 4 ml of dichloromethane with 93 mg of methylphosphonic acid bis-(4-nitrophenyl)ester (prepared according to procedure E) are stirred at ambient temperature. A solution of 41 µl of 1,8-diazabicyclo[5.4.0]undec-7-ene (DBU) in 1 ml of dichloromethane is added dropwise. The solution is stirred overnight at ambient temperature. 41 µl of DBU, followed by 115 µl of methanol, are then added. This operation is repeated after stirring for 4 h 15 min. After stirring for another hour at ambient temperature, the solvent is evaporated off and the crude is purified by flash chromatography on a cartridge of 25 g of silica, eluent: dichloromethane/methanol, 90/10 to 60/40 in steps. The fractions obtained are concentrated and purified by preparative LC/MS to isolate 30 mg of methylphosphonic acid 3-[6-(2-diethylaminoethoxy)-1H-indol-2-yl]-1H-indazol-5-yl ester methyl ester in the form of a colorless oil.

NMR spectrum: From 0.99 to 1.18 (m, 6H); 1.70 (d, J=17.0 Hz, 3H); 2.63 (broad m, 4H); 2.85 (broad m, 2H); 3.78 (d, J=11.0 Hz, 3H); 4.05 (broad m, 2H); 6.78 (broad d, J=9.0 Hz, 1H); 6.97 (broad m, 2H); 7.30 (broad d, J=9.0 Hz, 1H); 7.48 (d, J=9.0 Hz, 1H); 7.60 (d, J=9.0 Hz, 1H); 7.89 (broad m, 1H); 11.4 (broad m, 1H); 13.3 (broad s, 1H).

Example 30

Ethylphosphonic acid 3-(1H-indol-2-yl)-1H-indazol-5-yl ester methyl ester

The ethylphosphonic acid bis(nitrophenyl)ester intermediate is prepared according to procedure E using 528 mg of ethylphosphonic dichloride, 1 g of p-nitrophenol, 345 mg of sodium hydride (50% in oil) and 10 ml of tetrahydrofuran. 1.29 g of ethylphosphonic acid bis(nitrophenyl) ester are collected.

The compound ethylphosphonic acid 3-(1H-indol-2-yl)-1H-indazol-5-yl ester methyl ester is prepared according to procedure F using 282.5 mg of ethylphosphonic acid bis (nitrophenyl), 200 mg of 3-(1H-indol-2-yl)-H-indazol-5-ol (intermediate B) in solution in 10 ml of dichloromethane, and 120 µl of 1,8-diazabicyclo[5.4.0]undec-7-ene (DBU). After 7 hours at ambient temperature, 120 µl of DBU and 144.5 µl of methanol are added and the mixture is left at ambient temperature overnight. After concentration, the crude is purified by chromatography on a cartridge of 50 g of silica. Eluent: cyclohexane/ethyl acetate 9/1 in stages to ethyl acetate/methanol 9/1. The solid derived from concentrating the fractions containing the expected compound is washed with ethyl acetate and then with ethyl ether to obtain 83 mg of ethylphosphonic acid 3-(1H-indol-2-yl)-1H-indazol-5-yl ester methyl ester.

$^1$H NMR spectrum at 400 MHz on a Bruker Avance DRX-400 spectrometer with chemical shifts (δ in ppm)—in the solvent dimethyl sulfoxide—d6 (DMSO-d6) reference at 2.50 ppm:

1.17 (td, J=7.0 and 20.0 Hz, 3H); from 1.95 to 2.07 (m, 2H); 3.77 (d, J=11.0 Hz, 3H); from 6.98 to 7.07 (m, 2H); 7.15 (broad t, J=8.0 Hz, 1H); 7.33 (broad d, J=8.0 Hz, 1H); 7.46 (broad d, J=8.0 Hz, 1H); from 7.58 to 7.65 (m, 2H); 7.92 (broad s, 1H); 11.6 (broad m, 1H); 13.45 (broad m, 1H).

Example 31

Methylphosphonothioic acid O-[3-(1H-indol-2-yl)-1H-indazol-5-yl] ester O-methyl ester The methylphosphonothioic acid O,O-bis-(4-nitrophenyl) ester intermediate is prepared according to procedure E using 536 mg of methylphosphonothioic dichloride, 345 mg of sodium hydride (50% in oil), 1 g of p-nitrophenol and 10 ml of tetrahydrofuran. 1.19 g of expected product are collected.

The compound methylphosphonothioic acid O-[3-(1H-indol-2-yl)-1H-indazol-5-yl]ester O-methyl ester is prepared according to procedure F using 200 mg of 3-(1H-indol-2-yl)-H-indazole-5-ol (intermediate B) in solution with 284 mg of methylphosphonothioic acid O,O—bis-(4-nitrophenyl)ester in 6 ml of dichloromethane (stabilized with amylene), to which 120 µl of 1,8-diazabicyclo[5.4.0]undec-7-ene (DBU) in solution in 1 ml of dichloromethane are added. After stirring at ambient temperature for 4 h 30 min, 325 µl of methanol and 120 µl of DBU in solution in 1 ml of dichloromethane are added. The mixture is left at ambient temperature overnight and the solvent is then evaporated off and the crude is purified by flash chromatography on 35-70 µm silica, eluent: cyclohexane/ethyl acetate 90/10 to 50/50. The fractions obtained are concentrated and purified by preparative LC/MS to obtain 47.7 mg of methylphosphonothioic acid O-[3-(1H-indol-2-yl)-1H-indazol-5-yl]ester O-methyl ester.

$^1$H NMR spectrum at 400 MHz on a Bruker Avance DRX-400 spectrometer with chemical shifts (δ in ppm)—in the solvent dimethyl sulfoxide—d6 (DMSO-d6) reference at 2.50 ppm.

2.11 (d, J=15.0 Hz, 3H); 3.81 (d, J=14.0 Hz, 3H); 7.02 (broad t, J=9.0 Hz, 1H); from 7.07 to 7.14 (m, 2H); 7.28 (broad d, J=9.0 Hz, 1H); 7.44 (broad d, J=9.0 Hz, 1H); from 7.58 to 7.65 (m, 2H); 7.49 (m, 1H); 11.6 (broad m, 1H); 13.35 (broad s, 1H).

Example 32

Cyclohexylphosphonic acid 3-(1H-indol-2-yl)-1H-indazol-5-yl ester methyl ester

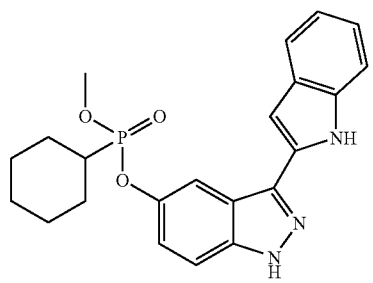

The cyclohexylphosphonic acid bis(nitrophenyl)ester intermediate is prepared according to procedure E using 722 mg of cyclohexylphosphonic dichloride, 1 g of p-nitrophenol, 345 mg of sodium hydride (50% in oil) and 10 ml of tetrahydrofuran. 1.47 g of expected compound are collected (quantitative yield)

The compound cyclohexylphosphonic acid 3-(1H-indol-2-yl)-1H-indazol-5-yl ester methyl ester is prepared according to procedure F using 200 mg of 3-(1H-indol-2-yl)-H-indazol-5-ol (intermediate B) in solution with 325 mg of cyclohexylphosphonic acid bis(nitrophenyl)ester in 6 ml of dichloromethane (stabilized with amylene), to which 120 µl of 1,8-diazabicyclo[5.4.0]undec-7-ene (DBU) in solution in 1 ml of dichloromethane are added. After stirring at ambient temperature for 4 hours 30 minutes, 325 µl of methanol in solution in 1 ml of dichloromethane are added. The mixture is left at ambient temperature overnight and the solvent is then evaporated off and the crude is purified by flash chromatography on 35-70 µm silica, eluent: cyclohexane/ethyl acetate 90/10 to 50/50. The fractions obtained are concentrated and purified by preparative LC/MS to obtain 64.5 mg of cyclohexylphosphonic acid 3-(1H-indol-2-yl)-1H-indazol-5-yl ester methyl ester.

NMR spectrum: chemical shifts (δ in ppm)—in the solvent dimethyl sulfoxide—d6 (DMSO-d6) reference at 2.50 ppm.

From 1.20 to 1.50 (m, 6H); from 1.62 to 1.83 (m, 3H); from 1.93 to 2.15 (m, 2H); 3.75 (d, J=11.0 Hz, 3H); from 6.96 to 7.05 (m, 2H); 7.11 (broad t, J=8.0 Hz, 1H); 7.31 (broad d, J=9.0 Hz, 1H); 7.45 (broad d, J=9.0 Hz, 1H); from 7.59 to 7.64 (m, 2H); 7.40 (m, 1H); 11.6 (broad m, 1H); 13.5 (broad m, 1H).

Example 33

Phenylphosphonic acid mono-[3-(1H-indol-2-yl)-1H-indazol-5-yl]ester

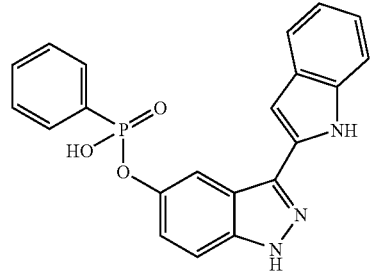

For the purpose of preparing the compound [3-(1H-indol-2-yl)-1H-indazol-5-ylmethyl]phenylphosphinic acid N-ethylamide, a solution of 150 mg of phenyl-phosphonic acid 3-(1H-indol-2-yl)-1H-indazol-5-yl ester 4-nitrophenyl ester (prepared according to procedure E) and 1.5 ml of diethylamine (2M solution in tetrahydrofuran) in dichloromethane (stabilized with amylene) is stirred at ambient temperature. 44 µl of 1,8-diazabicyclo[5.4.0]undec-7-ene (DBU) are added and the medium is stirred overnight at ambient temperature. The solvent is evaporated off in a rotary evaporator and the reaction crude is purified by preparative LC/MS so as to isolate a compound of mass [M+H]$^+$=390, which does not correspond to the expected product. A second fraction of 23 mg of a gray solid identified as phenylphosphonic acid mono-[3-(1H-indol-2-yl)-1H-indazol-5-yl]ester are collected.

Analytical LC/MS : Tr=2.72 min; [M+H]$^+$=390.27.

NMR spectrum : chemical shifts (δ in ppm)—in the solvent dimethyl sulfoxide—d6 (DMSO-d6) reference at 2.50 ppm:

For the main product of the mixture (70%), the following is obtained:

6.82 (broad s, 1H); 7.02 (broad t, J=8.5 Hz, 1H); 7.11 (broad t, J=8.5 Hz, 1H); 7.21 (broad d, J=9.0 Hz, 1H); 7.43

(broad d, J=9.0 Hz, 1H); from 6.90 to 7.62 (m, 5H); 7.76 (broad s, 1H); 7.82 (broad dd, J=8.5 and 12.5 Hz, 2H); 11.55 (broad m, 1H); 13,3 (broad s, 1H).

Experimental Protocols Regarding Biochemical Assays

1. FAK

The inhibitory activity of the compounds on FAK is determined by measuring the inhibition of the autophosphorylation of the enzyme using a time resolved fluorescence (HTRF) assay.

The complete cDNA of human FAK, the N-terminal end of which was tagged with histidine, was cloned into a baculovirus expression vector pFastBac HTc. The protein was expressed and purified to approximately 70% homogeneity.

The kinase activity was determined by incubating the enzyme (4.6 μg/ml) with various concentrations of test compound in a 50 mM Hepes buffer, pH=7.5, containing 5% glycerol 0.03% Triton x-100, 50 mM NaCI, 1 mM DTT, 5 mM $MgCl_2$, 5 μM of ATP and a final concentration of 1% DMSO, for 10 minutes at 37° C. The enzyme reaction was stopped by adding 320 mM EDTA, and the labeling was carried out in a 100 mM Hepes buffer, pH=7,5, containing 0.8 mM KF and 0.2% BSA, overnight at 4° C., by adding to this buffer an anti-histidine antibody labeled with XL665 and a tyrosine-phosphospecific monoclonal antibody conjugated to europium cryptate (Eu-K). The characteristics of the two fluorophores are available in G. Mathis et al., Anticancer Research, 1997, 17, pages 3011-3014. The energy transfer between the excited europium cryptate and the acceptor XL665 is proportional to the degree of autophosphorylation of FAK. The long-lasting XL-665-specific signal was measured in a Packard Discovery plate counter. All the assays were carried out in duplicate and the mean of the two assays was calculated. The inhibition of the autophosphorylation activity of FAK with compounds of the invention is expressed as percentage inhibition relative to a control, the activity of which is measured in the absence of test compound. The [signal at 665 nm/signal at 620 nm] ratio is taken into consideration in calculating the % inhibition.

2. KDR

The inhibitory effect of the compounds is determined in an in vitro KDR enzyme substrate phosphorylation assay using a scintillation technique (96-well plate, NEN).

The cytoplasmic domain of the human KDR enzyme was cloned in the form of a GST fusion into the baculovirus expression vector pFastBac. The protein was expressed in SF21 cells and purified to approximately 60% homogeneity.

The kinase activity of KDR was measured in 20 mM MOPS, 10 mM $MgCl_2$, 10 mM $MnCl_2$, 1 mM DTT, 2.5 mM EGTA and 10 mM β-glycerophosphate, pH=7.2, in the presence of 10 mM $MgCl_2$, 100 μM $Na_3VO_4$ and 1 mM NaF. 10 μl of the compound were added to 70 μl of kinase buffer containing 100 ng of KDR enzyme KDR at 4° C. The reaction was initiated by adding 20 μl of solution containing 2 μg of substrate (SH2-SH3 fragment of PLC γ expressed in the form of a GST fusion protein), 2 μCi γ $^{33}$P[ATP] and 2 μM cold ATP. After incubation for 1 hour at 37° C., the reaction was stopped by adding 1 volume (100 μl) of 200 mM EDTA. The incubation buffer was removed, and the wells were washed three times with 300 μl of PBS. The radioactivity was measured in each well using a Top Count NXT radioactivity counter (Packard).

The background noise was determined by measuring the radioactivity in four different wells containing the radioactive ATP and the substrate alone.

A total activity control was measured in four different wells containing all the reactants ($\gamma^{33}$P-[ATP], KDR and PLCy substrate) but in the absence of compound.

The inhibition of the KDR activity with the compound of the invention is expressed as percentage inhibition of the control activity determined in the absence of compound.

The compound SU5614 (Calbiochem) (1 μM) was included in each plate as an inhibition control.

3. Aurora2

The inhibitory effect of compounds with respect to the Aurora2 kinase is determined by means of a radioactivity scintillation assay using nickel chelate.

A complete recombinant Aurora2 enzyme, the N-terminal end of which had been tagged with histidine, was expressed in E. coli and purified to a quality close to homogeneity.

The C-terminal fragment (Q1687-H2101) of an NuMA (Nuclear Mitotic Apparatus protein) expressed in E. coli, and the N-terminal end of which had been tagged with histidine, was purified by nickel chelate chromatography and used as substrate in the Aurora2 kinase assay.

To determine the kinase activity, the NuMA substrate was equilibrated by chromatography on a Pharmacia PD10 column, in a buffer (50 mM Tris-HCl, pH 7.5, 50 mM NaCl, 10 mM $MgCl_2$) to which 10% (v/v) of glycerol and 0.05% (w/v) of NP40 had been added.

The Aurora2 kinase activity was measured by scintillation with nickel chelate (New England Nuclear, model SMP107). Each well contained 100,μl of the following solution: 0.02 μM of Aurora2; 0.5 μM of NuMA substrate; 1 μM of ATP to which 0.5 μCi of ATP-[33P] had been added. The solutions were incubated for 30 minutes at 37° C. The assay buffer was then removed and the wells were rinsed twice with 300 μl of kinase buffer. The radioactivity was measured in each well using a Packard Model Top Count NXT device.

The background noise is deduced from the radioactivity measurement taken by measuring, in duplicate, in wells containing radioactive ATP alone, containing buffered kinase treated in the same way as the other samples.

The measurement of the activity of the control is carried out in duplicate by measuring the radioactivity in the complete assay mixture (ATP, Aurora2 and NuMA substrate), in the absence of test compound.

The inhibition of the activity of Aurora2 with a compound of the invention is expressed as percentage inhibition of the control activity in the absence of test compound. Staurosporine is added to each plate as an inhibition control.

4. CDK2/cyclin E:

Purification of the CDK2/cyclin E-$(His)_6$ complex by IMAC (Immobilized Metal Affinity Chromatography):

Two recombinant baculoviruses carrying the human sequences encoding, respectively, CDK2 and cyclin E (the latter comprising a C-terminal hexahistidine tag) are used to co-infect Sf21 insect cells. Two to three days after the beginning of co-infection, the cells are harvested by centrifugation and then stored at −40° C. until they are used. After thawing and mechanical lysis of the cells, the complex present in the lysis supernatant is purified by nickel affinity chromatography (IMAC), and stored at −80° C.

CDK2/cyclin E Flashplate Assay in 96-well Format

A format using 96-well plates with wells coated with streptavidin is used to assay the activity of the compounds on the kinase activity of CDK2/cyclin E.

In order to carry out this assay, the biotinylated peptide substrate, fragment of the pRb protein (biotinyl-SACPLN-LPLQNNHTAADMYLSPVRSPKKKGSTTR-OH), is solubilized at the concentration of 1 mM in kinase buffer (HEPES/NaOH 50 mM, NaCl 1 mM, MgCl$_2$ 5 mM; pH 7.5) in order to constitute a stock solution that is conserved at −20° C. in the form of 110 μl aliquots. On the day of the experiment, an aliquot of this solution is thawed and diluted in kinase buffer containing 1 mM of dithiothritol, which is added to the buffer extemporaneously in order to obtain a concentration of 14.3 μM. 70 μl of this solution are added to each well of the Flashplate in order to obtain a final substrate concentration of 10 μM during the enzyme reaction carried out in a final volume of the reaction medium of 100 μl (cf. hereinafter).

Intermediate dilutions of inhibitors (products of the invention) at various concentrations are prepared in DMSO from stock solutions at 10 mM in separate tubes. Dilutions at 1000 μM, 333.3 μM, 111.1 μM, 37.03 μM, 12.35 μM, 4.11 μM and 1.37 μM are thus prepared. One μl of each of these solutions (or 1 μl of DMSO for the controls) is transferred into the wells of the assay plate.

19 μl of a solution of a mixture of adenosine triphosphate (ATP) and of ATPγ$^{33}$P in the kinase buffer at a concentration of 5.26 μM of total ATP and of 52.6 μCi/ml of $^{33}$P are then added to each well. The enzyme reaction is triggered by adding 10 μl per well of a solution of CDK2/cyclin E at 200 nM in the kinase buffer containing 1 mM of dithiothritol (or 10 μl of kinase buffer containing 1 mM of dithiothritol for the reaction blanks).

After the addition of each of the reactants, the final volume of each well is 100 μl, the final concentration of substrate is 10 μM, the final concentrations of inhibitors are 10 μM, 3.33 μM, 1.11 μM, 0.37 μM, 0.123 μM, 0.041 μM and 0.014 μM (according to the concentration of the intermediate dilution), the final concentration of ATP is 1 μM, the final amount of $^{33}$P is 1 μCi/well, and the final concentration of CDK2/cyclin E complex is 20 nM.

After the addition of all the reactants, the assay plate is incubated at 30° C. with orbital shaking at 650 rpm.

When the incubation is over, the plate is washed three times with 300 μl per well of PBS (Phosphate Buffered Saline, pH=7.4 without calcium or magnesium, reference 10010-015, Gibco BRL). The incorporation of $^{33}$P into the peptide is quantified by scintillation counting with a Packard Topcount.NXT device. The inhibitory activity of the products of the invention is evaluated by measuring the concentration of inhibitor which gives a 50% decrease in enzyme activity (IC50).

5. Tie2

The coding sequence of human Tie2 corresponding to the amino acids of the intracellular domain 776-1124 was generated by PCR using the cDNA isolated from human placenta as a model. This sequence was introduced into a baculovirus expression vector pFastBacGT in the form of a GST fusion protein.

The inhibitory effect of the molecules is determined in an assay for phosphorylation of PLC by Tie2 in the presence of GST-Tie2 purified to approximately 80% homogeneity. The substrate is made up of the SH2-SH3 fragments of PLC expressed in the form of a GST fusion protein.

The kinase activity of Tie2 is measured in a 20 mM MOPS buffer, pH 7.2, containing 10 mM MgCl$_2$, 10 mM MnCl$_2$, 1 mM DTT and 10 mM of glycerophosphate. A reaction mixture composed of 70 μl of kinase buffer containing 100 ng of GST-Tie2 enzyme is deposited, per well, in a 96-well Flashplate kept on ice. 10 μl of the test molecule, diluted in DMSO at a maximum concentration of 10%, are then added. For a given concentration, each measurement is carried out in quadruplicate. The reaction is initiated by adding 20 μl of solution containing 2 μl of GST-PLC., 2 μM of cold ATP and 1 μCi of $^{33}$P[ATP]. After incubation for 1 hour at 37° C., the reaction is stopped by adding 1 volume (100 μl) of EDTA at 200 mM. After removal of the incubation buffer, the wells are washed three times with 300 μl of PBS. The radioactivity is measured on a Wallac MicroBeta1450.

The inhibition of the Tie2 activity is calculated and expressed as percentage inhibition relative to the control activity determined in the absence of compound.

The products of the examples according to the invention generally exhibit an activity on the various kinases, and particularly on Tie2 and Aurora-2, that is estimated by means of the concentration that inhibits 50% of the activity of the kinase between 3 nM and 500 nM.

| Example | Au2 IC$_{50}$ (nM) | CDK2 IC$_{50}$ (nM) | FAK IC$_{50}$ (nM) | KDR IC$_{50}$ (nM) | TIE2 IC$_{50}$ (nM) |
|---|---|---|---|---|---|
| 01 | 37 | 234 | 279 | 158 | 40 |
| 02 | 75 | 991 | 3525 | 508 | 518 |
| 03 | 20 | 142 | 816 | 310 | 3 |
| 04 | 99 | 586 | 2896 | 1634 | 22 |
| 05 | 15 | 394 | 48 | 141 | 11 |
| 06 | 15 | 184 | 740 | 288 | 48 |
| 07 | 24 | 959 | 9639 | 2048 | 162 |
| 08 | 53 | 3700 | 8300 | 5400 | 130 |
| 09 | 27 | 54 | 3019 | 344 | 138 |
| 10 | 9130 | >10000 | >10000 |  | >10000 |
| 11 | 90 | 199 | 1136 | 1250 | 229 |
| 12 | 140 | 290 | 10000 | 2033 | 2307 |
| 13 | 69 |  |  |  |  |
| 14 | 76 | 780 | 5881 | 1660 | 290 |
| 15 | 108 | 2260 | >10000 | >10000 | 4084 |
| 16 | 2200 | >10000 | >10000 | >10000 | 2211 |
| 17 | 770 |  |  |  |  |
| 18 | 20 | 33 | 7570 | 228 | 33 |
| 19 | 55 | 113 |  | 121 | 33 |
| 20 | 96 | 7772 |  | 1415 | 96 |
| 21 | 74 | 4467 |  | 133 | 214 |
| 22 | 64 | 152 |  | 174 | 44 |
| 23 | 24 | 249 |  | 442 | 30 |
| 24 | 24 | 142 |  | 364 | 22 |
| 25 | 41 | 578 |  |  |  |
| 26 | 730 | 3236 |  |  |  |
| 27 | 134 | 7561 |  | 1883 | 353 |
| 28 | 25 | 74 | 1444 | 205 | 119 |
| 29 | 17 | 128 |  | 122 | 13 |
| 30 | 15 | 87 | 4539 | 215 | 90 |
| 31 | 19 | 125 | 9990 | 296 | 99 |
| 32 | 26 | 1496 | 10000 | 999 | 119 |
| 33 | 10 | 291 | 316 | 577 | 17 |

What is claimed is:

1. A compound of formula (I) below:

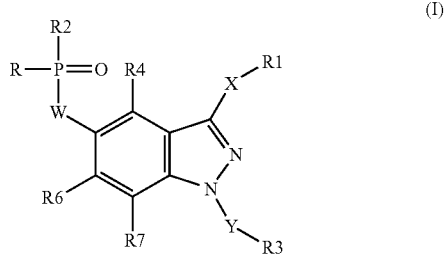

wherein

W is a covalent bond or O;

X is a covalent bond or a group chosen from —C=O—NR$_a$—, NR$_a$—C=O, —(CH$_2$)$_n$—, —CH=CH—, —C≡C—, —NR$_a$—, S, O, —SO$_2$—, —SO, —CO or —COO, wherein R$_a$ is H or (C$_1$-C$_4$)alkyl which optionally forms a ring with R1, and wherein n is an integer from 0 to 12;

R1 is H, alkyl, cycloalkyl, aryl or heteroaryl; said alkyl, cycloalkyl, aryl or heteroaryl is optionally substituted;

R and R2 may be identical or different and are independently of each other selected from H, alkyl, cycloalkyl, heterocycloalkyl, aryl, heteroaryl, hydroxyl, alkoxy and aryloxy radicals, all of which except H are optionally substituted;

Y is a covalent bond or a radical chosen from: —C=O—NR$_a$—, —C=O—O—, —C=O—, —(CH$_2$)$_n$— or —SO$_2$—, wherein R$_a$ is H or (C$_1$-C$_4$)alkyl which optionally forms a ring with R3 and n is as defined above;

R3 is selected from the group consisting of H, alkyl, cycloalkyl, aryl, and heteroaryl; all of which except H are optionally substituted;

R4, R6 and R7, which may be identical or different, are independently chosen from H, halogen, (C$_1$-C$_4$)alkyl, (C$_1$-C$_4$)alkoxy, cyano, —N(R$_b$)R$_c$, —C=O—N(R$_b$)R$_c$ and —N(R$_b$)—CO—R$_c$, wherein R$_b$ and R$_c$ are independently chosen from H, (C$_1$-C$_4$)alkyl and (C$_3$-C$_6$)cycloalkyl; or an enantiomer, a stereoisomer, a rotomer or a tautomer thereof, or a mixture in any combination thereof, a solvate thereof or a pharmaceutically acceptable salt thereof;

with the proviso that when X=—SO$_2$— or —SO—, R1 is not H;

when Y is —C=O—O—, or —SO$_2$—, R3 is not H; and with the exception of the products below

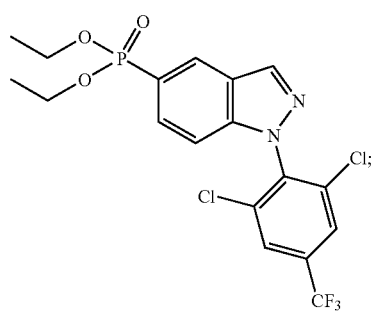

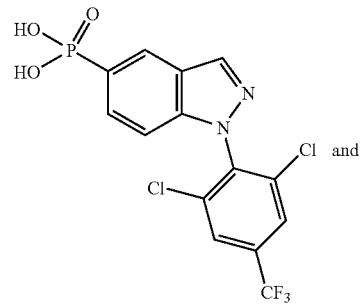

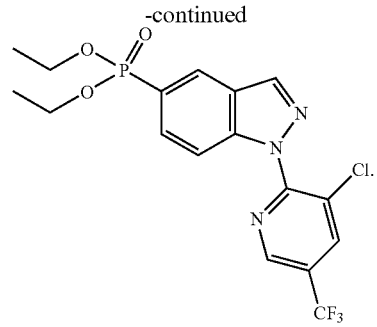

2. The compound as set forth in claim 1, wherein W is O.

3. The compound as set forth in claim 1, wherein the aryl and heteroaryl are independently chosen from:

(i) monocyclic radicals containing from zero to four hetero atoms chosen from O, N and S, and (ii) condensed bicyclic radicals comprising:

(a) a monocyclic radical containing 5, 6, 7 or 8 ring members and containing from zero to four hetero atoms chosen from O, N and S, condensed with (b) another ring containing 5 or 6 ring members, and containing from zero to three hetero atoms chosen from O, N and S.

4. The compound as set forth in claim 3, wherein the aryl or heteroaryl radicals are independently selected from the group consisting of: phenyl, pyridyl, pyrimidyl, triazinyl, pyrrolyl, imidazolyl, thiazolyl, furyl, thienyl, indolyl, indazolyl, azaindazolyl, isobenzofuranyl, isobenzothienyl, benzimidazolyl, benzoxazolyl, benzothiazolyl, arylvinylene, arylamido, arylcarboxamide, aralkylamine, quinolinyl, isoquinolinyl, cinnolyl, quinazolyl, naphthyridyl, triazolyl and tetrazolyl.

5. The compound as set forth in claim 4, wherein the aryl or heteroaryl radicals are independently selected from the group consisting of: phenyl, pyrrolyl, optionally substituted indolyl, and arylvinylene.

6. The compound as set forth in claim 1, wherein X is a covalent bond and R1 is heteroaryl.

7. The compound as set forth in claim 6, wherein R1 is indolyl.

8. The compound as set forth in claim 1, wherein R2 is (C$_1$-C$_4$)alkyl.

9. The compound as set forth in claim 1, wherein Y is a covalent bond and R3 is H.

10. A pharmaceutical composition comprising a compound of formula (I) below:

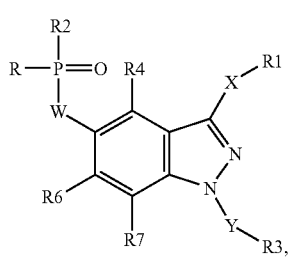

(I)

wherein
W is a covalent bond or O;
X is a covalent bond or a group chosen from —C=O—NR$_a$—, NR$_a$—C=O, —(CH$_2$)$_n$—, —CH=CH—, —C≡C—, —NR$_a$—, S, O, —SO$_2$—, —SO, —CO or —COO, wherein R$_a$ is H or (C$_1$-C$_4$)alkyl which optionally forms a ring with R1, and wherein n is an integer from 0 to 12;
R1 is H, alkyl, cycloalkyl, aryl or heteroaryl; said alkyl, cycloalkyl, aryl or heteroaryl is optionally substituted;
R and R2 may be identical or different and are independently of each other selected from H, alkyl, cycloalkyl, heterocycloalkyl, aryl, heteroaryl, hydroxyl, alkoxy and aryloxy radicals, all of which except H are optionally substituted;
Y is a covalent bond or a radical chosen from: —C=O—NR$_a$—, —C=O—O—, —C=O—, —(CH$_2$)$_n$— or —SO$_2$—, wherein R$_a$ is H or (C$_1$-C$_4$)alkyl which optionally forms a ring with R3 and n is as defined above;
R3 is selected from the group consisting of H, alkyl, cycloalkyl, aryl, and heteroaryl; all of which except H are optionally substituted;
R4, R6 and R7, which may be identical or different, are independently chosen from H, halogen, (C$_1$-C$_4$)alkyl, (C$_1$-C$_4$)alkoxy, cyano, —N(R$_b$)R$_c$, —C=O—N(R$_b$)R$_c$ and —N(R$_b$)—CO—R$_c$, wherein R$_b$ and R$_c$ are independently chosen from H, (C$_1$-C$_4$)alkyl and (C$_3$-C$_6$)cycloalkyl;
or an enantiomer, a stereoisomer, a rotomer or a tautomer thereof, or a mixture in any combination thereof, a solvate thereof or a pharmaceutically acceptable salt thereof, in combination with one or more pharmaceutically acceptable carriers, diluents or excipients.

11. The composition as set forth in claim 10, wherein W is O.

12. The composition as set forth in claim 10, wherein the aryl and heteroaryl are independently chosen from:
   (i) monocyclic radicals containing from zero to four hetero atoms chosen from O, N and S, and
   (ii) condensed bicyclic radicals comprising:
       (a) a monocyclic radical containing 5, 6, 7 or 8 ring members and containing from zero to four hetero atoms chosen from O, N and S, condensed with
       (b) another ring containing 5 or 6 ring members, and containing from zero to three hetero atoms chosen from O, N and S.

13. The composition as set forth in claim 12, wherein the aryl or heteroaryl radicals are independently selected from the group consisting of: phenyl, pyridyl, pyrimidyl, triazinyl, pyrrolyl, imidazolyl, thiazolyl, furyl, thienyl, indolyl, indazolyl, azaindazolyl, isobenzofuranyl, isobenzothienyl, benzimidazolyl, benzoxazolyl, benzothiazolyl, arylvinylene, arylamido, arylcarboxamide, aralkylamine, quinolinyl, isoquinolinyl, cinnolyl, quinazolyl, naphthyridyl, triazolyl and tetrazolyl.

14. The composition as set forth in claim 13, wherein the aryl or heteroaryl radicals are independently selected from the group consisting of: phenyl, pyrrolyl, optionally substituted indolyl, and arylvinylene.

15. The composition as set forth in claim 10, wherein X is a covalent bond and R1 is heteroaryl.

16. The composition as set forth in claim 15, wherein R1 is indolyl.

17. The composition as set forth in claim 10, wherein R2 is (C$_1$-C$_4$)alkyl.

18. The composition as set forth in claim 10, wherein Y is a covalent bond and R3 is H.

19. A compound selected from the group consisting of:
methylphenylphosphinic acid 3-((E)-styryl)-1H-indazol-5-yl ester;
diphenylphosphinic acid 3-((E)-styryl)-1H-indazol-5-yl ester;
methylphenylphosphinic acid 3-(1H-indol-2-yl)-1H-indazol-5-yl ester;
diphenylphosphinic acid 3-(1H-indol-2-yl)-1H-indazol-5-yl ester;
methylphenylphosphinic acid 3-[5-(2-morpholin-4-ylethoxy)-1H-indol-2-yl]-1H-indazol-5yl ester;
phenylphosphonic acid 3-(1H-indol-2-yl)-1H-indazol-5-yl ester methyl ester;
phenylphosphonic acid 3-(1H-indol-2-yl)-1H-indazol-5-yl ester isopropyl ester;
phenylphosphonic acid 3-(1H-indol-2-yl)-1H-indazol-5-yl ester benzyl ester;
methylphosphonic acid 3-(1H-indol-2-yl)-1H-indazol-5-yl ester methyl ester;
phenylphosphonic acid methyl ester 3-(1H-ptrrol-2-yl)-1H-indazol-5-yl ester;
[3-((E)-styryl)-1H-indazol-5-yl]phosphonic acid dimethyl ester;
[3-((E)-styryl)-1H-indazol-5-yl]phosphonic acid monomethyl ester;
[3-((E)-styryl)-1H-indazol-5-yl]phosphonic acid diethyl ester;
[3-(1H-indol-2-yl)-1H-indazol-5-yl]phosphonic acid monomethyl ester;
(3-thiophen-2-yl-1H-indazol-5-yl)phosphonic acid monomethyl ester;
[3-(1H-pyrrol-2-yl)-1H-indazol-5-yl]phosphonic acid monomethyl ester;
dimethylphosphinic acid 3-(1H-indol-2-yl)-1H-indazol-5-yl ester;
methyl-phosphonic acid methyl ester 3-[5-(2-piperidin-1-yl-ethoxy)-1H-indol-2-yl]-1H-indazol-5-yl ester;
methylphosphonic acid mono-{3-[5-(2-piperazin-1-ylethoxy)-1H-indol-2-yl]-1H-indazol-5-yl} ester;
methylphosphonic acid mono-{3-[5-(2-diethylaminoethoxy)-1H-indol-2-yl]-1H-indazol-5-yl} ester;
methyl-phosphonic acid 3-[5-(2-diethylaminoethoxy)-1H-indol-2-yl]-1H-indazol-5yl ester methyl ester;
phenylphosphonic acid ethyl ester 3-(5-methoxy-1H-pyrrolo[3,2-b]pyridin-2-yl)-1H-indazol-5-yl ester;
phenylphosphonic acid 3-(5-methoxy-1H-pyrrolo[3,2-b]pyridin-2-yl)-1H-indazol-5-yl ester methyl ester;
phenylphosphonic acid methyl ester 3-styryl-1H-indazol-5-yl ester;
phenylphosphonic acid 3-thiophen-2-yl-1H-indazol-5-yl ester methyl ester;
phenylphosphonic acid 3-benzo[b]thiophen-2-yl-1H-indazol-5-yl ester methyl ester;
methylphosphonic acid methyl ester 3-[5-(2-morpholin-4-ylethoxy)-1H-indol-2-yl]-1H-indazol-5-yl ester;
methylphosphonic acid 3-[6-(2-diethylamino-ethoxy)-1H-indol-2-yl]-1H-indazol-5-yl ester methyl ester;
ethylphosphonic acid 3-(1H-indol-2-yl)-1H-indazol-5-yl ester methyl ester;
methylphosphonothioic acid O-[3-(1H-indol-2-yl)-1H-indazol-5-yl] ester O-methyl ester;
cyclohexylphosphonic acid 3-(1H-indol-2-yl)-1H-indazol-5-yl ester methyl ester; and
phenylphosphonic acid mono-[3-(1H-indol-2-yl)-1H-indazol-5-yl] ester;
or a pharmaceutically salt thereof.

* * * * *